United States Patent
Berkman et al.

(10) Patent No.: US 9,974,869 B2
(45) Date of Patent: *May 22, 2018

(54) CHELATED PSMA INHIBITORS

(71) Applicant: Cancer Targeted Technology LLC, Woodinville, WA (US)

(72) Inventors: Clifford Berkman, Pullman, WA (US); Bea Langton-Webster, Woodinville, WA (US); Xiaobing Wang, Redmond, WA (US)

(73) Assignee: Cancer Targeted Technology LLC, Woodinville, WA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/246,483

(22) Filed: Aug. 24, 2016

(65) Prior Publication Data

US 2017/0072075 A1 Mar. 16, 2017

Related U.S. Application Data

(63) Continuation of application No. 14/126,296, filed as application No. PCT/US2012/042283 on Jun. 13, 2012, now Pat. No. 9,446,157.

(60) Provisional application No. 61/497,206, filed on Jun. 15, 2011, provisional application No. 61/647,932, filed on May 16, 2012.

(51) Int. Cl.
| | |
|---|---|
| *A61K 51/04* | (2006.01) |
| *A61K 49/04* | (2006.01) |
| *C07B 59/00* | (2006.01) |
| *C07F 9/24* | (2006.01) |
| *C07F 9/6515* | (2006.01) |
| *C07F 9/6524* | (2006.01) |
| *C07F 9/6527* | (2006.01) |
| *C07F 9/6558* | (2006.01) |
| *C07F 9/6561* | (2006.01) |

(52) U.S. Cl.
CPC .......... *A61K 51/0489* (2013.01); *A61K 49/04* (2013.01); *A61K 51/0497* (2013.01); *C07B 59/004* (2013.01); *C07F 9/2458* (2013.01); *C07F 9/6515* (2013.01); *C07F 9/6524* (2013.01); *C07F 9/6527* (2013.01); *C07F 9/6561* (2013.01); *C07F 9/65583* (2013.01); *C07B 2200/05* (2013.01)

(58) Field of Classification Search
CPC ....... A61K 49/00; A61K 51/00; C07D 225/00
See application file for complete search history.

(56) References Cited

U.S. PATENT DOCUMENTS

| | | | |
|---|---|---|---|
| 7,368,100 B2 | 5/2008 | Brechbiel | |
| 7,696,185 B2 * | 4/2010 | Berkman | C07F 9/091 514/114 |
| 8,907,058 B2 * | 12/2014 | Low | A61K 47/48023 530/330 |

FOREIGN PATENT DOCUMENTS

WO 2012/064914 A2 5/2012

OTHER PUBLICATIONS

Lapi et al., "Assessment of an 18F-Labeled Phosphoramidate Peptidomimetic as a New Prostate-Specific Membrane Antigen-Targeted Imaging Agent for Prostate Cancer", The Journal of Nuclear Medicine, 2009, 50(12), 2042-2048.

Berkman, "Detection of prostate-specific membrane antigen on HUVECs in response to breast tumor-conditioned medium", International Journal of Oncology, 2011, 38(5), XP55034301.

Liu et al., "Prostate-specific membrane antigen-targeted photodynamic therapy induces rapid cytoskeletal disruption", Cancer Letters, 2010, 296(1), 106-112.

Liu et al., "Spacer length effects on in vitro imaging and surface accessibility of fluorescent inhibitors of prostate specific membrane antigen", Bioorganic & Medicinal Chemistry Letters, 2011, 21(23), 7013-7016.

Berkman, C. et al. "Substrate specificity of prostate-specific membrane antigen" Bioorg. Med. Chem. 2007, 15, 6678-6686.

Berkman, C. et al. "Pseudoirreversible Inhibition of Prostate-Specific Membrane Antigen by Phosphoramidate Peptidomimetics" Biochemistry 2008, 47, 12658-12660.

\* cited by examiner

*Primary Examiner* — Michael G Hartley
*Assistant Examiner* — Jagadishwar Samala
(74) *Attorney, Agent, or Firm* — McDonnell Boehnen Hulbert & Berghoff LLP

(57) ABSTRACT

Compounds as defined herein are provided which are useful in (1) diagnostic methods for detecting and/or identifying cells presenting PSMA; (2) compositions comprising a compound of the invention together with a pharmaceutically acceptable diluent; and (3) methods for imaging prostate cancer cells.

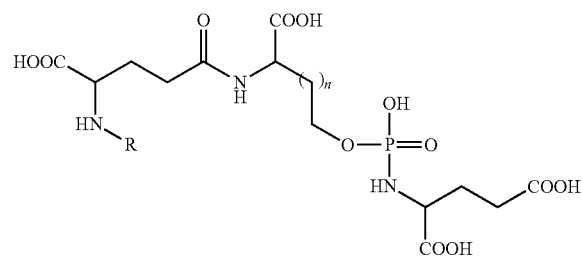

10 Claims, 7 Drawing Sheets

Figure 2
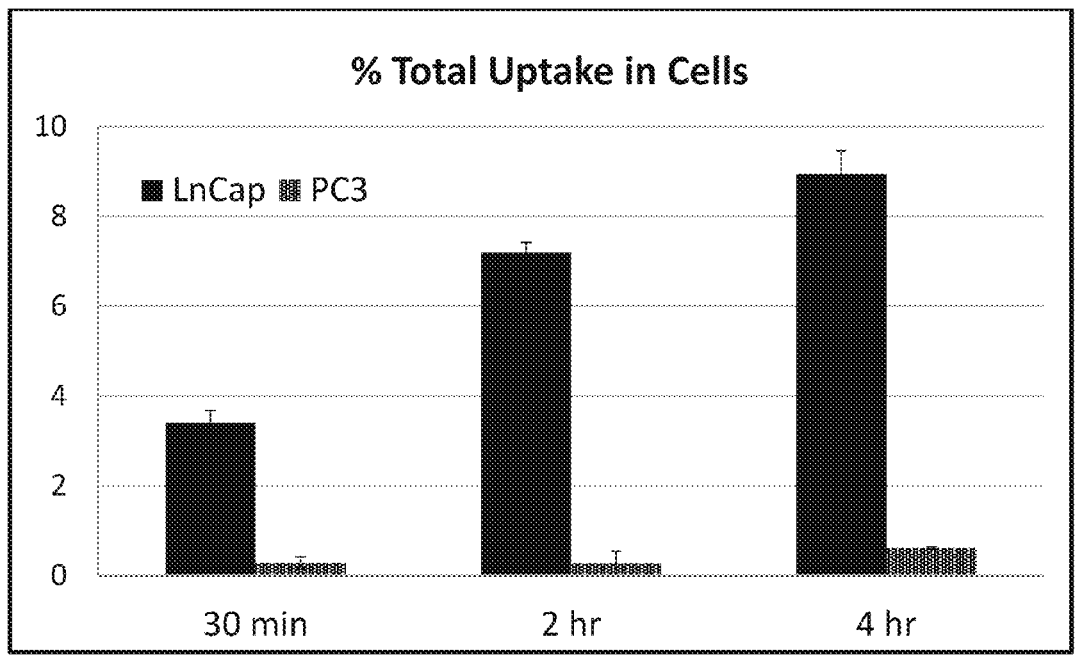
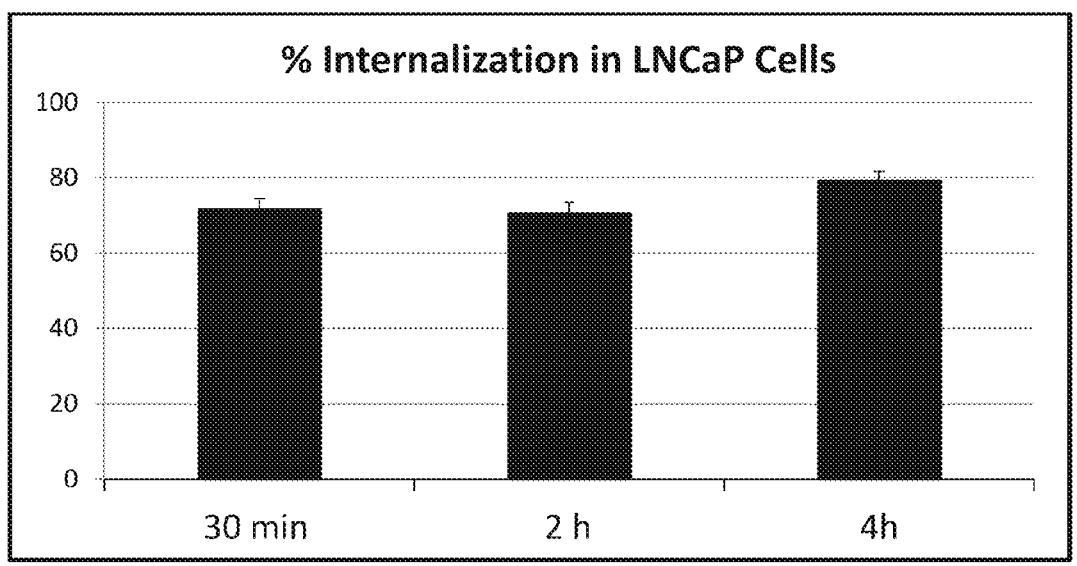

Figure 7

| 1* | 2* | 3* |
|----|----|----|
| S  | S  | S  |
| S  | S  | R  |

| 1* | 2* | 3* |
|----|----|----|
| S  | R  | S  |
| R  | S  | S  |

| 1* | 2* | 3* |
|----|----|----|
| S  | R  | R  |
| R  | S  | R  |

| 1* | 2* | 3* |
|----|----|----|
| R  | R  | S  |
| R  | R  | R  |

CHELATED PSMA INHIBITORS

CROSS-REFERENCE TO RELATED APPLICATIONS

This application claims the benefit of priority to U.S. Provisional Application Ser. No. 61/647,932, filed May 16, 2012 and U.S. Provisional Application Ser. No. 61/497,206, filed Jun. 15, 2011, which are hereby incorporated by reference in their entirety.

STATEMENT OF GOVERNMENT INTEREST

This application was supported by Grant No. 1R44CA153481-01A1 and Grant No. R01CA140617 awarded by the National Cancer Institute. The U.S. government has certain rights in the invention.

BACKGROUND OF THE INVENTION

Field of the Invention

The present invention relates to small molecules having high affinity and specificity to prostrate-specific membrane antigen (PSMA) and methods of using them for diagnostic and therapeutic purposes.

SUMMARY OF THE RELATED ART

Prostate-specific membrane antigen (PSMA) is uniquely overexpressed on the surface of prostate cancer cells as well as in the neovasculature of a variety of solid tumors. As a result, PSMA has attracted attention as a clinical biomarker for detection and management of prostate cancer. Generally, these approaches utilize an antibody specifically targeted at PSMA to direct imaging or therapeutic agents. For example, ProstaScint (Cytogen, Philadelphia, Pa.), which has been approved by the FDA for the detection and imaging of prostate cancer, utilizes an antibody to deliver a chelated radioisotope (Indium-111). However, it is now recognized that the ProstaScint technology is limited to the detection of dead cells and therefore its clinical relevance is questionable.

The success of cancer diagnosis and therapy using antibodies is limited by challenges such as immunogenicity and poor vascular permeability. In addition, large antibodies bound to cell-surface targets present a barrier for subsequent binding of additional antibodies at neighboring cell-surface sites resulting in a decreased cell-surface labeling.

In addition to serving as a cell-surface target for antibodies delivering diagnostic or therapeutic agents, a largely overlooked and unique property of PSMA is its enzymatic activity. That is, PSMA is capable of recognizing and processing molecules as small as dipeptides. Despite the existence of this property, it has been largely unexplored in terms of the development of novel diagnostic and therapeutic strategies. There are a few recent examples in the literature that have described results in detecting prostate cancer cells using labeled small-molecule inhibitors of PSMA.

Certain phosphoramidate and phosphate PSMA inhibitors have been described in U.S. Patent Application Publication No. US-2007-0219165-A1.

SUMMARY OF THE INVENTION

Provided herein are PET diagnostics and therapeutics for prostate cancer that capitalize on the potency and specific affinity of small-molecule inhibitors to PSMA. The diagnostic agents can be used to monitor and stratify patients for treatment with appropriate therapeutic agents.

Our probes are comprised of a PSMA-targeting a peptidomimetic core coupled to an imaging reporter or to a therapeutic radiotracer. In one aspect, we have demonstrated that $^{99m}$Tc-chelate structures can be used be used to radiolabel our PSMA inhibitors and that the labeled probe specifically targets and internalizes into PSMA-expressing prostate cancer cells and tumors.

In another aspect, we have developed a direct labeling protocol using the PET isotope $^{68}$Ga— with a chelate-structure-PSMA inhibitor conjugate that can be performed in a typical radiopharmacy and may provide an efficient synthesis pathway while maintaining the necessary biological activity. These PSMA imaging constructs can serve as the foundation for a PET imaging agent, and can be easily modified to incorporate other PET imaging radionuclides such as $^{89}$Zr and $^{64}$Cu, and a radiometal such as $^{186/188}$Re, $^{90}$Y, $^{177}$Lu, $^{153}$Sm, $^{213}$Bi, $^{225}$Ac, $^{223}$Ra in the chelate structure that can serve as a therapeutic agent for targeted radiotherapy.

For example, the design of PSMA-targeted imaging agents can be modified and optimized for chelated $^{89}$Zr or $^{64}$Cu or $^{68}$Ga labeling using desferrioxamine-p-SCN or -p-SCN-Bn-NOTA, p-SCN-Bn-PCTA, p-SCN-Bn-Oxo-DO3A, and DOTA-NHS amine-reactive chelate structures as examples. The labeling conditions may ensure efficient and reproducible labeling in clinical radiopharmacies for PET imaging of prostate tumors. PSMA-targeted imaging agents can also be modified with $^{186/188}$Re, $^{90}$Y, $^{177}$Lu, $^{153}$Sm, $^{213}$Bi, $^{225}$Ac, $^{223}$Ra in chelated structures to achieve a PSMA targeted radiotracer with therapeutic efficacy.

The labeled tracers herein are examples of suitable imaging agents for PSMA positive tumors in vivo.

Accordingly, in one aspect the present disclosure provides compounds of the formula

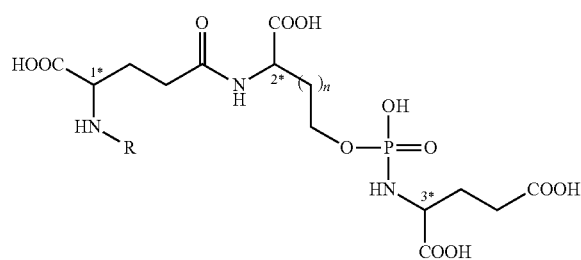

or a pharmaceutically acceptable salt thereof, wherein n is 0 or greater (preferably 0, 1, or 2); and R comprises a divalent linking group bonded to a chelating agent, wherein the chelating agent is optionally associated with a PET-active radioisotope. In the foregoing structure, 1*, 2*, and 3* are chiral centers that are independently racemic (rac) or in the S or R stereoconfiguration. Thus, compounds according to this aspect include those with the combinations of stereoconfigurations in FIG. 7, and mixtures thereof.

In another aspect the present disclosure provides pharmaceutical compositions comprising a compound of the preceding aspect and a pharmaceutically acceptable carrier.

In another aspect the present disclosure provides methods for imaging one or more prostate cancer cells or tumor-associated vasculature in a patient comprising administering

BRIEF DESCRIPTION OF THE DRAWINGS

FIG. 2 Uptake and Internalization on a Chelated $^{99m}$Tc Radiolabeled PSMA Inhibitor (see, Nedrow-Byers, J. et al., *The Prostate.* 2011, (in press)).

FIG. 7 shows combinations of S and R stereoconfigurations for compound formulae disclosed herein having carbon atoms marked with 1*, 2*, and 3*.

DETAILED DESCRIPTION OF THE INVENTION

Figure 1:
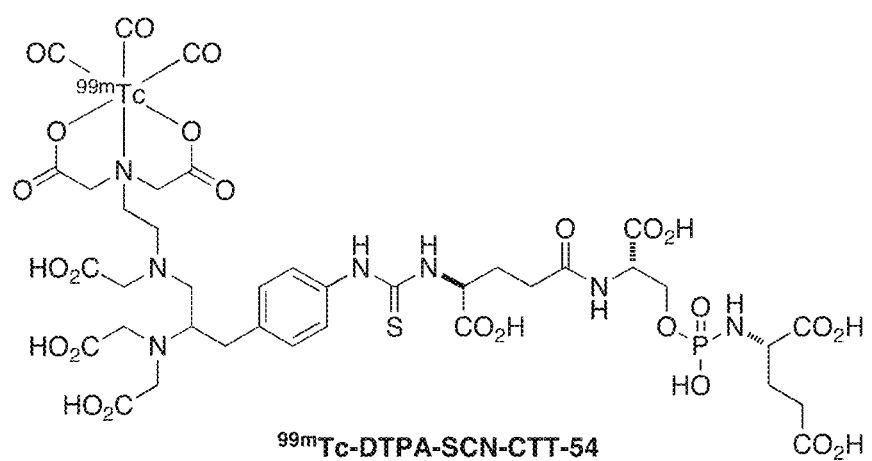
FIG. 1 $^{99m}$Tc Radiolabled PSMA Inhibitor bearing a chelate structure

Isotopes that are currently used in PET imaging studies are attractive and potentially better alternatives to $^{18}$F. $^{68}$Ga, $^{64}$Cu and $^{89}$Zr are available isotopes that are being assessed for PET imaging due to their light metal properties and the ability to bind to chelating agents (1). We have chosen isotopes $^{186/188}$Re, $^{90}$Y, $^{177}$Lu, $^{153}$Sm, $^{213}$Bi, $^{225}$Ac, $^{223}$Ra as radioisotopes with potential therapeutic efficacy.

It has been shown that the chelating agent, DOTA (1,4,7,10-tetraazacyclododecane-1,4,7,10-tetraacetic acid), (or modified derivatives thereof), is an excellent ligand for binding of gallium; and DOTA-peptides can be rapidly and efficiently labeled with $^{68}$Ga at high specific activities (2).

We have already prepared and tested these chelating agents and these types of chelating agents have been routinely used for PET imaging agents (1). The rationale for the $^{68}$Ga metal isotope is driven by biological, cost and patient considerations. The $^{68}$Ga isotope is the most attractive of the radiometals, since it's half-live is closer to that of $^{18}$F and would facilitate imaging soon after administration with reduced exposure to the patient. It has been shown that due to rapid diffusion of many small molecules and peptides, the 68 minute half-life of $^{68}$Ga very closely matches the pharmacokinetics of these molecules resulting in better tumor localization and faster blood clearance. In addition, a significant factor in selecting $^{68}$Ga is that it can be cost effectively and continuously produced by a commercially available $^{68}$Ge/$^{68}$Ga generator, alleviating the need for proximity of PET centers to the cyclotrons needed for the production of, for example, $^{18}$F (2).

According to the Clinical Trials Network (www.clinicaltrials.gov) there are currently four PET imaging oncology clinical trials using $^{64}$Cu labeled targeting agents; two in breast cancer using $^{64}$Cu-DOTA-Trastuzumab (3) and two for Non-Small Cell Lung Cancer using $^{64}$Cu-ATSM (4). There are two ongoing PET imaging Clinical Trials with $^{68}$Ga. One using $^{68}$Ga labeled F(ab')2-trastuzumab for breast cancer and one using $^{68}$Ga-bombesin (5) for prostate cancer. $^{89}$Zr is also being tested with antibody targeted imaging (6, 7) in seven clinical studies testing imaging capabilities in breast cancer and renal cell carcinoma.

We have preserved the modular approach to install metallic PET radionuclides into our PSMA-targeting inhibitors. We functionalize our PSMA-targeting inhibitors with selected amine-reactive bifunctional chelators and subsequently radiolabel these conjugates with complementary metallic radionuclides. Amine-reactive chelate structures for these radionuclides are commercially available such as DOTA-NHS and others noted in the following table, where the chelator can be attached in the R groups via the divalent linking group as defined herein ("L" in the following):

| Chelator | Structure | R |
| --- | --- | --- |
| DOTA | (1,4,7,10-tetraazacyclododecane with four CH$_2$COOH arms; all four arms terminate in COOH) | (same macrocycle with three COOH arms and one arm as —CH$_2$—C(=O)—L—) |
| DOTA-NHS | (macrocycle with three COOH arms and one arm as —CH$_2$—C(=O)—O—N-succinimidyl) | (macrocycle with three COOH arms and one arm as —CH$_2$—C(=O)—L—) |

-continued
| Chelator | Structure | R |
|---|---|---|
| p-SCN-Bn-NOTA | 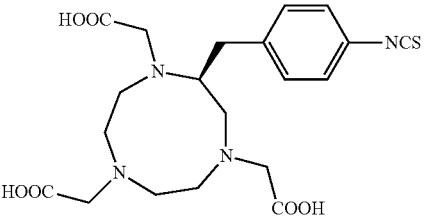 | 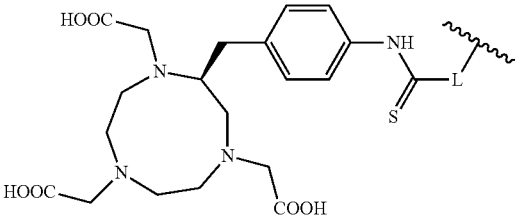 |
| p-SCN-Bn-PCTA | 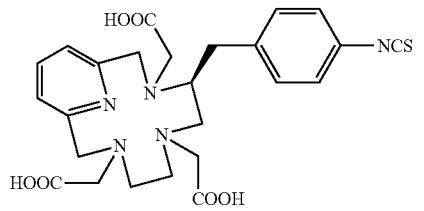 | 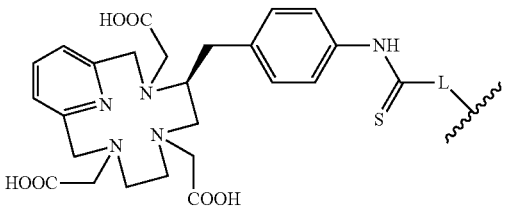 |
| p-SCN-Bn-Oxo-DO3A | 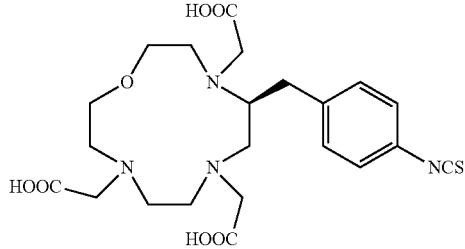 | 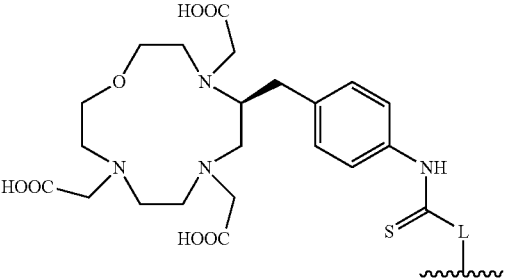 |
| and desferri-oxamine-p-SCN | 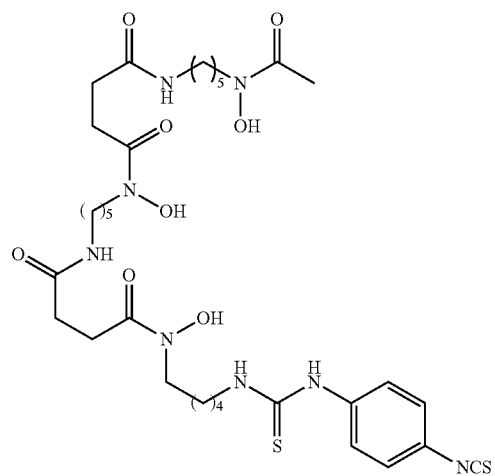 | 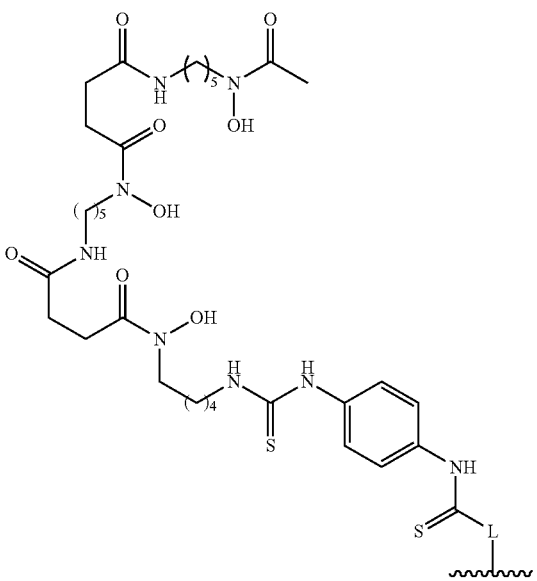 |
| Diethylene-triamine-pentaacetic acid (DTPA) | 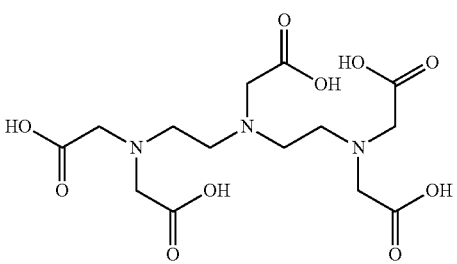 [SMILES: O=C(O)CN(CCN(CC(=O)O)CC(=O)O)CCN(CC(=O)O)CC(=O)O] | 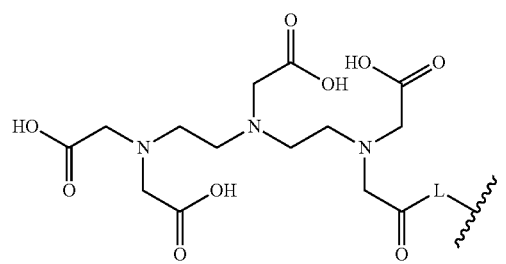 |

| Chelator | Structure | R |
|---|---|---|
| 1,4,8,11-tetraaza-cyclotetradecane 1,4,8,11-tetraacetic acid (TETA) | 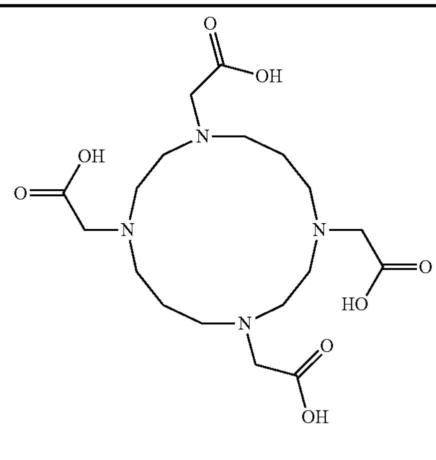 | |

If necessary, additional bifunctional chelators can also be readily prepared using literature procedures.

In one aspect the present disclosure provides compounds of the formula

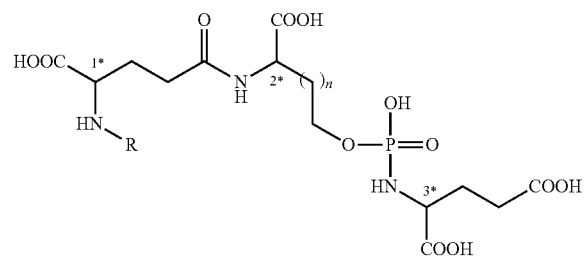

or a pharmaceutically acceptable salt thereof, wherein
n is 0 or greater (e.g., 0-10 or 0-6 or 0-5 or 0-4 or 0-3 or 0, 1, or 2); and
R comprises a divalent linking group bonded to a chelating agent, wherein the chelating agent is optionally associated with a PET-active radioisotope.

In the foregoing structure, 1*, 2*, and 3* are chiral centers that are independently racemic (rac) or in the S or R stereoconfiguration. Thus, compounds according to this aspect include those with the combinations of stereoconfigurations in FIG. 7, and mixtures thereof.

In one embodiment, the compounds are of the formula

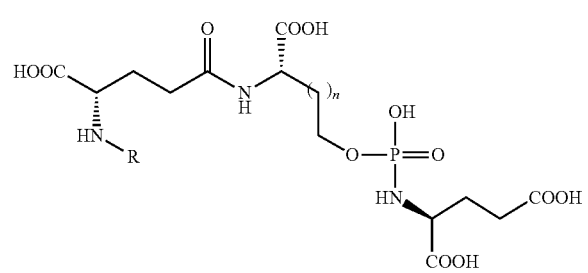

wherein n is 0 or greater (e.g., 0-10 or 0-6 or 0-5 or 0-4 or 0-3 or 0, 1, or 2); and R comprises a divalent linking group bonded to a chelating agent, wherein the chelating agent is associated with a PET-active radioisotope, or a pharmaceutically acceptable salt thereof.

In another embodiment, the compounds are of the formula

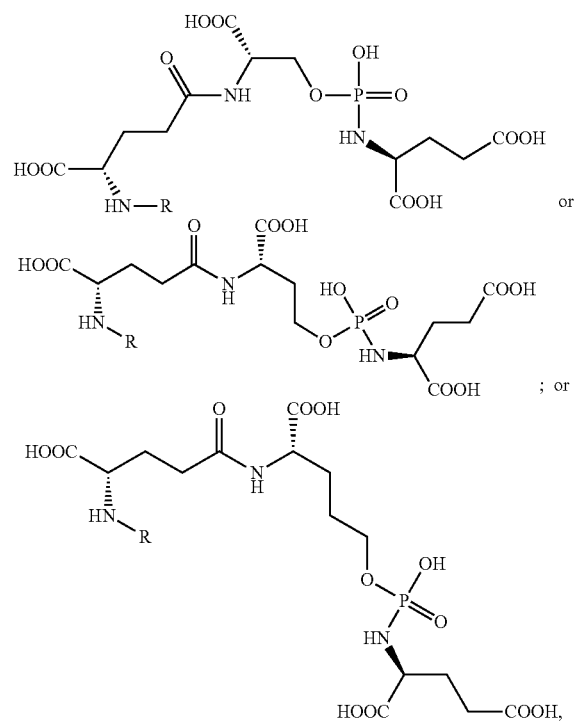

wherein R comprises a divalent linking group bonded to a chelating agent, wherein the chelating agent is associated with a PET-active radioisotope, or a pharmaceutically acceptable salt thereof.

Divalent linking groups include groups of the formula, $-(C_0\text{-}C_{10} \text{ alkyl-Q})_{0-1}\text{-}C_0\text{-}C_{10}$ alkyl-, wherein Q is a bond, aryl (e.g., phenyl), heteroaryl, $C_3\text{-}C_8$ cycloalkyl, or heterocyclyl; and no more than one methylene in each alkyl group is optionally and independently replaced by $-O-$, $-S-$, $-N(R^{oo})-$, $-C(H)=C(H)-$, $-C\equiv C-$, $-C(O)-$, $-S(O)-$, $-S(O)_2-$, $-P(O)(OR^{oo})-$, $-OP(O)(OR^{oo})-$, $-P(O)(OR^{oo})O-$, $-N(R^{oo})P(O)(OR^{oo})-$, $-P(O)(OR^{oo})N(R^{oo})-$, $-OP(O)(OR^{oo})O-$, $-OP(O)(OR^{oo})N(R^{oo})-$, $-N(R^{oo})P(O)(OR^{oo})O-$, $-N(R^{oo})P(O)(OR^{oo})N(R^{oo})-$, $-C(O)O-$, $-C(O)N(R^{oo})-$, $-OC$ (O)—, —N(R$^{00}$)C(O)—, —S(O)O—, —OS(O)—, —S(O)N(R$^{00}$)—, —N(R$^{00}$)S(O)—, —S(O)$_2$O—, —OS(O)$_2$—, —S(O)$_2$N(R$^{00}$)—, —N(R$^{00}$)S(O)$_2$—, OC(O)O—, —OC(O)N(R$^{00}$)—, —N(R$^{00}$)C(O)O—, —N(R$^{00}$)C(O)N(R$^{00}$)—, —OS(O)O—, —OS(O)N(R$^{00}$)—, —N(R$^{00}$)S(O)O—, —N(R$^{00}$)S(O)N(R$^{00}$)—, —OS(O)$_2$O—, —OS(O)$_2$N(R$^{00}$)—, —N(R$^{00}$)S(O)$_2$O—, or —N(R$^{00}$)S(O)$_2$N(R$^{00}$)—, wherein each R$^{00}$ is independently hydrogen or $C_1$-$C_6$ alkyl.

In other embodiments, divalent linking groups is selected from one of the following groups of the formula, wherein in each instance, the *-end is attached to the chelating agent:
(a) *—(OCH$_2$CH$_2$)$_n$—, wherein n is 1-20 (e.g., 4-12, or 4, or 8, or 12);
(b) —(C(O)—(CH$_2$)$_{0-1}$—CH(R$^1$)N(R$^2$))$_m$—*, wherein m is 1-8;
  each R$^1$ is independently the side chain of a natural or unnatural amino acid (e.g., each R$^1$ is independently hydrogen, $C_1$-$C_6$alkyl, aryl, heteroaryl, aryl$C_1$-$C_6$alkyl, or heteroaryl$C_1$-$C_6$alkyl, wherein the alkyl, arylalkyl, and heteroarylalkyl groups are optionally substituted with 1, 2, 3, 4, or 5 R$^{11}$ groups, wherein each R$^{11}$ is independently halo, cyano, —OR$^{12}$, —SR$^{12}$, —N(R$^{12}$)$_2$, —C(O)OR$^{12}$, —C(O)N(R$^{12}$)$_2$, —N(R$^{12}$)C(=NR$^{12}$)N(R$^{12}$)$_2$, or $C_1$-$C_6$alkyl, wherein each R$^{12}$ is independently hydrogen or $C_1$-$C_6$alkyl);
  each R$^2$ is independently hydrogen or taken together with R$^1$ within the same residue to form a heterocyclyl (e.g., having 5-members);
(c) —(C(O)(CH$_2$)$_p$—(C(O))$_{0-1}$—NH)—*, wherein p is 1-30 (e.g., p is 1-7) (e.g., 6-aminohexanoic acid, —C(O)(CH$_2$)$_5$NH—*);
(d) —(C(O)—(CH$_2$)$_r$-phenyl-(G)$_{0-1}$-(CH$_2$)$_q$—(C(O))$_{0-1}$—NH)—*,
  wherein G is —O— or —N(H)—, -r and q are each independently 0-30 (e.g., 0-20; or 0-10, or 0-6, or 1-6) (e.g., —(C(O)-phenyl-N(H)(CH$_2$)$_q$—(C(O))$_q$—NH)—*, wherein q is 1-6; or —(C(O)—(CH$_2$)$_r$-phenyl-(CH$_2$)$_q$—NH)—*, wherein r and q are each independently 0-6;
  or the two substituents on the phenyl are para to one another, such as in 4-aminomethylbenzoic acid,

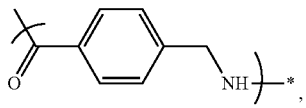

where r is 0, and q is 1; or as in 4-aminoethylbenzoic acid,

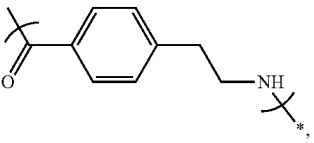

where r is 0 and q is 2); or (e)

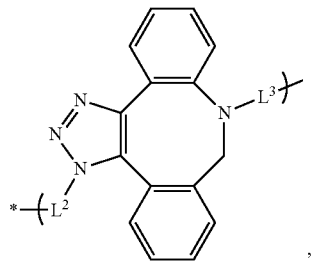

-continued

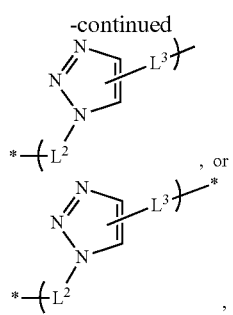

wherein
  L$^2$ is —(CH$_2$)$_t$N(H)—*, wherein t is 1 to 30; and
  L$^3$ is #—(CH$_2$)$_u$—C(O)—, #—(CH$_2$)$_u$—Z—Y—C(O)—, #—C(O)—(CH$_2$)—C(O)— or #—C(O)—(CH$_2$)$_u$—Z—Y—C(O)—, wherein
  the # end of L$^3$ is attached to the dibenzocyclooctyne or triazolyl group above,
  u is 1 to 30;
  Y is —(CH$_2$)$_v$— or —CH$_2$CH$_2$—(OCH$_2$CH$_2$)$_n$—, wherein n is 1-20 (e.g., 4-12, or 4, or 8, or 12), and wherein the -end is attached to Z;
  and Z is —C(O)O—, —C(O)N(R$^{00}$)—, —OC(O)—, —N(R$^{00}$)C(O)—, —S(O)$_2$N(R$^{00}$)—, —N(R$^{00}$)S(O)$_2$—, —OC(O)O—, —OC(O)N(R$^{00}$)—, —N(R$^{00}$)C(O)O—, or —N(R$^{00}$)C(O)N(R$^{00}$)—,
  wherein each R$^{00}$ is independently hydrogen or $C_1$-$C_6$ alkyl;

and (f) combinations of the preceding, wherein in each instance, the *-end is attached to the chelating agent, such as:
(i) —(CH$_2$CH$_2$O)$_n$—(C(O)(CH$_2$)$_p$—(C(O))$_{0-1}$—NH)—*, where n and p are as defined above (e.g., n is 4 and p is 6);
(ii) —(CH$_2$CH$_2$O)$_n$—(C(O)—(CH$_2$)$_{0-1}$—CH(R$^1$)N(R$^2$))$_m$—*, where R$^1$, R$^2$, n and m are as defined above (e.g., n is 4 and m is 2);
(iii) —(CH$_2$CH$_2$O)$_n$—(C(O)—(CH$_2$)$_r$-phenyl-(G)$_{0-1}$-(CH$_2$)$_q$—(C(O))$_{0-1}$—NH)—*, where G, n, q, and r are as defined above (e.g., n is 4, q is 1, and r is 0);
(iv) —C(O)—(CH$_2$)$_{0-1}$—CH(R$^1$)N(R$^2$))$_m$—(C(O)(CH$_2$)$_p$—(C(O))$_{0-1}$—NH)—*, where R$^1$, R$^2$ m and p are as defined above (e.g., m is 2 and p is 6);
(v) —(C(O)—(CH$_2$)$_{0-1}$—CH(R$^1$)N(R$^2$))$_m$—(C(O)—(CH$_2$)$_r$-phenyl-(G)$_{0-1}$-(CH$_2$)$_q$—(C(O))$_{0-1}$—NH)—*, where G, R$^1$, R$^2$, m, q, and r are as defined above (e.g., m is 2, q is 1, and r is 0; or m is 2, q is 2, and r is 0);
(vi) —(C(O)(CH$_2$)$_p$—(C(O))$_{0-1}$—NH)—(C(O)—(CH$_2$)$_r$-phenyl-(G)$_{0-1}$-(CH$_2$)$_q$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);
(vii) —(C(O)(CH$_2$)$_p$—(C(O))$_{0-1}$—NH)—(C(O)—(CH$_2$)$_{0-1}$—CH(R$^1$)N(R$^2$))$_m$—*, where R$^1$, R$^2$, m and p are as defined above (e.g., m is 2 and p is 6);
(viii) —(C(O)—(CH$_2$)$_r$-phenyl-(G)$_{0-1}$-(CH$_2$)$_q$—(C(O))$_{0-1}$—NH)—(C(O)—(CH$_2$)$_{0-1}$—CH(R$^1$)N(R$^2$))$_m$—*, where G, R$^1$, R$^2$, m, q, and r are as defined above (e.g., m is 2, q is 1, and r is 0; or m is 2, q is 2, and r is 0);

(ix) —(C(O)—(CH$_2$)$_r$-phenyl-(G)$_{0-1}$-(CH$_2$)$_q$—(C(O))$_{0-1}$—NH)—(C(O)(CH$_2$)$_p$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(x) —(C(O)(CH$_2$)$_p$—(C(O))$_{0-1}$—NH)—(CH$_2$CH$_2$O)$_n$—*, where n and p are as defined above (e.g., n is 4 and p is 6);

(xi) —(C(O)—(CH$_2$)$_{0-1}$—CH(R$^1$)N(R$^2$))$_m$—(CH$_2$CH$_2$O)$_n$—*, where R$^1$, R$^2$, n and m are as defined above (e.g., n is 4 and m is 2); and (xii) —(C(O)—(CH$_2$)$_r$-phenyl-(G)$_{0-1}$-(CH$_2$)$_q$—(C(O))$_{0-1}$—NH)—(CH$_2$CH$_2$O)$_n$—*, where G, n, q, and r are as defined above (e.g., n is 4, q is 1, and r is 0; n is 4, q is 2, and r is 0);

(xiii) —(C(O)(CH$_2$)$_p$N(H)C(O)(CH$_2$)$_p$NH—)*, where each p is independently as defined above (e.g., each p is 5, —C(O)(CH$_2$)$_5$NH—C(O)(CH$_2$)$_5$NH—*); (xiv) a covalent bond.

In other embodiments, divalent linking groups is selected from one of the following groups of the formula, wherein in each instance, the *-end is attached to the chelating agent:

(xv) —(C(O)(CH$_2$)$_p$—(C(O))$_{0-1}$—NH)—*, wherein p is 1-7, (e.g., 6-aminohexanoic acid, —C(O)(CH$_2$)$_5$NH—*);

(xvi) —(C(O)—(CH$_2$)$_r$-phenyl-(G)$_{0-1}$-(CH$_2$)$_q$—(C(O))$_{0-1}$—NH)—*, wherein G is —N(H)—, -r is 0-6 (e.g., 0-3, or 0-2, or 0, or 1, or 2, or 1-6), q is 1-6 (e.g., 1-3, or 1-2, or 1, or 2) (e.g., the two substituents on the phenyl are para to one another, such as in 4-aminomethylbenzoic acid,

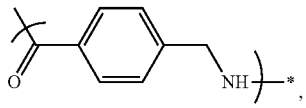

where r is 0 and q is 1; or as in 4-aminoethylbenzoic acid,

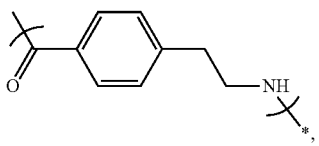

where r is 0 and q is 2); or (xvii) —(C(O)(CH$_2$)$_p$—(C(O))$_{0-1}$—NH)—C(O)—(CH$_2$)$_r$-phenyl-(G)$_{0-1}$-(CH$_2$)$_q$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(xviii) —(C(O)—(CH$_2$)$_r$-phenyl-(G)$_{0-1}$-(CH$_2$)$_q$—(C(O))$_{0-1}$—NH)—(C(O)(CH$_2$)$_p$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(xix) —(C(O)(CH$_2$)$_p$N(H)C(O)(CH$_2$)$_p$NH—)*, where each p is independently as defined above (e.g., each p is 5, —C(O)(CH$_2$)$_5$NH—C(O)(CH$_2$)$_5$NH—);

(xx) a covalent bond.

In other embodiments, divalent linking groups is selected from one of the following groups of the formula, wherein in each instance, the *-end is attached to the chelating agent:

(xv) —(C(O)(CH$_2$)$_p$—(C(O))$_{0-1}$—NH)—*, wherein p is 4-6, (e.g., 6-aminohexanoic acid, —C(O)(CH$_2$)$_5$NH—*);

(xvi) —(C(O)—(CH$_2$)$_r$-phenyl-(G)$_{0-1}$-(CH$_2$)$_q$—(C(O))$_{0-1}$—NH)—*, wherein G is —N(H)—, r is 0-6 and q is 1-3 (e.g., the two substituents on the phenyl are para to one another, such as in 4-aminomethylbenzoic acid,

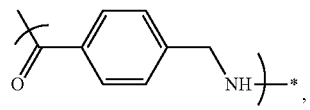

where q is 1; or as in 4-aminoethylbenzoic acid,

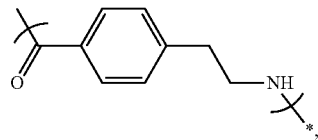

where q is 2); or (xvii) —(C(O)(CH$_2$)$_p$—(C(O))$_{0-1}$—NH)—C(O)—(CH$_2$)$_r$-phenyl-(G)$_{0-1}$-(CH$_2$)$_q$—(C(O))$_{0-1}$—NH)—*, where p, q, and r are as defined above (e.g., p is 6, q is 1, and r is 0; p is 6, q is 2, or r is 0; p is 5, q is 1, and r is 0; or p is 5, q is 2, and r is 0);

(xviii) —(C(O)—(CH$_2$)$_r$-phenyl-(G)$_{0-1}$-(CH$_2$)$_q$—(C(O))$_{0-1}$—H)—(C(O)(CH$_2$)$_p$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(xix) —(C(O)(CH$_2$)$_p$N(H)C(O)(CH$_2$)$_p$NH—)*, where each p is independently as defined above (e.g., each p is 5, —C(O)(CH$_2$)$_5$NH—C(O)(CH$_2$)$_5$NH—*);

(xx) a covalent bond.

In other embodiments, divalent linking groups is selected from one of the following groups of the formula, wherein in each instance, the *-end is attached to the chelating agent:

(xxi) —C(O)(CH$_2$)$_5$NH—*;

(xxii)

(xxiii)
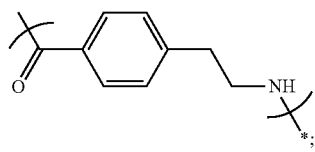

(xxiv)
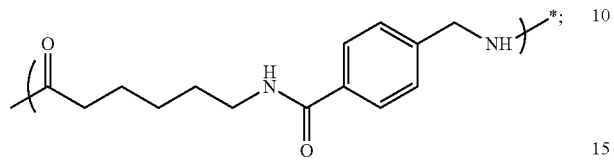

(xxv)
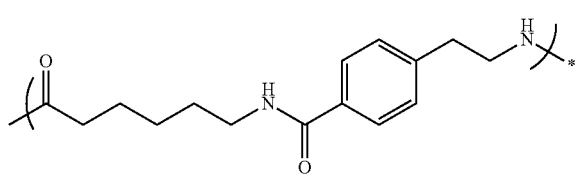

(xxvi)
—C(O)(CH₂)₅NH—C(O)(CH₂)₅NH—*;

(xxvii)
a covalent bond.

In an embodiment of any of the preceding embodiment, the compound is of the formula,

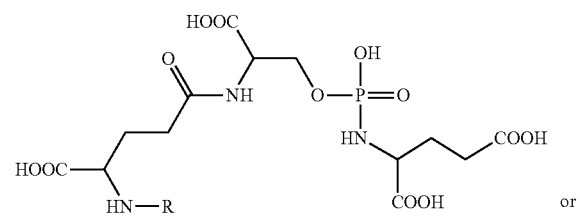

or

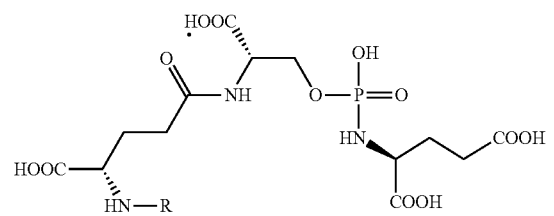

or a pharmaceutically acceptable salt thereof.

In the foregoing structure, 1*, 2*, and 3* are chiral centers that are independently racemic (rac) or in the S or R stereoconfiguration. Thus, compounds according to this aspect include those with the combinations of stereoconfigurations in FIG. 7, and combinations thereof.

In an embodiment of any of the preceding embodiment, the compound is of the formula,

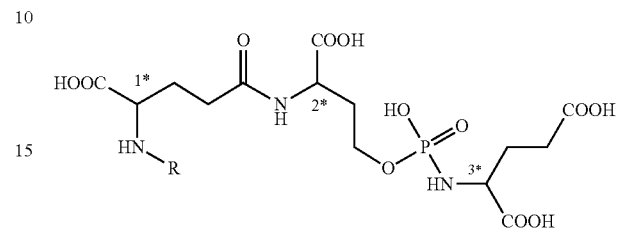

or a pharmaceutically acceptable salt thereof.

In the foregoing structure, 1*, 2*, and 3* are chiral centers that are independently racemic (rac) or in the S or R stereoconfiguration. Thus, compounds according to this aspect include those with the combinations of stereoconfigurations in FIG. 7, and combinations thereof.

In an embodiment of any of the preceding embodiment, the compound is of the formula,

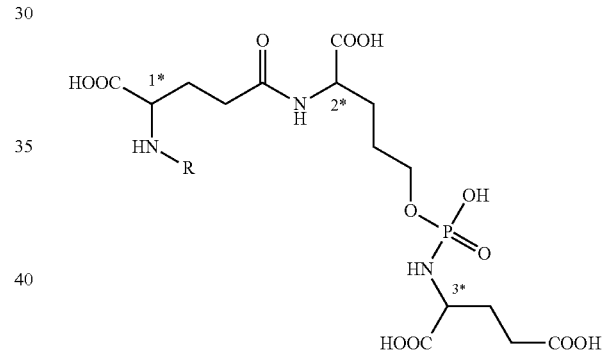

or a pharmaceutically acceptable salt thereof.

In the foregoing structure, 1*, 2*, and 3* are chiral centers that are independently racemic (rac) or in the S or R stereoconfiguration. Thus, compounds according to this aspect include those with the combinations of stereoconfigurations in FIG. 7, and any combinations thereof.

Recently, we have constructed a CTT-54 conjugate with the bifunctional chelator p-SCN-Bn-DTPA and subsequently labeled it with ⁹⁹ᵐTc to generate the analogous SPECT probe ⁹⁹ᵐTc-DTPA-SCN-CTT-54 (FIG. 1).

| CTT-54 | L-□-glutamyl-O-[{[(1S)-1,3-dicarboxypropyl]amino}(hydroxy)phosphoryl]-L-serine | 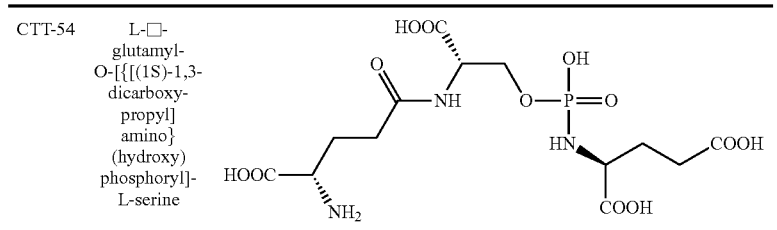 |

Examples of suitable compounds for associating with a radiolabel include, but are not limited to (where the *-end is attached to the chelating agent):

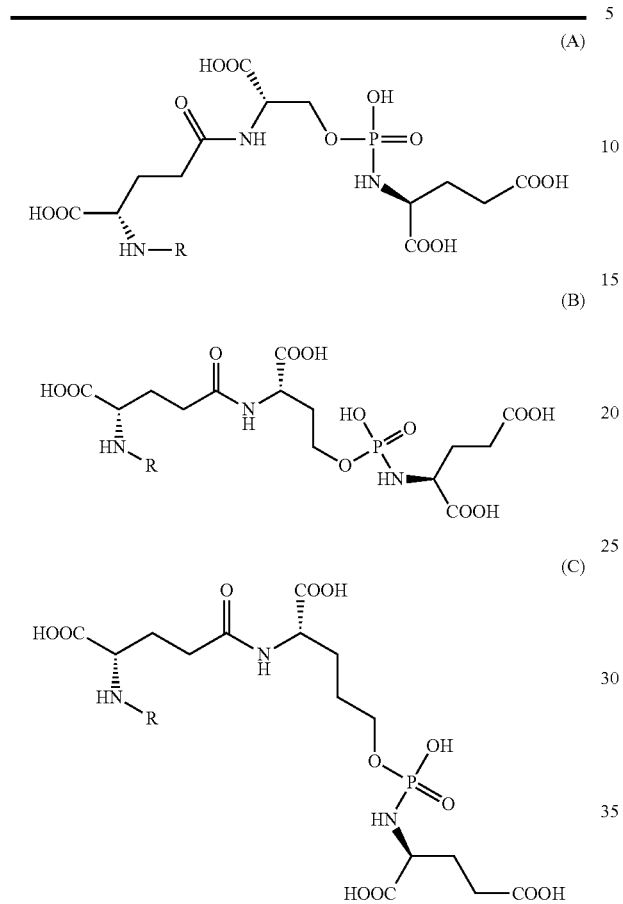

| Divalent linking group | Ref. No. |
|---|---|
| —(CH₂CH₂O)₄—* | (1) |
| —(CH₂CH₂O)₈—* | (2) |
| —(CH₂CH₂O)₁₂—* | (3) |
| —C(O)(CH₂)₅NH—* | (4) |

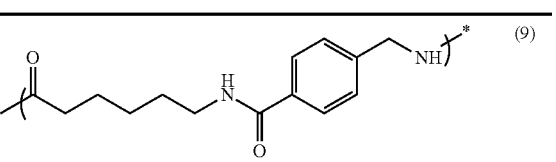

(5)

(6)

—(CH₂CH₂O)₄—C(O)(CH₂)₅NH—* (7)

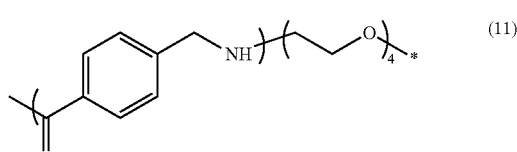

(8)

-continued

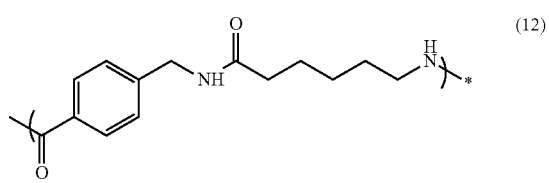

(9)

—C(O)(CH₂)₅NH—(CH₂CH₂O)₄—* (10)

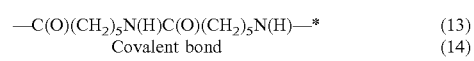

(11)

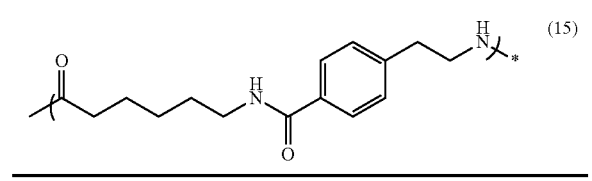

(12)

—C(O)(CH₂)₅N(H)C(O)(CH₂)₅N(H)—* (13)
Covalent bond (14)

(15)

| | R-group | |
|---|---|---|
| Structure | Divalent linking group | Chelating group |
| (A) | (1) | DOTA-NHS |
| (A) | (1) | p-SCN-Bn-NOTA |
| (A) | (1) | p-SCN-Bn-PCTA |
| (A) | (1) | p-SCN-Bn-Oxo-DO3A |
| (A) | (1) | desferrioxamine-p-SCN |
| (A) | (2) | DOTA-NHS |
| (A) | (2) | p-SCN-Bn-NOTA |
| (A) | (2) | p-SCN-Bn-PCTA |
| (A) | (2) | p-SCN-Bn-Oxo-DO3A |
| (A) | (2) | desferrioxamine-p-SCN |
| (A) | (3) | DOTA-NHS |
| (A) | (3) | p-SCN-Bn-NOTA |
| (A) | (3) | p-SCN-Bn-PCTA |
| (A) | (3) | p-SCN-Bn-Oxo-DO3A |
| (A) | (3) | desferrioxamine-p-SCN |
| (B) | (1) | DOTA-NHS |
| (B) | (1) | p-SCN-Bn-NOTA |
| (B) | (1) | p-SCN-Bn-PCTA |
| (B) | (1) | p-SCN-Bn-Oxo-DO3A |
| (B) | (1) | desferrioxamine-p-SCN |
| (B) | (2) | DOTA-NHS |
| (B) | (2) | p-SCN-Bn-NOTA |
| (B) | (2) | p-SCN-Bn-PCTA |
| (B) | (2) | p-SCN-Bn-Oxo-DO3A |

|  | R-group | |
|---|---|---|
| Structure | Divalent linking group | Chelating group |
| (B) | (2) | desferrioxamine-p-SCN |
| (B) | (3) | DOTA-NHS |
| (B) | (3) | p-SCN-Bn-NOTA |
| (B) | (3) | p-SCN-Bn-PCTA |
| (B) | (3) | p-SCN-Bn-Oxo-DO3A |
| (B) | (3) | desferrioxamine-p-SCN |
| (C) | (1) | DOTA-NHS |
| (C) | (1) | p-SCN-Bn-NOTA |
| (C) | (1) | p-SCN-Bn-PCTA |
| (C) | (1) | p-SCN-Bn-Oxo-DO3A |
| (C) | (1) | desferrioxamine-p-SCN |
| (C) | (2) | DOTA-NHS |
| (C) | (2) | p-SCN-Bn-NOTA |
| (C) | (2) | p-SCN-Bn-PCTA |
| (C) | (2) | p-SCN-Bn-Oxo-DO3A |
| (C) | (2) | desferrioxamine-p-SCN |
| (C) | (3) | DOTA-NHS |
| (C) | (3) | p-SCN-Bn-NOTA |
| (C) | (3) | p-SCN-Bn-PCTA |
| (C) | (3) | p-SCN-Bn-Oxo-DO3A |
| (C) | (3) | desferrioxamine-p-SCN |
| (A) | (4) | DOTA-NHS |
| (A) | (4) | p-SCN-Bn-NOTA |
| (A) | (4) | p-SCN-Bn-PCTA |
| (A) | (4) | p-SCN-Bn-Oxo-DO3A |
| (A) | (4) | desferrioxamine-p-SCN |
| (B) | (4) | DOTA-NHS |
| (B) | (4) | p-SCN-Bn-NOTA |
| (B) | (4) | p-SCN-Bn-PCTA |
| (B) | (4) | p-SCN-Bn-Oxo-DO3A |
| (B) | (4) | desferrioxamine-p-SCN |
| (C) | (4) | DOTA-NHS |
| (C) | (4) | p-SCN-Bn-NOTA |
| (C) | (4) | p-SCN-Bn-PCTA |
| (C) | (4) | p-SCN-Bn-Oxo-DO3A |
| (C) | (4) | desferrioxamine-p-SCN |
| (A) | (5) | DOTA-NHS |
| (A) | (5) | p-SCN-Bn-NOTA |
| (A) | (5) | p-SCN-Bn-PCTA |
| (A) | (5) | p-SCN-Bn-Oxo-DO3A |
| (A) | (5) | desferrioxamine-p-SCN |
| (B) | (5) | DOTA-NHS |
| (B) | (5) | p-SCN-Bn-NOTA |
| (B) | (5) | p-SCN-Bn-PCTA |
| (B) | (5) | p-SCN-Bn-Oxo-DO3A |
| (B) | (5) | desferrioxamine-p-SCN |
| (C) | (5) | DOTA-NHS |
| (C) | (5) | p-SCN-Bn-NOTA |
| (C) | (5) | p-SCN-Bn-PCTA |
| (C) | (5) | p-SCN-Bn-Oxo-DO3A |
| (C) | (5) | desferrioxamine-p-SCN |
| (A) | (6) | DOTA-NHS |
| (A) | (6) | p-SCN-Bn-NOTA |
| (A) | (6) | p-SCN-Bn-PCTA |
| (A) | (6) | p-SCN-Bn-Oxo-DO3A |
| (A) | (6) | desferrioxamine-p-SCN |
| (B) | (6) | DOTA-NHS |
| (B) | (6) | p-SCN-Bn-NOTA |
| (B) | (6) | p-SCN-Bn-PCTA |
| (B) | (6) | p-SCN-Bn-Oxo-DO3A |
| (B) | (6) | desferrioxamine-p-SCN |
| (C) | (6) | DOTA-NHS |
| (C) | (6) | p-SCN-Bn-NOTA |
| (C) | (6) | p-SCN-Bn-PCTA |
| (C) | (6) | p-SCN-Bn-Oxo-DO3A |
| (C) | (6) | desferrioxamine-p-SCN |
| (A) | (7) | DOTA-NHS |
| (A) | (7) | p-SCN-Bn-NOTA |
| (A) | (7) | p-SCN-Bn-PCTA |
| (A) | (7) | p-SCN-Bn-Oxo-DO3A |
| (A) | (7) | desferrioxamine-p-SCN |
| (B) | (7) | DOTA-NHS |
| (B) | (7) | p-SCN-Bn-NOTA |
| (B) | (7) | p-SCN-Bn-PCTA |
| (B) | (7) | p-SCN-Bn-Oxo-DO3A |
| (B) | (7) | desferrioxamine-p-SCN |
| (C) | (7) | DOTA-NHS |
| (C) | (7) | p-SCN-Bn-NOTA |
| (C) | (7) | p-SCN-Bn-PCTA |
| (C) | (7) | p-SCN-Bn-Oxo-DO3A |
| (C) | (7) | desferrioxamine-p-SCN |
| (A) | (8) | DOTA-NHS |
| (A) | (8) | p-SCN-Bn-NOTA |
| (A) | (8) | p-SCN-Bn-PCTA |
| (A) | (8) | p-SCN-Bn-Oxo-DO3A |
| (A) | (8) | desferrioxamine-p-SCN |
| (B) | (8) | DOTA-NHS |
| (B) | (8) | p-SCN-Bn-NOTA |
| (B) | (8) | p-SCN-Bn-PCTA |
| (B) | (8) | p-SCN-Bn-Oxo-DO3A |
| (B) | (8) | desferrioxamine-p-SCN |
| (C) | (8) | DOTA-NHS |
| (C) | (8) | p-SCN-Bn-NOTA |
| (C) | (8) | p-SCN-Bn-PCTA |
| (C) | (8) | p-SCN-Bn-Oxo-DO3A |
| (C) | (8) | desferrioxamine-p-SCN |
| (A) | (9) | DOTA-NHS |
| (A) | (9) | p-SCN-Bn-NOTA |
| (A) | (9) | p-SCN-Bn-PCTA |
| (A) | (9) | p-SCN-Bn-Oxo-DO3A |
| (A) | (9) | desferrioxamine-p-SCN |
| (B) | (9) | DOTA-NHS |
| (B) | (9) | p-SCN-Bn-NOTA |
| (B) | (9) | p-SCN-Bn-PCTA |

| Structure | Divalent linking group | Chelating group |
|---|---|---|
| (B) | (9) | p-SCN-Bn-Oxo-DO3A |
| (B) | (9) | desferrioxamine-p-SCN |
| (C) | (9) | DOTA-NHS |
| (C) | (9) | p-SCN-Bn-NOTA |
| (C) | (9) | p-SCN-Bn-PCTA |
| (C) | (9) | p-SCN-Bn-Oxo-DO3A |
| (C) | (9) | desferrioxamine-p-SCN |
| (A) | (10) | DOTA-NHS |
| (A) | (10) | p-SCN-Bn-NOTA |
| (A) | (10) | p-SCN-Bn-PCTA |
| (A) | (10) | p-SCN-Bn-Oxo-DO3A |
| (A) | (10) | desferrioxamine-p-SCN |
| (B) | (10) | DOTA-NHS |
| (B) | (10) | p-SCN-Bn-NOTA |
| (B) | (10) | p-SCN-Bn-PCTA |
| (B) | (10) | p-SCN-Bn-Oxo-DO3A |
| (B) | (10) | desferrioxamine-p-SCN |
| (C) | (10) | DOTA-NHS |
| (C) | (10) | p-SCN-Bn-NOTA |
| (C) | (10) | p-SCN-Bn-PCTA |
| (C) | (10) | p-SCN-Bn-Oxo-DO3A |
| (C) | (10) | desferrioxamine-p-SCN |
| (A) | (11) | DOTA-NHS |
| (A) | (11) | p-SCN-Bn-NOTA |
| (A) | (11) | p-SCN-Bn-PCTA |
| (A) | (11) | p-SCN-Bn-Oxo-DO3A |
| (A) | (11) | desferrioxamine-p-SCN |
| (B) | (11) | DOTA-NHS |
| (B) | (11) | p-SCN-Bn-NOTA |
| (B) | (11) | p-SCN-Bn-PCTA |
| (B) | (11) | p-SCN-Bn-Oxo-DO3A |
| (B) | (11) | desferrioxamine-p-SCN |
| (C) | (11) | DOTA-NHS |
| (C) | (11) | p-SCN-Bn-NOTA |
| (C) | (11) | p-SCN-Bn-PCTA |
| (C) | (11) | p-SCN-Bn-Oxo-DO3A |
| (C) | (11) | desferrioxamine-p-SCN |
| (A) | (12) | DOTA-NHS |
| (A) | (12) | p-SCN-Bn-NOTA |
| (A) | (12) | p-SCN-Bn-PCTA |
| (A) | (12) | p-SCN-Bn-Oxo-DO3A |
| (A) | (12) | desferrioxamine-p-SCN |
| (B) | (12) | DOTA-NHS |
| (B) | (12) | p-SCN-Bn-NOTA |
| (B) | (12) | p-SCN-Bn-PCTA |
| (B) | (12) | p-SCN-Bn-Oxo-DO3A |
| (B) | (12) | desferrioxamine-p-SCN |
| (C) | (12) | DOTA-NHS |
| (C) | (12) | p-SCN-Bn-NOTA |
| (C) | (12) | p-SCN-Bn-PCTA |
| (C) | (12) | p-SCN-Bn-Oxo-DO3A |
| (C) | (12) | desferrioxamine-p-SCN |
| (A) | (13) | DOTA-NHS |
| (A) | (13) | p-SCN-Bn-NOTA |
| (A) | (13) | p-SCN-Bn-PCTA |
| (A) | (13) | p-SCN-Bn-Oxo-DO3A |
| (A) | (13) | desferrioxamine-p-SCN |
| (B) | (13) | DOTA-NHS |
| (B) | (13) | p-SCN-Bn-NOTA |
| (B) | (13) | p-SCN-Bn-PCTA |
| (B) | (13) | p-SCN-Bn-Oxo-DO3A |
| (B) | (13) | desferrioxamine-p-SCN |
| (C) | (13) | DOTA-NHS |
| (C) | (13) | p-SCN-Bn-NOTA |
| (C) | (13) | p-SCN-Bn-PCTA |
| (C) | (13) | p-SCN-Bn-Oxo-DO3A |
| (C) | (13) | desferrioxamine-p-SCN |
| (A) | (14) | DOTA-NHS |
| (A) | (14) | p-SCN-Bn-NOTA |
| (A) | (14) | p-SCN-Bn-PCTA |
| (A) | (14) | p-SCN-Bn-Oxo-DO3A |
| (A) | (14) | desferrioxamine-p-SCN |
| (B) | (14) | DOTA-NHS |
| (B) | (14) | p-SCN-Bn-NOTA |
| (B) | (14) | p-SCN-Bn-PCTA |
| (B) | (14) | p-SCN-Bn-Oxo-DO3A |
| (B) | (14) | desferrioxamine-p-SCN |
| (C) | (14) | DOTA-NHS |
| (C) | (14) | p-SCN-Bn-NOTA |
| (C) | (14) | p-SCN-Bn-PCTA |
| (C) | (14) | p-SCN-Bn-Oxo-DO3A |
| (C) | (14) | desferrioxamine-p-SCN |
| (A) | (1) | DOTA |
| (A) | (2) | DOTA |
| (A) | (3) | DOTA |
| (A) | (4) | DOTA |
| (A) | (5) | DOTA |
| (A) | (6) | DOTA |
| (A) | (7) | DOTA |
| (A) | (8) | DOTA |
| (A) | (9) | DOTA |
| (A) | (10) | DOTA |
| (A) | (11) | DOTA |
| (A) | (12) | DOTA |
| (A) | (13) | DOTA |
| (A) | (14) | DOTA |
| (A) | (15) | DOTA |
| (B) | (1) | DOTA |
| (B) | (2) | DOTA |
| (B) | (3) | DOTA |
| (B) | (4) | DOTA |
| (B) | (5) | DOTA |
| (B) | (6) | DOTA |
| (B) | (7) | DOTA |
| (B) | (8) | DOTA |
| (B) | (9) | DOTA |
| (B) | (10) | DOTA |
| (B) | (11) | DOTA |
| (B) | (12) | DOTA |
| (B) | (13) | DOTA |
| (B) | (14) | DOTA |

| Structure | Divalent linking group | Chelating group |
|---|---|---|
| (B) | (15) | DOTA |
| (C) | (1) | DOTA |
| (C) | (2) | DOTA |
| (C) | (3) | DOTA |
| (C) | (4) | DOTA |
| (C) | (5) | DOTA |
| (C) | (6) | DOTA |
| (C) | (7) | DOTA |
| (C) | (8) | DOTA |
| (C) | (9) | DOTA |
| (C) | (10) | DOTA |
| (C) | (11) | DOTA |
| (C) | (12) | DOTA |
| (C) | (13) | DOTA |
| (C) | (14) | DOTA |
| (C) | (15) | DOTA |
| (A) | (1) | DTPA |
| (A) | (2) | DTPA |
| (A) | (3) | DTPA |
| (A) | (4) | DTPA |
| (A) | (5) | DTPA |
| (A) | (6) | DTPA |
| (A) | (7) | DTPA |
| (A) | (8) | DTPA |
| (A) | (9) | DTPA |
| (A) | (10) | DTPA |
| (A) | (11) | DTPA |
| (A) | (12) | DTPA |
| (A) | (13) | DTPA |
| (A) | (14) | DTPA |
| (A) | (15) | DTPA |
| (B) | (1) | DTPA |
| (B) | (2) | DTPA |
| (B) | (3) | DTPA |
| (B) | (4) | DTPA |
| (B) | (5) | DTPA |
| (B) | (6) | DTPA |
| (B) | (7) | DTPA |
| (B) | (8) | DTPA |
| (B) | (9) | DTPA |
| (B) | (10) | DTPA |
| (B) | (11) | DTPA |
| (B) | (12) | DTPA |
| (B) | (13) | DTPA |
| (B) | (14) | DTPA |
| (B) | (15) | DTPA |
| (C) | (1) | DTPA |
| (C) | (2) | DTPA |
| (C) | (3) | DTPA |
| (C) | (4) | DTPA |
| (C) | (5) | DTPA |
| (C) | (6) | DTPA |
| (C) | (7) | DTPA |
| (C) | (8) | DTPA |
| (C) | (9) | DTPA |
| (C) | (10) | DTPA |
| (C) | (11) | DTPA |
| (C) | (12) | DTPA |
| (C) | (13) | DTPA |
| (C) | (14) | DTPA |
| (C) | (15) | DTPA |
| (A) | (1) | TETA |
| (A) | (2) | TETA |
| (A) | (3) | TETA |
| (A) | (4) | TETA |
| (A) | (5) | TETA |
| (A) | (6) | TETA |
| (A) | (7) | TETA |
| (A) | (8) | TETA |
| (A) | (9) | TETA |
| (A) | (10) | TETA |
| (A) | (11) | TETA |
| (A) | (12) | TETA |
| (A) | (13) | TETA |
| (A) | (14) | TETA |
| (A) | (15) | TETA |
| (B) | (1) | TETA |
| (B) | (2) | TETA |
| (B) | (3) | TETA |
| (B) | (4) | TETA |
| (B) | (5) | TETA |
| (B) | (6) | TETA |
| (B) | (7) | TETA |
| (B) | (8) | TETA |
| (B) | (9) | TETA |
| (B) | (10) | TETA |
| (B) | (11) | TETA |
| (B) | (12) | TETA |
| (B) | (13) | TETA |
| (B) | (14) | TETA |
| (B) | (15) | TETA |
| (C) | (1) | TETA |
| (C) | (2) | TETA |
| (C) | (3) | TETA |
| (C) | (4) | TETA |
| (C) | (5) | TETA |
| (C) | (6) | TETA |
| (C) | (7) | TETA |
| (C) | (8) | TETA |
| (C) | (9) | TETA |
| (C) | (10) | TETA |
| (C) | (11) | TETA |
| (C) | (12) | TETA |
| (C) | (13) | TETA |
| (C) | (14) | TETA |
| (C) | (15) | TETA |
| (A) | (15) | DOTA-NHS |
| (A) | (15) | p-SCN-Bn-NOTA |
| (A) | (15) | p-SCN-Bn-PCTA |
| (A) | (15) | p-SCN-Bn-Oxo-DO3A |
| (A) | (15) | desferrioxamine-p-SCN |
| (B) | (15) | DOTA-NHS |
| (B) | (15) | p-SCN-Bn-NOTA |
| (B) | (15) | p-SCN-Bn-PCTA |
| (B) | (15) | p-SCN-Bn-Oxo-DO3A |
| (B) | (15) | desferrioxamine-p-SCN |
| (C) | (15) | DOTA-NHS |
| (C) | (15) | p-SCN-Bn-NOTA |
| (C) | (15) | p-SCN-Bn-PCTA |
| (C) | (15) | p-SCN-Bn-Oxo-DO3A |
| (C) | (15) | desferrioxamine-p-SCN |

In each of the preceding compounds, the (*) end of the divalent linking group is connected with the chelating group through the —NCS group as is familiar to those skilled in the art. For example, where the (*) end of the divalent linking group is an oxygen, then a thiocarbamate group (—OC(S)N(H)—) connects the linking group to the chelating group. Similarly, where the (*) end of the divalent linking group is an —N(H)— group, then a thiourea group (—N(H)C(S)N(H)—) connects the linking group to the chelating group. One skilled in the art can readily envision the chemical linkages formed by each of the preceding divalent linking groups and the chelating group.

In other examples, the chelating group can comprise one of the following functional groups which can connect with the (*) end of the divalent linking group as is familiar to those skilled in the art:

| Reactive group on chelator | Group connecting Chelating and Linking Groups |
|---|---|
| —C(O)OH | —C(O)O— or —C(O)N(H)— |
| —C(O)OA | |
| —C(O)X | |
| —C(S)OH | —C(S)O— or —C(S)N(H)— |
| —C(S)OA | |
| —C(S)X | |
| —NCS | —N(H)C(S)O— or —N(H)C(S)N(H)— |
| —NCO | —N(H)C(O)O— or —N(H)C(O)N(H)— | where X is a halogen and —OA is an activated ester group, such as but not limited to N-hydroxysuccinimidyl (NHS) or 4-nitrophenoxy.

That is, for example, the compounds can be of the formula,

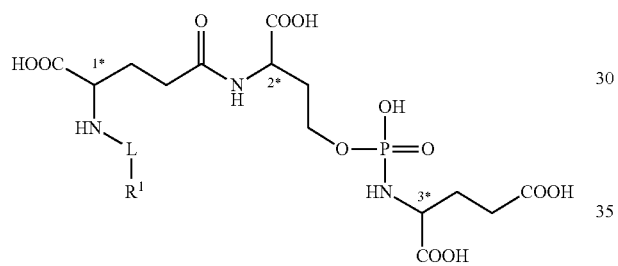

or a pharmaceutically acceptable salt thereof, wherein
n is 0 or greater (e.g., 0-10 or 0-6 or 0-5 or 0-4 or 0-3 or 0, 1, or 2); and
L is the divalent linking group; and
$R^1$ is the chelating agent, wherein the chelating agent is optionally associated with a PET-active radioisotope.

In another example, the compounds can be of the formula,

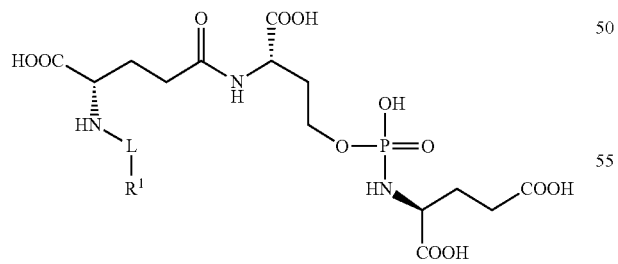

or a pharmaceutically acceptable salt thereof, wherein
n is 0 or greater (e.g., 0-10 or 0-6 or 0-5 or 0-4 or 0-3 or 0, 1, or 2); and
L is the divalent linking group; and
$R^1$ is the chelating agent, wherein the chelating agent is optionally associated with a PET-active radioisotope.

In the foregoing structure, 1*, 2*, and 3* are chiral centers that are independently racemic (rac) or in the S or R stereoconfiguration. Thus, compounds according to this aspect include those with the combinations of stereoconfigurations in FIG. 7, and combinations thereof.

For example, $R^1$ can be DOTA, bonded through any of its four carboxylic acid groups:

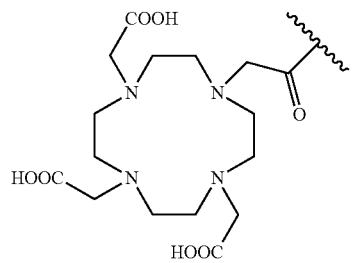

In another example, $R^1$ can be

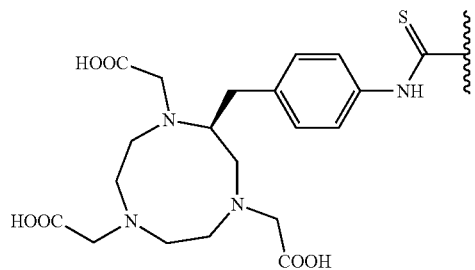

In another example, $R^1$ can be

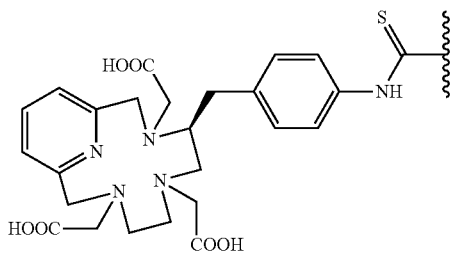 [SMILES: *C(=S)Nc1ccc(C[C@H]2CN(CC(=O)O)CCN(CC(=O)O)Cc3cccc(n3)CN2CC(=O)O)cc1]

In another example, $R^1$ can be

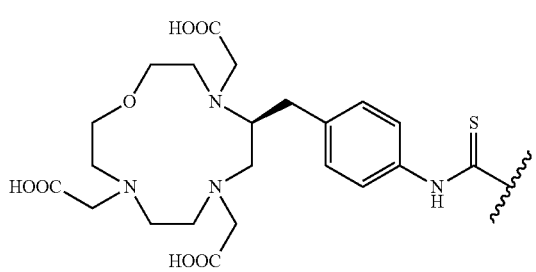 [SMILES: *C(=S)Nc1ccc(C[C@H]2CN(CC(=O)O)CCN(CC(=O)O)CCOCCN2CC(=O)O)cc1]

In another example, $R^1$ can be

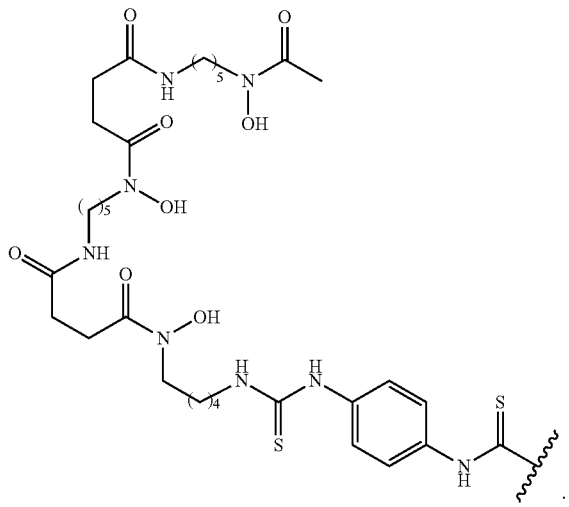

In another example, $R^1$ can be

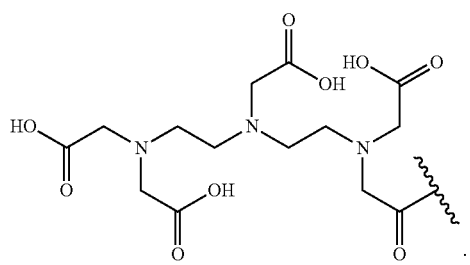 [SMILES: *C(=O)CN(CCN(CCN(CC(=O)O)CC(=O)O)CC(=O)O)CC(=O)O]

In another example, $R^1$ can be

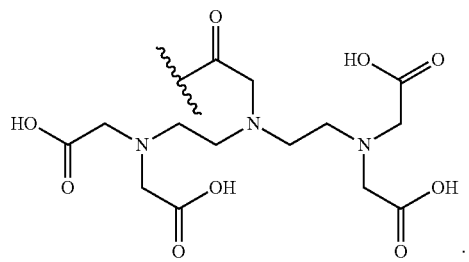 [SMILES: *C(=O)CN(CCN(CC(=O)O)CC(=O)O)CCN(CC(=O)O)CC(=O)O]

In another example, $R^1$ can be

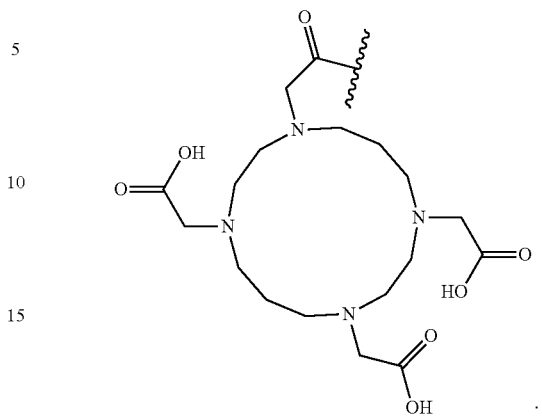

Each of the preceding compounds may be chelated with a radioisotope selected from $^{68}$Ga, $^{64}$Cu, $^{89}$Zr, $^{186/188}$Re, $^{90}$Y, $^{177}$Lu, $^{153}$Sm, $^{213}$Bi, $^{225}$Ac, and $^{223}$Ra.

In certain embodiments, each of the preceding compounds may be chelated with a radioisotope that is $^{89}$Zr.

In certain embodiments, each of the preceding compounds may be chelated with a radioisotope that is $^{64}$Cu.

In certain embodiments, each of the preceding compounds may be chelated with a radioisotope that is with $^{68}$Ga.

In certain embodiments, each of the preceding compounds may be chelated with a radioisotope that is $^{186/188}$Re.

In certain embodiments, each of the preceding compounds may be chelated with a radioisotope that is $^{90}$Y.

In certain embodiments, each of the preceding compounds may be chelated with a radioisotope that is $^{177}$Lu.

In certain embodiments, each of the preceding compounds may be chelated with a radioisotope that is $^{153}$Sm.

In certain embodiments, each of the preceding compounds may be chelated with a radioisotope that is $^{213}$Bi.

In certain embodiments, each of the preceding compounds may be chelated with a radioisotope that is $^{225}$Ac.

In certain embodiments, each of the preceding compounds may be chelated with a radioisotope that is $^{223}$Ra.

In certain embodiments, the compound may be selected from the following, or a pharmaceutically acceptable salt thereof,

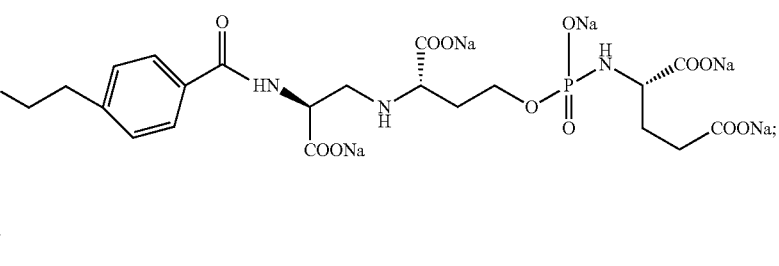

sodium (S)-2-(((((S)-3-carboxylato-3-((S)-4-carboxylato-4-(4-(2-(2-(4,7,10-tris(carboxylatomethyl)-1,4,7,10-tetraazacyclododecan-1-yl)acetamido)ethyl)benzamido)butanamido)propoxy)oxidophosphoryl)amino)pentanedioate -continued

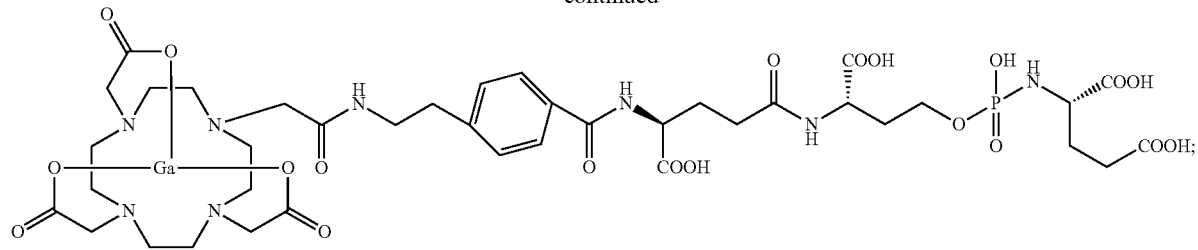

gallium 2,2′,2″-(10-(2-((4-(((1S)-1-carboxy-4-(((1S)-1-carboxy-3-(((((S)-1,3-dicarboxypropyl)amino)(hydroxy)phoxphoryl)oxy)propyl)amino)-4-oxobutyl)carbamoyl)phenethyl)amino)-2-oxoethyl)-1,4,7,10-tetraazacyclododecane-1,4,7-triyl)triacetate

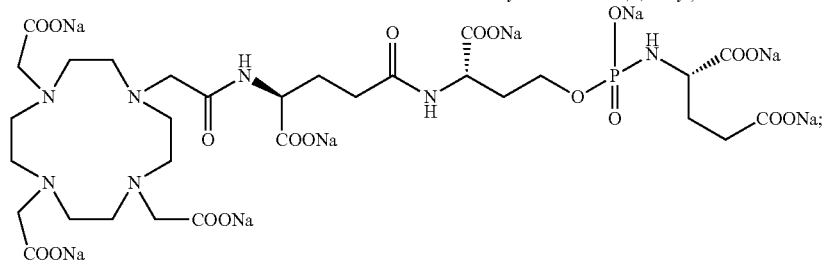

sodium (S)-2-(((((S)-3-carboxylato-3-((S)-4-carboxylato-4-(2-(4,7,10-tris(carboxylatomethyl)-1,4,7,10-tetraazacyclododecan-1-yl)acetamido)butanamido)propoxy)oxidophosphoryl)amino)pentanedioate

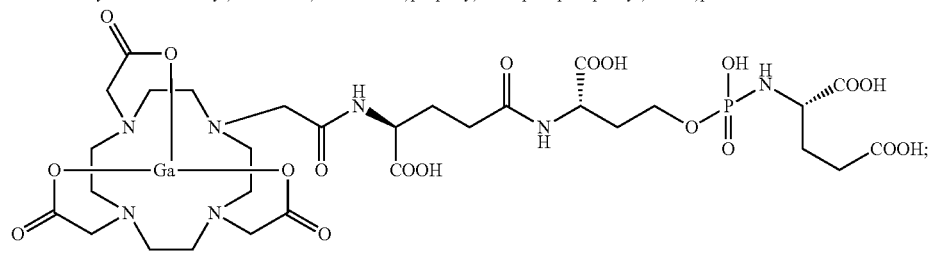

gallium 2,2′,2″-(10-(2-(((1S)-1-carboxy-4-(((1S)-1-carboxy-3-(((((S)-1,3-dicarboxypropyl)amino)(hydroxy)phoxphoryl)oxy)propyl)amino)-4-oxobutyl)amino)-2-oxoethyl)-1,4,7,10-tetraazacyclododecane-1,4,7-triyl)triacetate

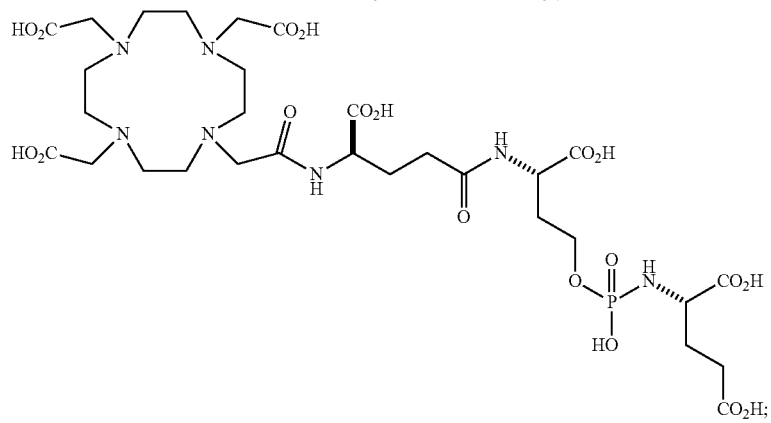

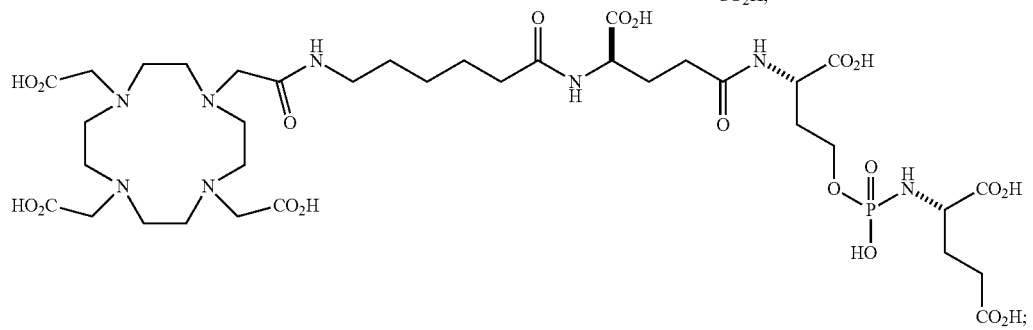

-continued

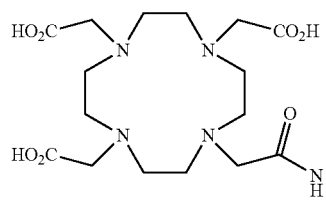
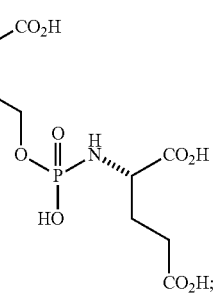

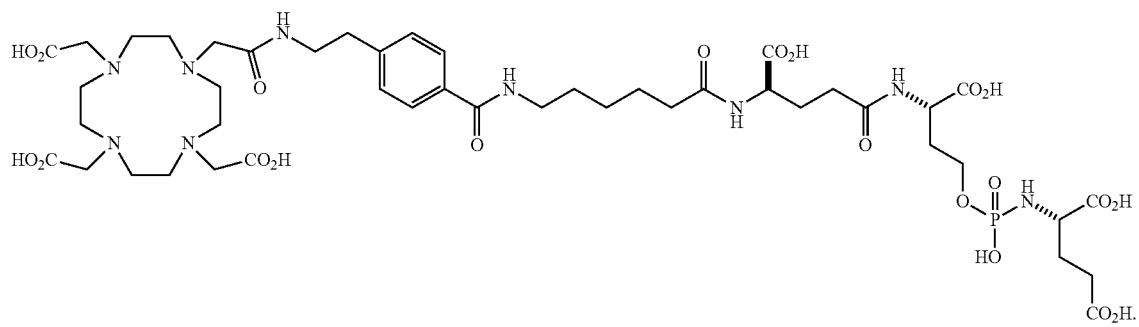

The chelates may possess one or more of the following characteristics (8, 9):
high labeling efficiency: chelated incorporation of $^{68}$Ga at greater than 60% (decay corrected), high overall yield: final purified compound >40% overall yield (decay corrected) based on starting $^{68}$Ga ion
high specific activity: >500 Ci/mmol measured by HPLC
high stability: >90% labeled compound remaining up to 6 hours after preparation.
high inhibitory potency ($IC_{50}$<10 nM) for PSMA (the $IC_{50}$ for the prototype SFB-CTT-54 is 0.7 nM)
irreversible or slowly-reversible inhibition of PSMA specific binding to the LNCaP cells and minimal binding to the PC3 cells (LNCaP uptake should be >2 fold the PC3 uptake and blocked by CTT-54 or 2-PMPA.
high saline and ex vivo stability: >90% stable in saline and blood for up to 3 h at room temperature.

The preceding chelates may be prepared according to solution phase or solid phase methods familiar to those skilled in the art.

In one aspect, the disclosure provides solid phase synthetic methods for preparing a compound according to the formula,

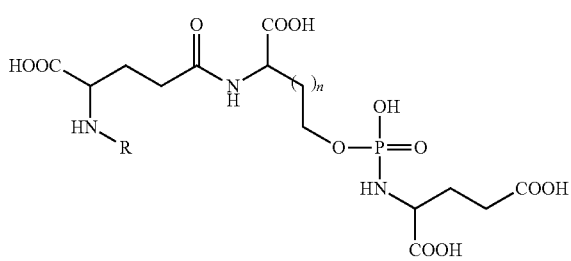

or a pharmaceutically acceptable salt thereof, wherein n and R are as defined according to any of the preceding aspects and embodiments thereof, comprising the steps of, providing a compound of the formula,

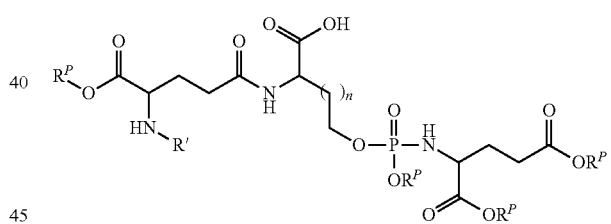

wherein
n is 0 or greater (e.g., as defined above);
R' is an optionally protected chelating group; and
each $R^p$ is independently a protecting group;
and
when R' is an unprotected chelating group,
optionally associating the chelating group of the compound with a PET-active radioisotope to provide a hot compound, and
removing the protecting groups from the hot compound; or
and when R' is a protected chelating group,
removing the protecting groups from the compound; and
optionally associating the chelating group of the deprotected compound with a PET-active radioisotope.

The preceding compound can be prepared by subjecting a first resin modified with a compound of the formula,

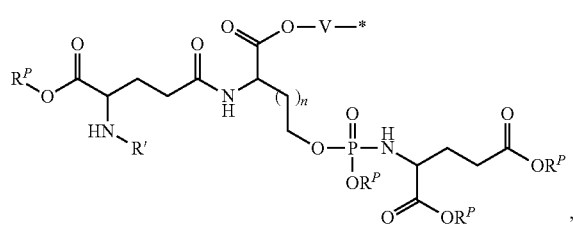

wherein
V is a divalent linking group, as defined above;
and *- indicates the point of attachment to the resin,
to conditions suitable for cleaving the compound of the formula,

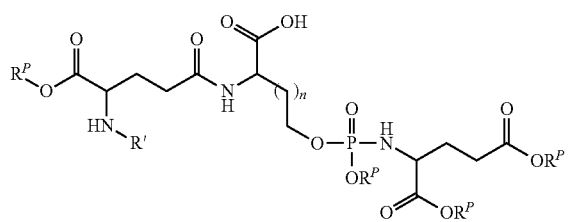

from the first resin,
when R' is an unprotected chelating group,
   optionally associating the chelating group of the cleaved compound with a PET-active radioisotope to provide a hot compound, and
   removing the protecting groups from the hot compound; or
and when R' is a protected chelating group,
   removing the protecting groups from the cleaved compound; and
   optionally associating the chelating group of the deprotected compound with a PET-active radioisotope.

A "protecting group" as used herein include, but are not limited to, optionally substituted benzyl, t-butyl ester, allyl ester, alkyl esters (e.g., methyl, ethyl), fluorenylmethoxycarbonyl groups (Fmoc), and amino, carboxylic acid and phosphorus acid protecting groups described in Greene's Protective Groups in Organic Synthesis, 4th Edition (the relevant parts of which are incorporated by reference).

Optionally benzyl groups include, but are not limited to, unsubstituted benzyl, triphenylmethyl (trityl), diphenylmethyl, o-nitrobenzyl, 2,4,6-trimethylbenzyl, p-bromobenzyl, p-nitrobenzyl, p-methoxybenzyl (PMB), 2,6-dimethoxybenzyl, 4-(methylsulfinyl)benzyl, 4-sulfobenzyl, 4-azidomethoxybenzyl, and piperonyl, and benzyl protecting groups for carboxylic and phosphorus acids disclosed in Greene's Protective Groups in Organic Synthesis (the relevant parts of which are incorporated by reference).

The resins used in the preceding method can be those generally used in the solid phase synthesis of peptides as are familiar in the art. For example, the resin, itself, may comprise poly(styrene), such as 1-2% divinylbenzene crosslinked poly(styrene) particles, or polyacrylamide, or polyethylene glycol (PEG).

Suitable conditions for cleaving the compound from the resin will depend on the nature of the compound being synthesized and the chemical linkage between the compound and the resin (i.e., "V" in the preceding formula. For example, where each of the following resins are used, the corresponding cleaving conditions may be used (where ⌇ indicates the bond to the resin):

| Resin | | Cleaving conditions |
|---|---|---|
| Merrifield resin | ⌇–C₆H₄–CH₂Cl | HF (scavengers), TFMSA, TMS—OTf, HBr/TFA, or H₂ |
| PAM resin | ⌇–C₆H₄–CH₂–NH–C(O)–CH₂–C₆H₄–CH₂–O–C(O)–CH(NH—Boc)–CH₃ | HF (scavengers), TFMSA, or TMS—OTf, |
| Brominated Wang resin | ⌇–C₆H₄–C(O)–CH(CH₃)–Br | Light (350 nm) |
| Kaiser resin | ⌇–C₆H₄–C(=NOH)–C₆H₄–NO₂ | NaOH |
| Wang resin | ⌇–C₆H₄–CH₂–O–C₆H₄–CH₂OH | HF (scavengers), |

-continued
| Resin | | Cleaving conditions |
|---|---|---|
| PHB resins | 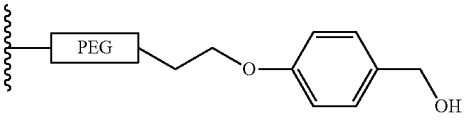 | HF (scavengers), |
| HMPA resins | 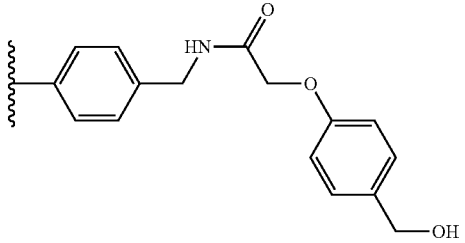 [SMILES: *c1ccc(CNC(=O)COc2ccc(CO)cc2)cc1] | HF (scavengers), |
| HMPB resins | 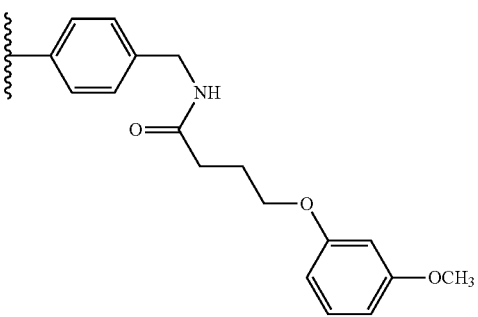 [SMILES: *c1ccc(CNC(=O)CCCOc2cccc(OC)c2)cc1] | Dilute TFA (1-5%) |
| 2-chlorotrityl resins | 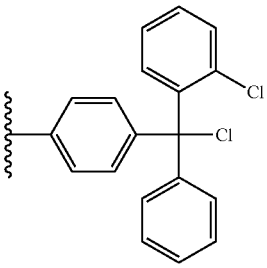 [SMILES: *c1ccc(C(Cl)(c2ccccc2)c2ccccc2Cl)cc1] | Acetic acid/TFE/DCM (1,8,8, v/v/v), HFIP/DCM (1,4 v/v), or 0.5% TFA in DCM |
| 4-carboxytrityl resins | 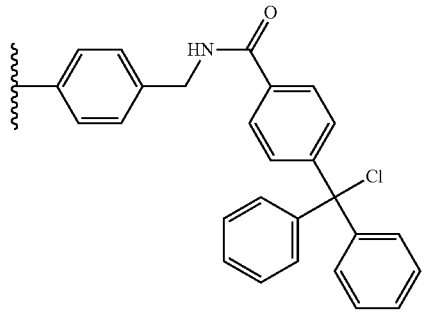 [SMILES: *c1ccc(CNC(=O)c2ccc(C(Cl)(c3ccccc3)c3ccccc3)cc2)cc1] | Acetic acid/TFE/DCM (1,8,8, v/v/v), HFIP/DCM (1,4 v/v), 0.5 TFA in DCM |
| Rink acid resin | 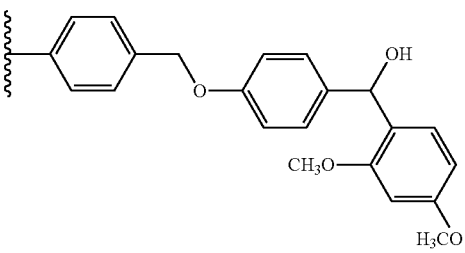 | Acetic acid/DCM (1,9 v/v), |

| Resin | | Cleaving conditions |
|---|---|---|
| HMBA resins | [structure: diphenyl(4-methylphenyl)methyl group attached to resin via NH-C(O)-C6H4-CH2OH] | NaOH |
| 4-sulfanoylbenzoyl resin | Resin—[structure: benzyl-NH-C(O)-C6H4-S(O)2-NH2] | 1. activation by CH₂N₂, TMS—CHN₂, or ICH₂CN<br>2. NaOH. | where TFMSA is trifluoromethanesulfonic acid;
DCM is dichloromethane;
TMS—OTf is trimethylsilyltrifluromethane sulfonate;
HFIP is hexafluoroisopropanol; and
TFE is 2,2,2-trifluoroethanol.

Where R' is an optionally protected chelating group, it may be protected with one or more of the preceding protecting groups as are familiar to those skilled in the art. For example R' can be the following, where the unprotected R' can be optionally associated with a PET-active radioisotope (e.g., $^{68}$Ga),

| Chelator | Protected Structure (R') | Unprotected Structure (R') |
|---|---|---|
| DOTA | [DOTA macrocycle with three $COOR^P$ arms and one $C(O)$-L linker] | [DOTA macrocycle with three COOH arms and one C(O)-L linker] |
| Bn-NOTA | [NOTA macrocycle with two $R^POOC$ arms, one $COOR^P$ arm, benzyl with NH-C(S)-L linker] | [NOTA macrocycle with two HOOC arms, one COOH arm, benzyl with NH-C(S)-L linker] |

| Chelator | Protected Structure (R') | Unprotected Structure (R') |
|---|---|---|
| Bn-PCTA | 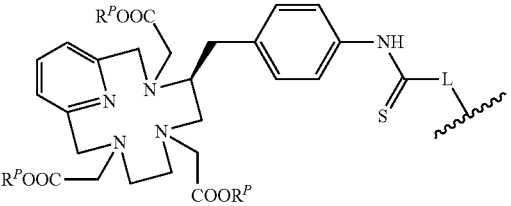 | 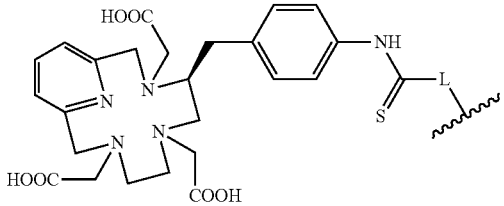 |
| Bn-Oxo-DO3A | 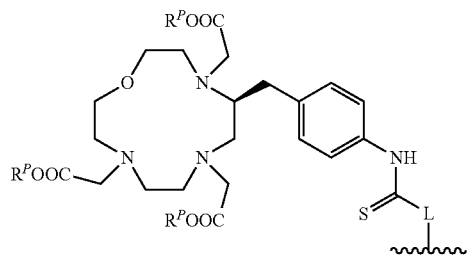 | 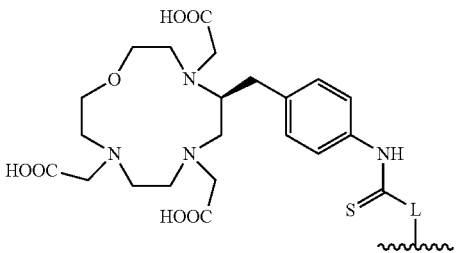 |
| desferri-oxamine | 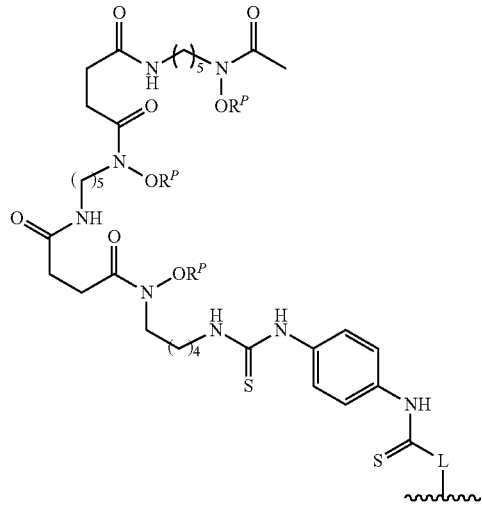 | 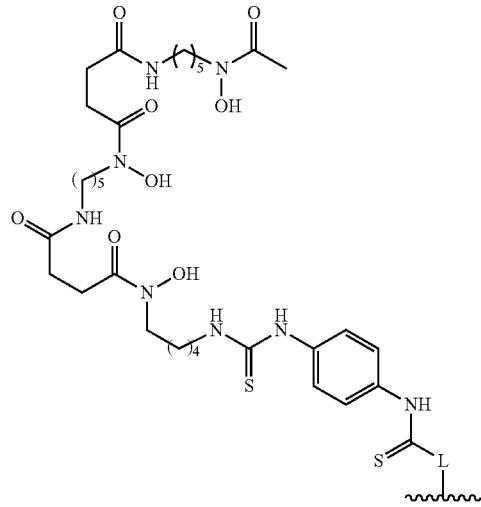 |
| Diethylene-triamine-pentaacetic acid (DTPA) | 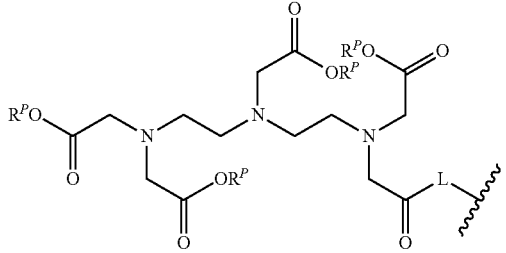 | 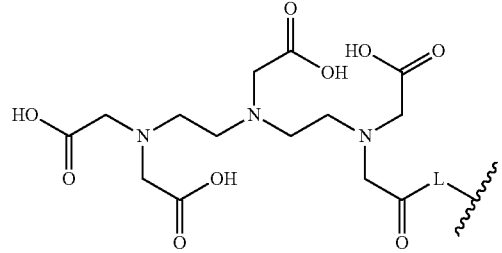 |

| Chelator | Protected Structure (R') | Unprotected Structure (R') |
|---|---|---|
| 1,4,8,11-tetraazacyclotetradecane 1,4,8,11-tetraacetic acid (TETA) | | |

As would be clear to one skilled in the art, removal of the $R^P$ groups in the preceding results in the formation of the corresponding compound wherein $R^P$ is hydrogen, or a salt thereof.

When $R^P$ is a t-butyl group, the method can be maintained under anhydrous conditions to prevent degradation of the compounds as the phosphoramidate moiety is known to be unstable in aqueous acidic media. In various embodiment, each of the following deprotection conditions can be utilized for removal of t-butyl groups:

i) Contacting the compound with an acid selected from the groups consisting of, trifluoroacetic acid, hydrochloric acid, formic acid, glacial acetic acid, chloroacetic acid, and mixtures thereof;

ii) Contacting the compound with an acid (selected as in (i)) in a solvent selected from the group consisting of diethyl ether, ethyl acetate, dioxane, 1,2-dichloroethane, dichloromethane, t-butanol, glyme, methyl t-butylether, tetrahydrofuran, and mixtures thereof;

iii) Contacting the compound with a neat acid;

iv) Contacting the compound any of the preceding with the addition of scavengers, such as, but not limited to triethylsilane (TES);

v) Contacting the compound as in any of the preceding at a temperatures between room temperature (e.g., 25° C.) and 180° C.;

vi) Contacting the compound as in any of the preceding with microwave heating;

vii) Contacting the compound with a base such as, but not limited to, NaOH;

viii) Contacting the compound as in any of the preceding, where the reaction is allowed to proceed for a period of time between about 15 seconds and 15 minutes;

ix) Contacting the compound with trimethylsilyl iodide (TMS-I, may be formed in situ from trimethylsilyl chloride and sodium iodide), x) Contacting the compound with trimethylsilyl triflate (TMSOTf) and triethylamine (TEA);

xi) Contacting the compound with quinoline at elevated temperatures, e.g., greater than 150° C., such as, 180° C.;

xii) Contacting the compound with LiI in ethyl acetate;

When $R^P$ is an optionally substituted benzyl group (e.g., unsubstituted benzyl), suitable deprotection conditions include, but are not limited to, hydrogenolysis conditions (e.g., $H_2$ and Pd/C) or catalytic hydrogen transfer using ammonium formate and Pd/C. Other hydrogenation catalysts may be used as are familiar to those skilled in the art.

In certain embodiments, alternative hydrogen sources may be used including, but not limited to ammonium formate, sodium formate, or formic acid with triethylamine. In certain embodiments, the hydrogen source is ammonium formate.

The hydrogenation may be undertake in a suitable solvent, selected from, but not limited to, ethanol, tetrahydrofuran, water, or phosphate buffered saline, or a mixture thereof.

For example, in certain embodiments, the deprotection can be setup in a cartridge where the Pd/C catalyst is loaded in a layer or distributed in inert material, then, the protected compound dissolved in a solvent (such as ethanol), is further dissolved in ammonium formate and flushed through the cartridge to yield deprotected material without the need for further purification.

In one embodiment of any of the preceding embodiments, the first resin is prepared by contacting a second resin modified with a compound of the formula,

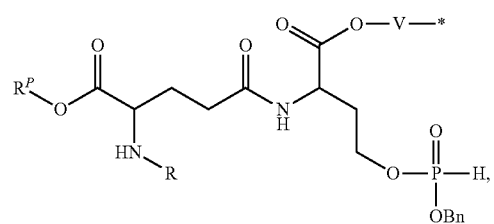

with a compound of the formula,

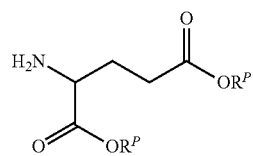

under conditions suitable to generate the first resin. Suitable conditions include, but are not limited to oxidative coupling conditions (e.g., CCl$_4$ or I$_2$ in an organic basic solution such as triethylamine in DCM).

In another embodiment, the second resin is prepared by sequentially contacting a third resin modified with a compound of the formula,

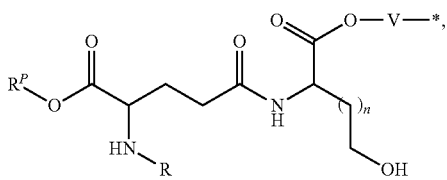

with dibenzyl phosphite and an optionally substituted benzyl alcohol under conditions suitable to generate the second resin. Suitable conditions include, but are not limited to transesterfication in dry pyridine solution.

In another embodiment, the third resin is prepared by contacting a fourth resin modified with a compound of the formula,

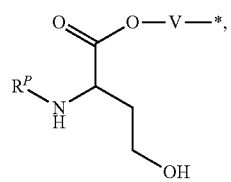

with a compound of the formula,

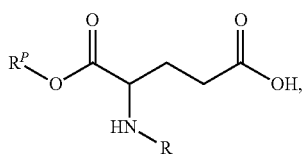

under conditions suitable to generate the third resin. Suitable conditions include, but are not limited to deprotecting the amino protecting group (R$^P$), optionally washing the resin, contacting the deprotected resin with the free acid compound dissolved in a solvent such as dimethylformamide (DMF) combined with a suitable amide coupling reagent.

Where the amino protecting group is a Boc group (tert-butyloxycarbonyl), the Boc group may be removed with acid, such as trifluoroacetic acid (TFA) followed by an optional wash with a solvent such as N,N-dimethylformamide (DMF). Where the amino protecting group is a 9-fluorenylmethyloxycarbonyl (Fmoc) group, the Fmoc may be removed by contacting the protected resin with a base, such as piperidine in a solvent, such as DMF Coupling agents include, but are not limited to dicyclohexylcarbodiimide (DCC), diisopropylcarbodiimide (DIC), 1-tert-Butyl-3-ethylcarbodiimide, N'-Di-tert-butylcarbodiimide, N-(3-Dimethylaminopropyl)-N'-ethylcarbodiimide, 1-[3-(Dimethylamino)propyl]-3-ethylcarbodiimide methiodide, 1,3-Di-p-tolylcarbodiimide, 1-hydroxy-benzotriazole (HOBt), 1-hydroxy-7-aza-benzotriazole (HOAt), O-(Benzotriazol-1-yl)-N,N,N',N'-tetramethyluronium hexafluorophosphate (HBTU), O-(7-Azabenzotriazol-1-yl)-N,N,N',N'-tetramethyluronium hexafluorophosphate (HATU), 2-(6-Chloro-1H-benzotriazole-1-yl)-1,1,3,3-tetramethylaminium hexafluorophosphate (HCTU) O-(Benzotriazol-1-yl)-N,N,N',N'-tetramethyluronium tetrafluoroborate (TBTU), benzotriazol-1-yl-oxytripyrrolidinophosphonium hexafluorophosphate (PyBOP), Ethyl (hydroxyimino)cyanoacetate (Oxyma), (1-Cyano-2-ethoxy-2-oxoethylidenaminooxy)dimethylamino-morpholino-carbenium hexafluorophosphate (COMU), and S-(1-Oxido-2-pyridyl)-N,N,N',N'-tetramethylthiuronium tetrafluoroborate (TOTT).

EXAMPLES

Example 1

Radiochemical purity of $^{99m}$Tc-DTPA-SCN-CTT-54 was determined to be greater than 95% as confirmed by HPLC. In vitro studies using PSMA(+) LNCaP cells and PSMA(−) PC3 cells confirmed the specificity of this radiolabeled bifunctional chelator-PSMA inhibitor conjugate for PSMA+ was preserved (FIG. 2). Furthermore, over 70% of these molecules associated with LNCaP cells were internalized within 30 min. Although the amount of uptake increases over time, the internalization is rapid for these agents.

Figure 3:
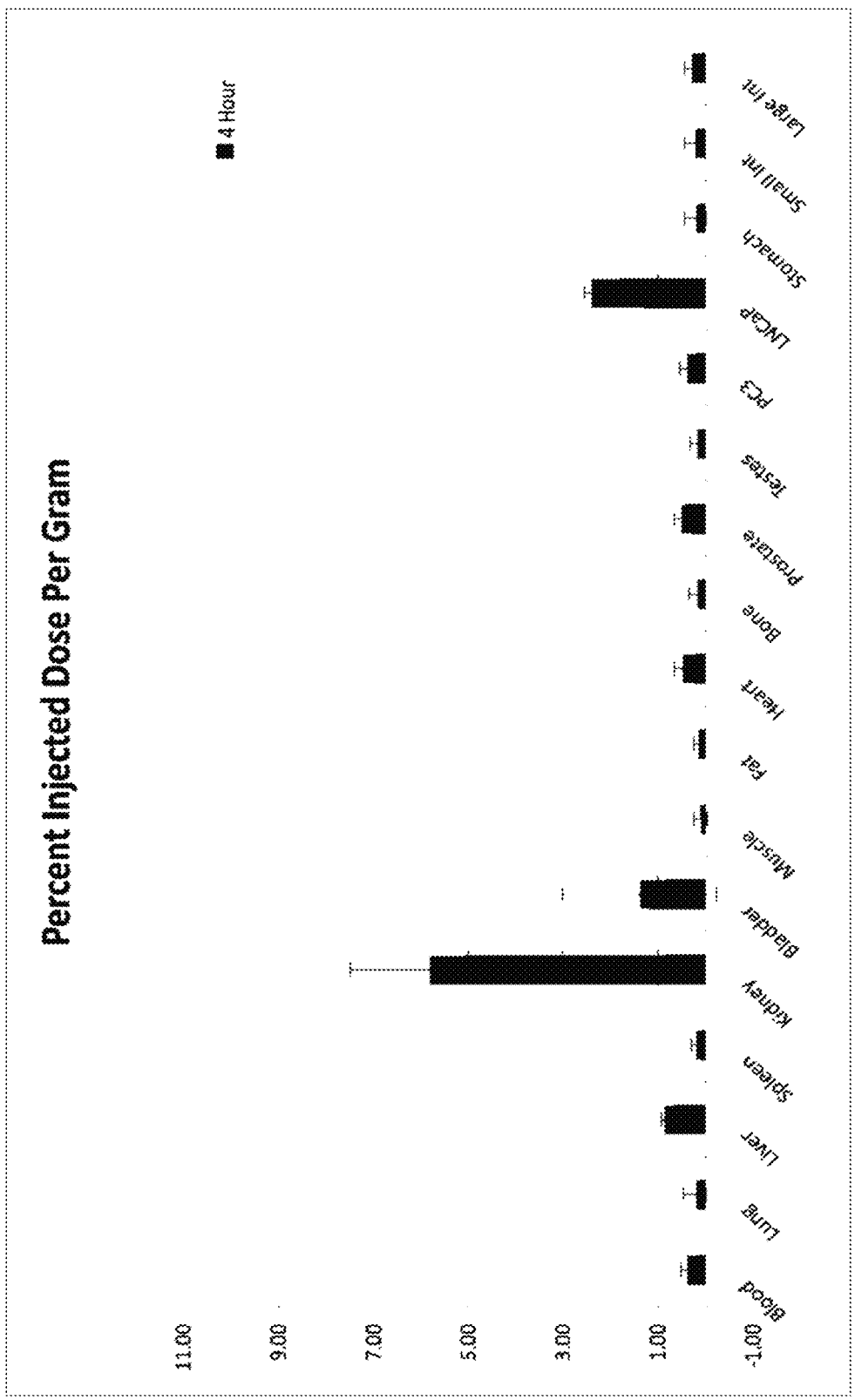
FIG. 3 Biodistribution of $^{99m}$Tc Radiolabeled PSMA Inhibitor.
Figure 4:
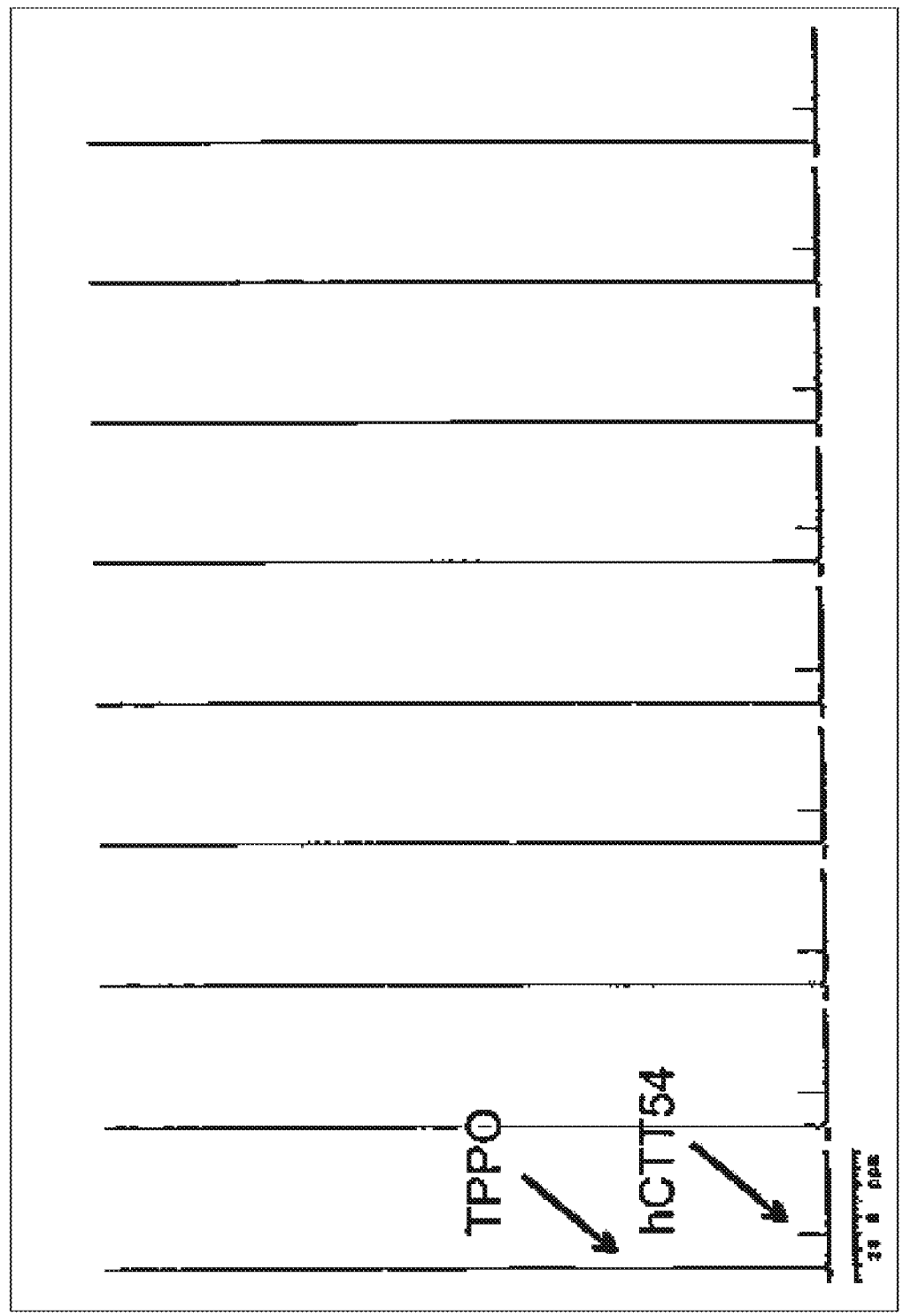
FIG. 4 $^{31}$P NMR spectra of hCTT54/CTT1000 at pH 4.5 each hour from 0-8 h. Triphenylphosphine oxide (TPPO) was used as an internal reference.
Figure 5:
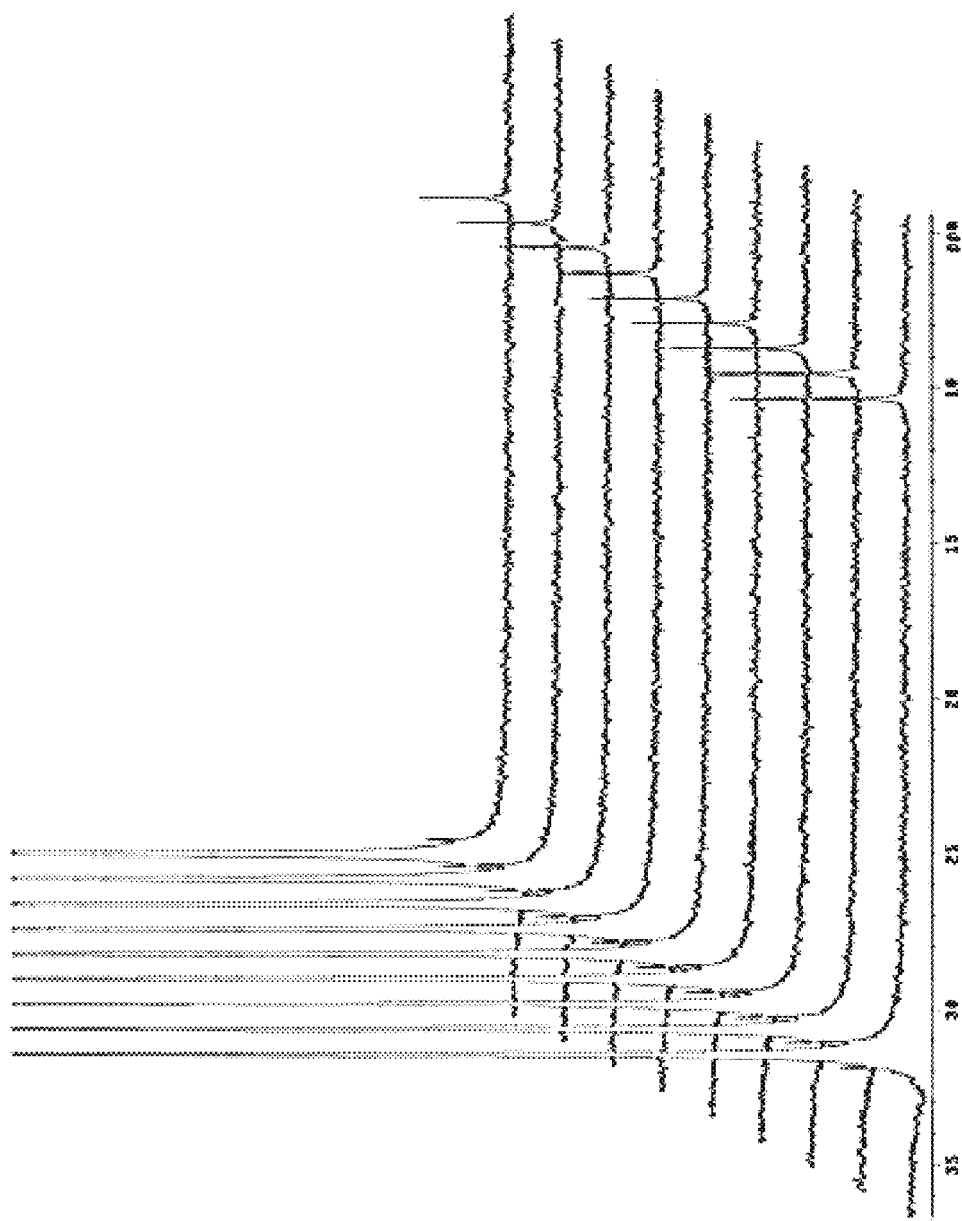
FIG. 5 $^{31}$P NMR spectra of TG97/CTT2000 at pH 3 each hour from 0-8 h. Triphenylphosphine oxide (TPPO) was used as an internal reference.

In biodistribution studies, we also confirmed the in vivo targeting of this $^{99m}$Tc-DTPA-SCN-CTT-54. Radiolabeled $^{99m}$Tc-(CO)$_3$-DTPA-LW-54, was injected via a tail vein into male nu/nu mice bearing both LNCaP (PSMA+) and PC3 (PSMA−) tumor xenografts and biodistribution data was collected at 2 and 4 hours. The data clearly demonstrates selective uptake in the LNCaP tumor while there is no detectable signal in the PC3 xenografts (data shown in FIG. 3 for the 4 h time point).

These data show that a bifunctional chelator can be successfully coupled to PSMA targeting inhibitor CTT-54 and that the resulting conjugate can be labeled with a metallic radionuclide using a post-labeling approach. The literature precedent for $^{64}$Cu, $^{68}$Ga, and $^{89}$Zr radio-labeling of the selected bifunctional chelators when coupled to other targeting agents through a post-labeling approach further supports the likelihood of success in the revised approach.

All of the proposed isotopes are available from commercial sources (e.g., $^{68}$Ga generator from IDB).

Suitable radioisotopes for use in the chelates herein include, but are not limited to, $^{64}$Cu, $^{68}$Ga, $^{89}$Zr, $^{186/188}$Re, $^{90}$Y, $^{177}$Lu, $^{153}$Sm, $^{213}$Bi, $^{225}$Ac, and $^{223}$Ra. These are particularly attractive isotopes due to their light metal properties and the ability to bind to chelating agents (1). As stated above, we have already achieved preliminary success with a chelated radiolabel on our PSMA inhibitor.

In certain examples, the labeling efficiency of the chelates herein can be greater than 60% (decay corrected) with any of the light metal isotopes with an overall yield greater than 40% (decay corrected). The specific activity may change slightly with each isotope, but only 2-3 fold depending on the isotope. Typically, 1-10 mCi of imaging agent is administered per patient.

Following administration of the chelated PSMA inhibitors herein, the imaging time may be altered to alter and/or optimize imaging characteristics. A recent paper by Pomper's laboratory (10) demonstrated the utility of a reversible PSMA inhibitor $^{68}$Ga-DOTA-urea based inhibitor in PET imaging of prostate cancer tumors in a mouse xenograft model. However, this is a sub-optimal reversible inhibitor that demonstrates decreased PET imaging as well as decreased tumor uptake over time. In comparison, uptake of the PSMA inhibitor, CTT-54, in the fraction associated with the tumor, continues to increase over time.

$^{68}$Ga has a relatively short half-life. As a result, timing between manufacture of the final imaging agent and use in animals or humans can be important. Since binding to tumors in the xenograft model is very rapid, imaging of the tumor can be performed well within an acceptable time frame.

The decay half-life of $^{64}$Cu and $^{89}$Zr are much longer (12.7 and 78.4 hours, respectively). The advantages are three-fold. First, the timing of imaging between manufacture of the final imaging agent and animal/human imaging is less important. Second, there can be additional time between injection of the imaging agent and the PET scan which will allow additional renal clearance of any unbound material and additional time for clearance from the kidneys, liver and bladder. Thirdly, the longer half-lives allow for longitudinal studies on a patient with a single injection of the imaging agent.

Presently, there are no current marketed commercial $^{89}$Zr/$^{64}$Cu/$^{68}$Ga labeled PET imaging agents for prostate cancer.

The PET market is the fastest growing segment of the nuclear imaging market (Chemical Engineering News Molecular Imaging Volume 83, Number 30 pp. 25-34).

The ease with which the $^{68}$Ga can be generated from a GMP commercially available source that can be stored for up to a year, may make this product more attractive than one which is dependent on proximity to a cyclotron. Commercial GMP sources for the generators exist, e.g. IDB markets an iThemba GMP 68 gallium generator. The parent isotope $^{68}$Ge has a half-life of 271 days and can be easily sent to hospitals within the generator, where it is storable for almost a year. The on-site generator is required to minimize the time losses since there will be pharmaceutical preparation time to attach the gallium-68 as a tracer to the pharmaceutical chelate molecules so that the total preparation time may approach the isotope half-life.

Example 2

Representative Preparation of DOTA Conjugates of PSMA Targeting Molecules

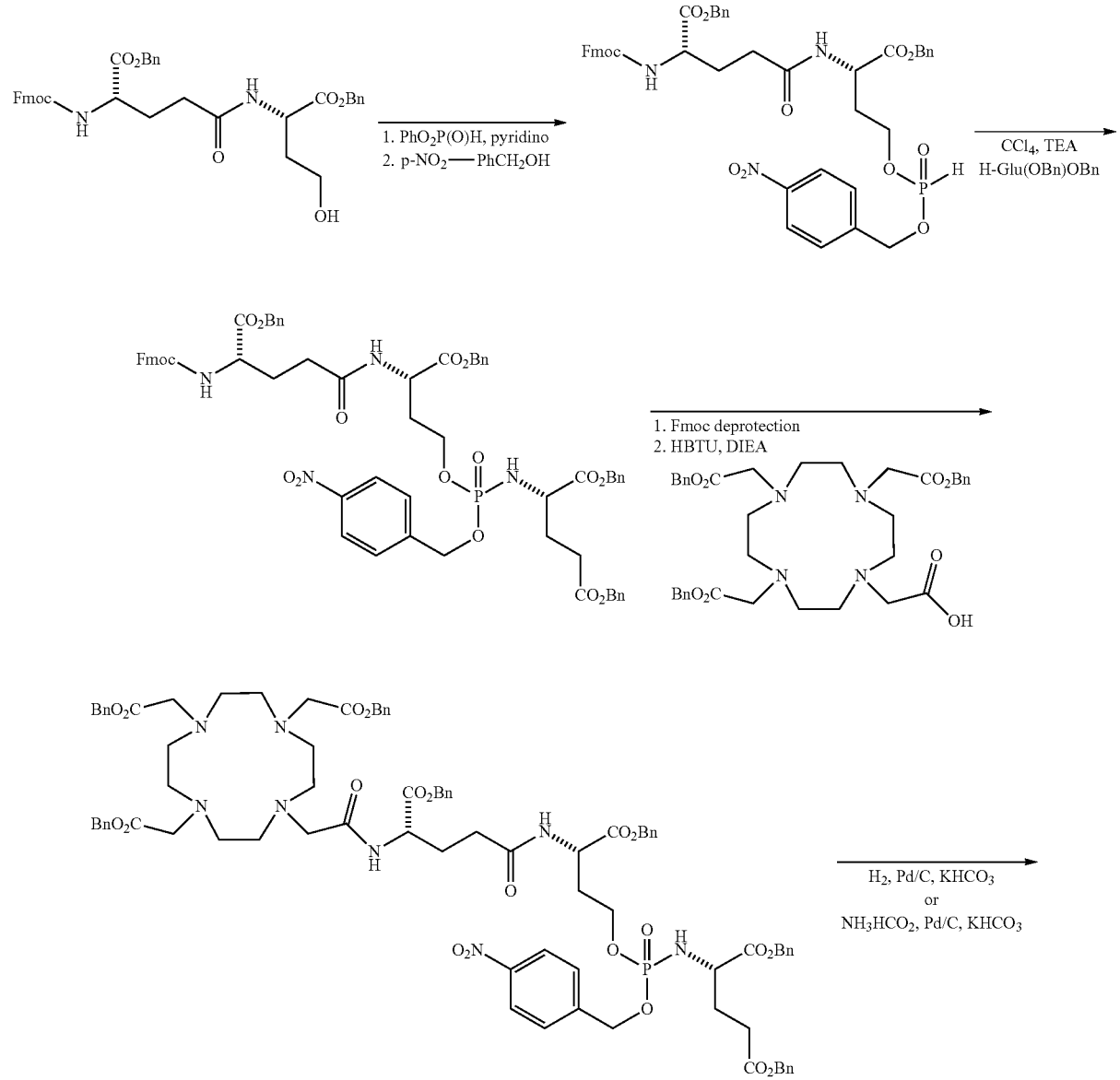

-continued
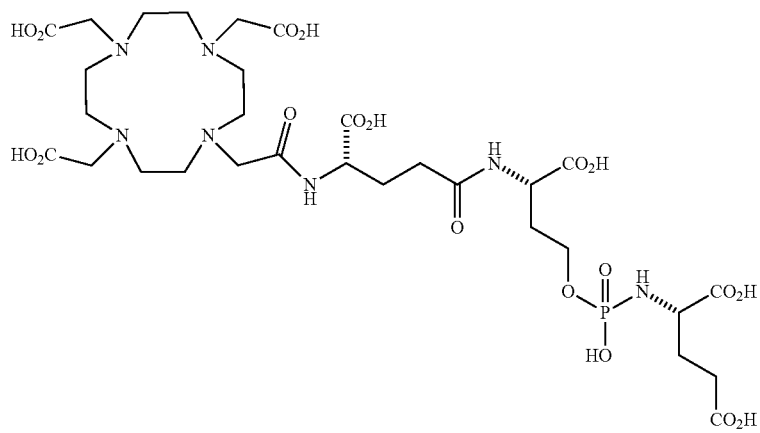
Representative Preparation of Cold Standards
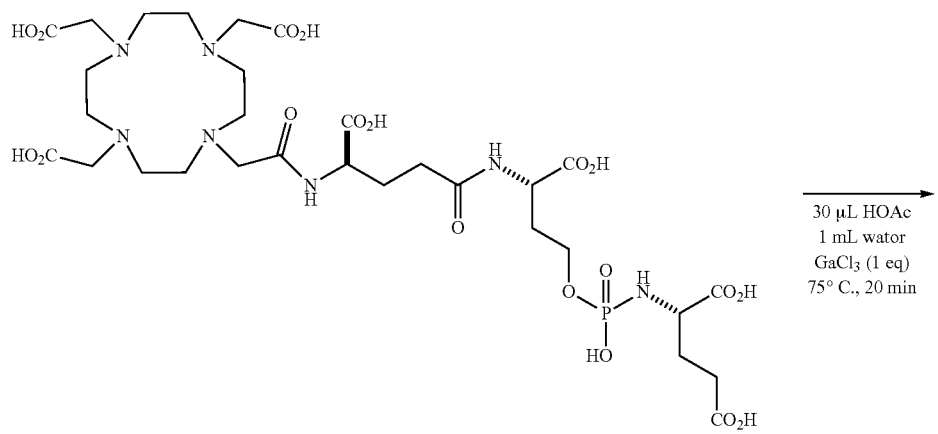
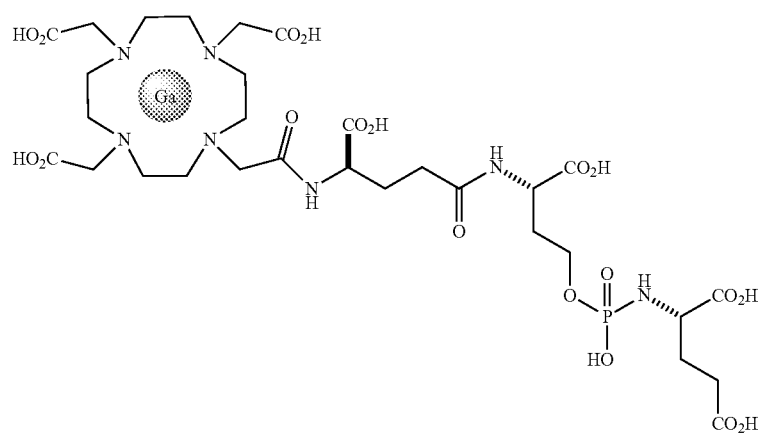

Alternative Representative Preparation of Hot ($^{68}$Ga) Conjugates and Cold ($^{69}$Ga) Standards
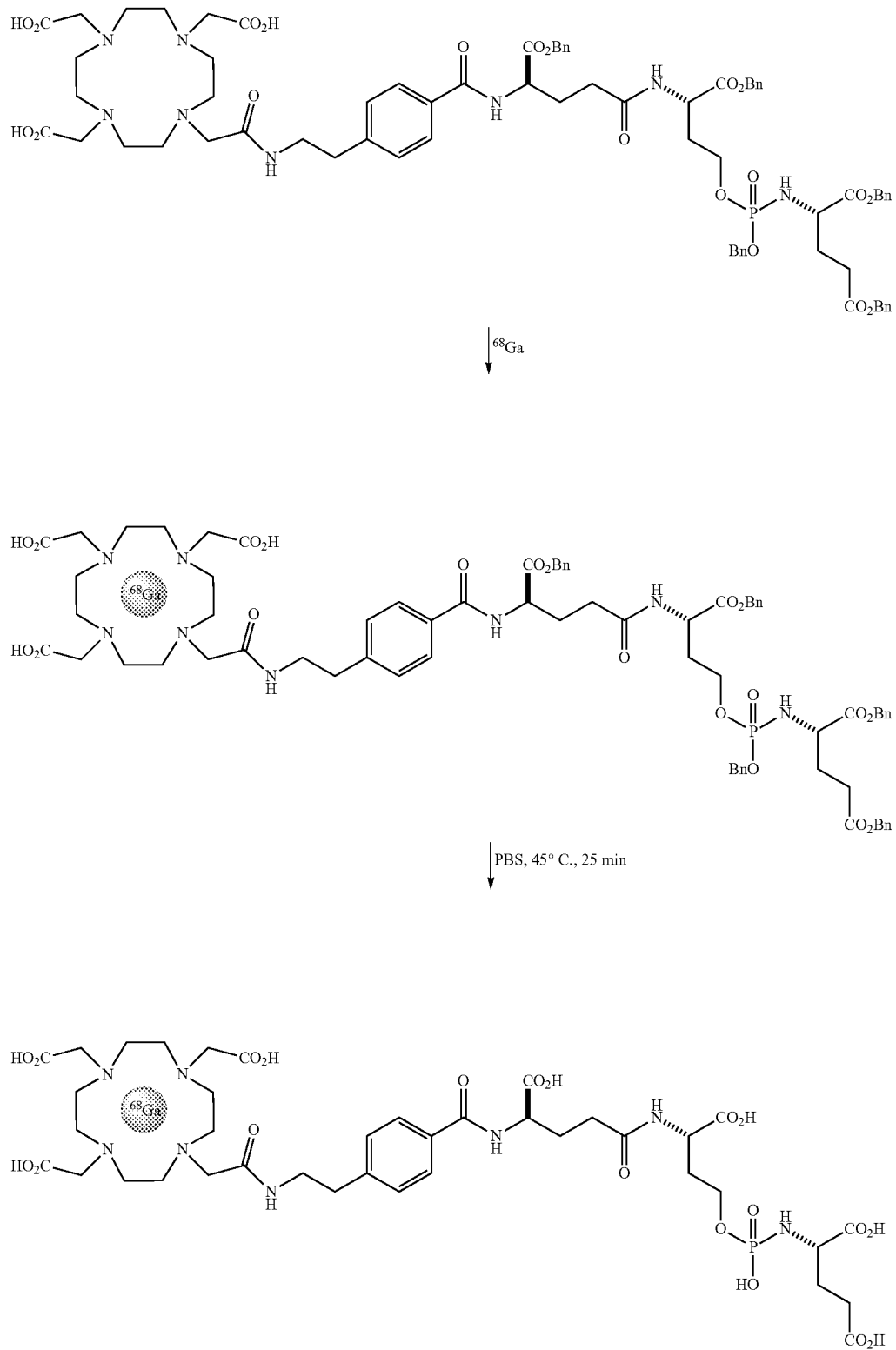

Example 3

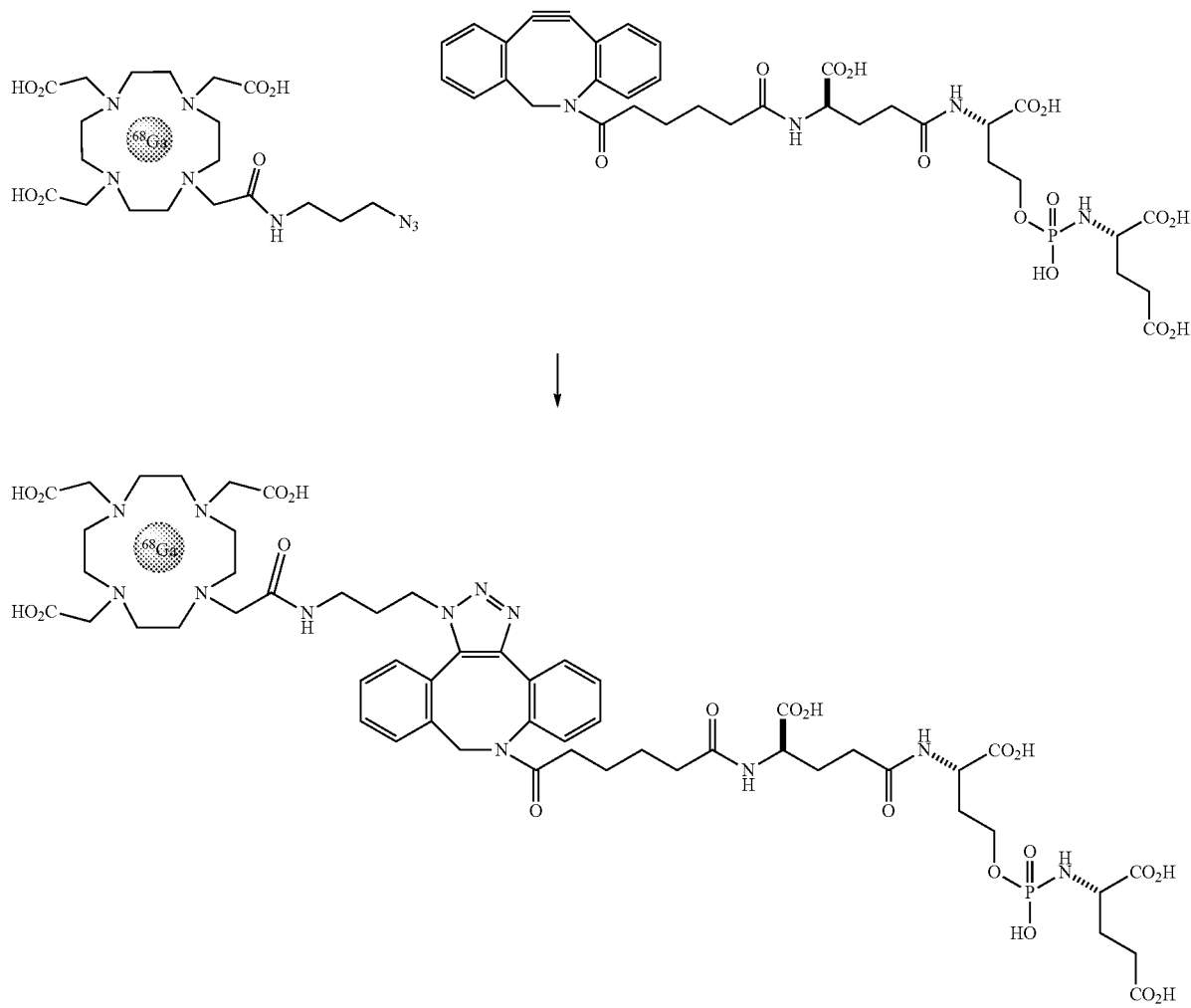

In one example, a Ga-chelating group is attached to a PMSA inhibitor as shown in the preceding scheme. Therein, an azide-terminated chelator (e.g., DOTA modified with 3-azidopropylamine) is reacted under Cu-free conditions familiar in the art with a DBCO-modified PMSA inhibitor to yield a chelator-labeled PSMA inhibitor. The Ga-chelate may be formed either prior to or after the azide coupling step. In another example, the DBCO-modified PMSA inhibitor may comprise a polyethyleneoxide linking group as seen in the following.

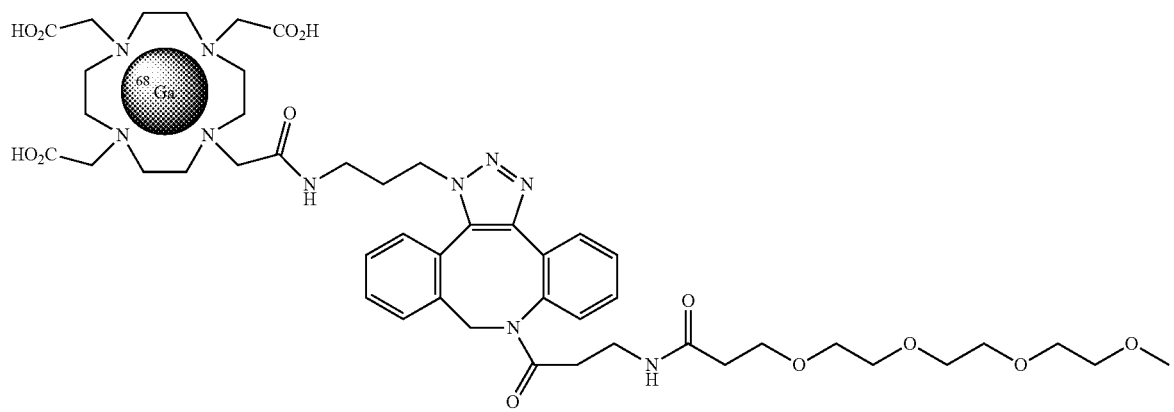

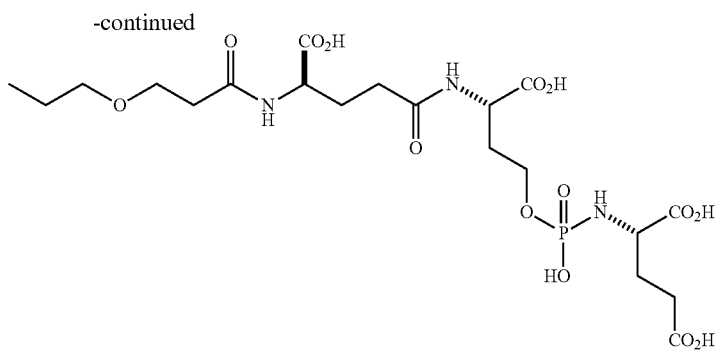

Example 4 Chemical Syntheses

Dibenzylcyclooctyne (DBCO)-PEG$_4$-NHS ester was purchased from Click Chemistry Tools (Scottsdale, Ariz.). All other chemicals and cell-culture reagents were purchased from Fisher Scientific (Sommerville, N.J.) or Sigma-Aldrich (St. Louis, Mo.).

L2-{[2-(4-Amino-4-carboxy-butyrylamino)-2-carboxyethoxy]-hydroxy-phosphorylamino}-pentanedioicacid pentapotassium salt (CTT-54, [7]) and 2-{[2-(4-Amino-4-carboxy-butyrylamino)-2-carboxyethoxy]-hydroxy-phosphoryloxy}-pentanedioic acid pentapotassium salt (CTT-54.2, [8]). Were synthesized as previously reported (see, Nedrow-Byers J R, Jabbes, M., Jewett, C., Ganguly, T., He, H., Liu, T., Benny, P., Bryan, J. N. and Berkman, C. E. A phosphoramidate-based prostate-specific membrane antigen-targeted SPECT agent. The Prostate 2011; and Maung J, Mallari J P, Girtsman T A, Wu L Y, Rowley J A, Santiago N M, Brunelle A N, Berkman C E. Probing for a hydrophobic a binding register in prostate-specific membrane antigen with phenylalkylphosphonamidates. Bioorg Med Chem 2004; 12(18):4969-4979.).

DBCO-PEG4-CTT-54 [5].

Compound 7 (16.7 mg, 0.0264 mmol) was dissolved in 0.60 ml of 100 mM K$_2$CO$_3$ buffer. DBCO-PEG$_4$-NHS (20 mg, 0.041 mmol) dissolved in 0.50 ml of DMSO was added to 7 and stirred 3 h. The percent yield was 98% as determined by HPLC and the crude material was used without further purification for the subsequent radiolabeling step. MALDI high-resolution mass spectrometry (M+H): calculated 1022.3647, found 1022.4085 for C$_{45}$H$_{58}$N$_5$O$_{20}$P$^+$.

DBCO-PEG4-CTT-54.2 [6].

Compound 8 (31.6 mg, 0.0229 mmol) was dissolved in 0.60 ml of 100 mM K$_2$CO$_3$ buffer. DBCO-PEG$_4$-NHS (25 mg, 0.036 mmol) dissolved in 0.40 ml of DMSO was added to 8 and stirred 3 h. The percent yield was 90% as determined by HPLC and the crude material used without further purification for the subsequent radiolabeling step. MALDI high-resolution mass spectrometry (M−H+2Na): calculated 1067.3121, found 1067.4208 for C$_{45}$H$_{58}$N$_4$Na$_2$O$_{21}$P$^+$.

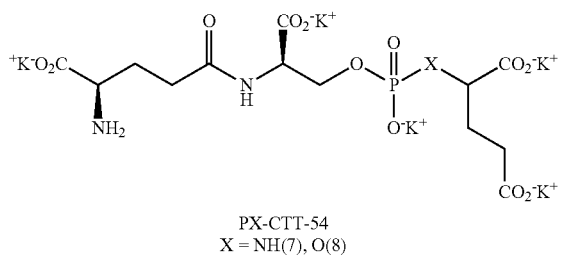

PX-CTT-54
X = NH(7), O(8)

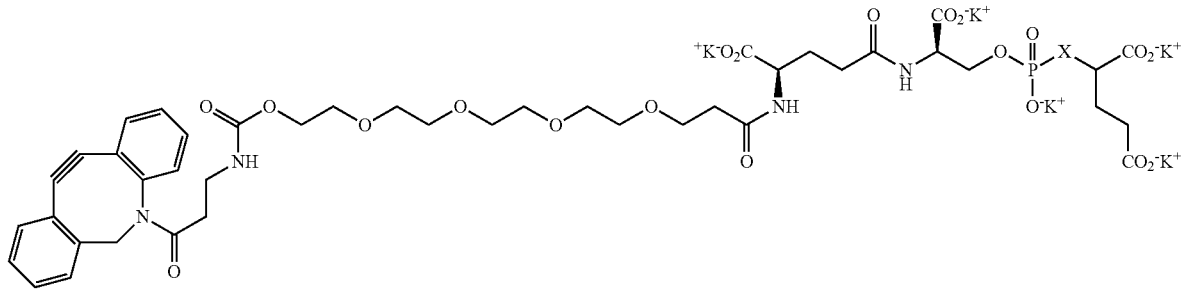

DBCO-PEG4-PX-CTT-54
X = NH(5), O(6)

Example 5 Solid Phase Chemical Syntheses

Fmoc-Homoserine-OH (1 eq.) and DIEA (Di-isopropylethylamine) (2 e.q) in DMF (N,N-dimethylformamide) were mixed with 2-chlorotrityl chloride resin and incubated overnight. The solution was drained and the resin washed with DMF, followed by incubation with a solvent mixture of Methanol/DIEA/dichloromethane for 20 min.

The resin was then sequentially assembled with the desired sequence as depicted in scheme 1 (resin 2) by using the standard solid phase peptide synthetic approach. Below is the list for the reagents.
  (i) 20% piperidine in DMF, 10 min
  (ii) Fmoc-Glu-OBzl (2 eq), HBTU (2 eq), DIEA (4 eq), 4h
  (iii) Repeat step (i)
  (iv) Fmoc-4-(aminoethyl)benzoic acid (2 eq), HBTU (2 eq), DIEA (4 eq), 4h
  (v) Repeat step (i)
  (vi) DOTA tribenzyl ester (1.2 eq), HBTU (2 eq), DIEA (4 eq), 4 h The resin was drained again, washed with DMF and dichloromethane and dried in vacuo for 2 hours. The resin was then swollen in dry dichloromethane for 20 min. and mixed with diphenyl phosphite (2 eq) in pyridine and incubated for 12 hours. This was followed by an overnight incubation with benzyl alcohol (2 eq) in pyridine/dichloromethane to obtain resin 3, followed by the addition of H-Glu(OBzl)-OBzl.pTsOH (2 eq), DIEA (4 eq) and a mixture of $CCl_4$/dichloromethane (1/1) and incubated an additional 12h (resin 4). After thorough washing and drying in vacuo for 2 hours, a cleavage mixture of acetic acid/dichloromethane (2:1) was added to dry resin and incubated for 1 hour. The solution was collected by filtration and the resin was washed with dichloromethane. The filtrates were combined and concentrated. The residue was treated with cold ether to furnish the crude product. The crude product was purified by column chromatography. The correct fraction was concentrated and reduced by hydrogenation in the presence of 10% Pd/C and $H_2$ in THF/water/$NaHCO_3$ (8 eq.) for 18 hours. The catalyst was filtered off and washed with water (5 mL). The filtrates were combined, concentrated to dryness, washed with acetonitrile, ethyl acetate and ether each for three times, dried in vacuo.

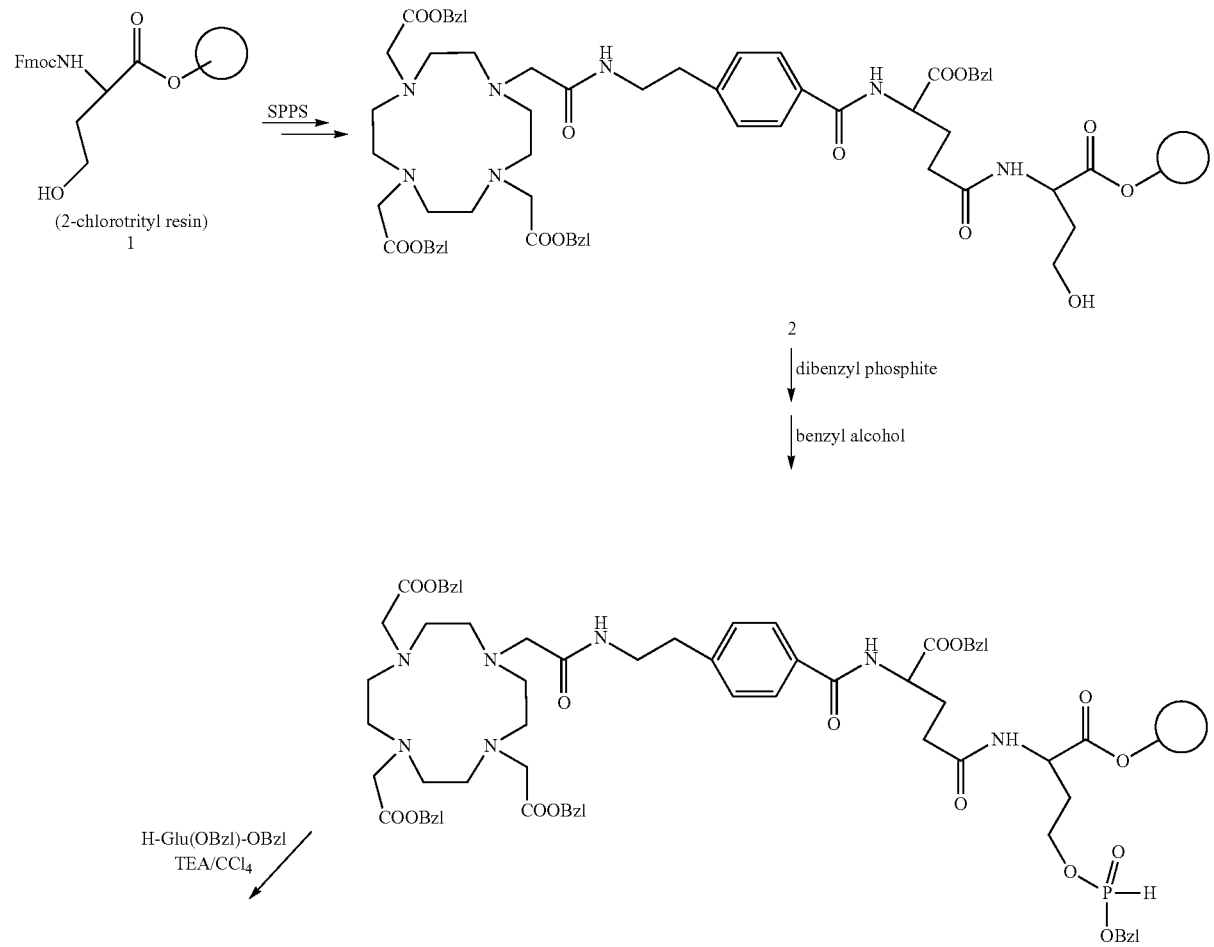

Scheme 1. Solid phase synthesis of CTT1156

-continued
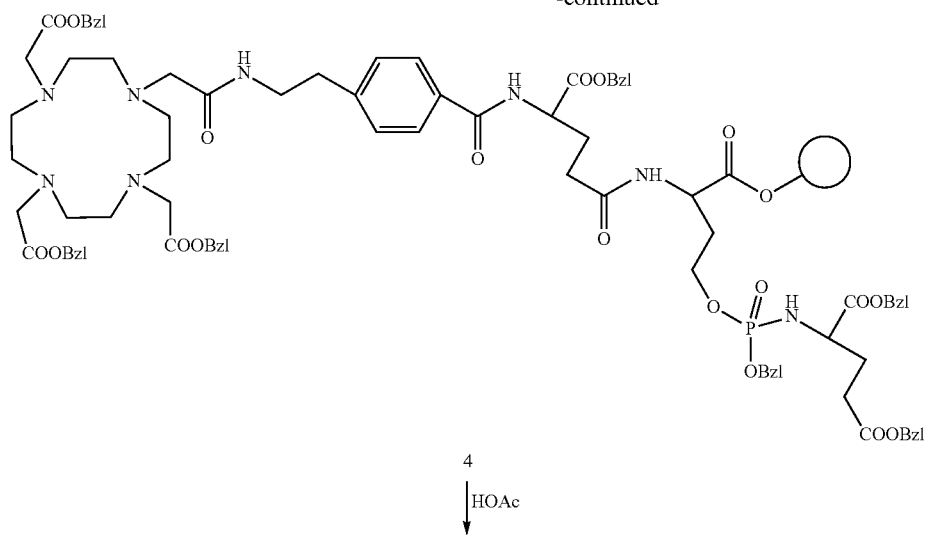
4 ↓ HOAc
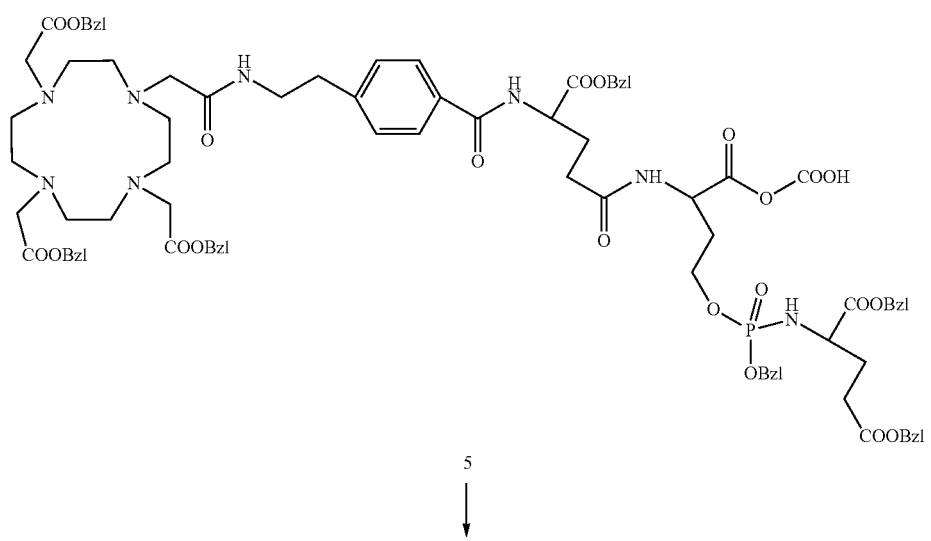
5 ↓
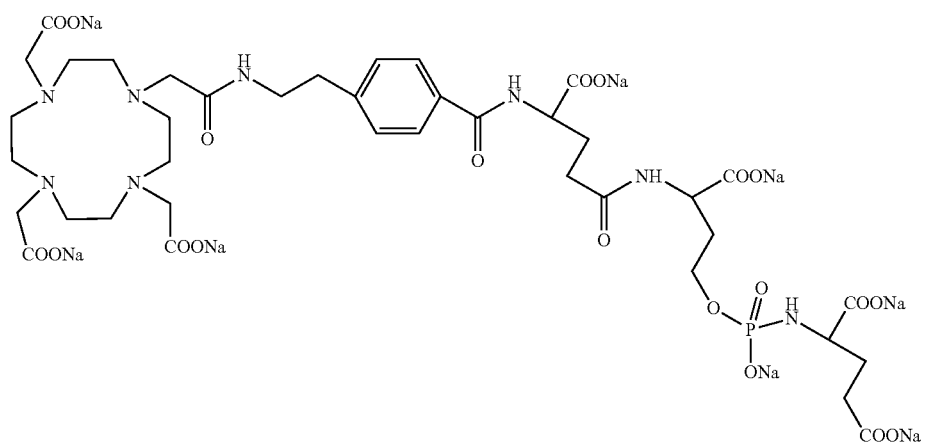
6

Example 6 Stability Studies

Based on preliminary labeling and deprotection studies with the serine-based scaffold of CTT54, acid and base stability issues were noted. The instability of CTT54 and its protected precursors under basic conditions is due to beta-elimination on serine to yield a dehydroalanine derivative. The acid instability was centered on the P—N bond of CTT54, which precluded the use of acid modifiers in HPLC mobile phases. It was found that the substitution of serine in the CTT54 scaffold with homoserine or 2(3-hydroxypropyl)glycine solved both the acid and basic stability issues. The homoserine analog was known initially as hCTT54 and later, more formally, as CTT1000. The 2(3-hydroxypropyl)glycine is known as TG97 and CTT2000. The base stability was expected as the beta-elimination problem associated with phosphorylated serine residue would be blocked. However, the acid stability was unexpected. In addition to the improved stability, these compounds retain their binding to PSMA: CTT1000 $IC_{50}$=15 nM, irreversible; CTT2000 $IC_{50}$=27 nM, irreversible.

and 5.5; 1 M Tris-maleate for pH 6.5 & 7; 1 M Tris-HCl for pH of 7.5 & 8. The procedures for determining pH stability by $^{31}P$ NMR are detailed as follows. The sample (~4 mg) was dissolved buffer (~1 mL of a 1 M solution) resulting in a approximately a 5 mM solution of the analyte (CTT1000 or CTT2000). The pH was adjusted as necessary (usually with HCl); actual pH noted on spectra and the time was defined as t=0. An initial $^{31}P$ NMR spectra was obtained (t~0.5 h) and acquired each hour (1-8 h) The external reference for $^{31}P$ NMR was triphenylphosphine oxide (27 ppm).

The unconjugated core of hCTT54/CTT1000 was stable for 8 hours with no detectable hydrolysis down to pH 4.5; possible hydrolysis products in the NMR samples were not observed by mass spectrometry. This acid stability enables the use of acid modifiers in HPLC mobile phases and acid labile protecting groups such as tBu. The inhibitor core TG97/CTT2000 was stable for 8 hours with no detectable hydrolysis down to pH 3.

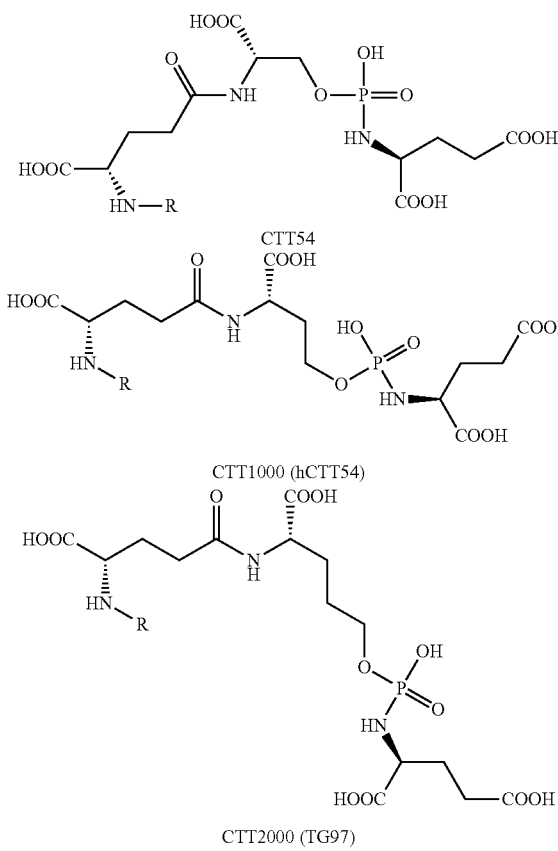

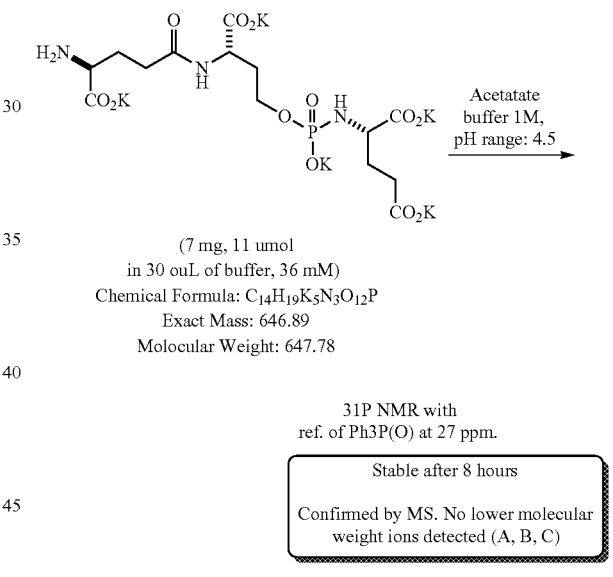

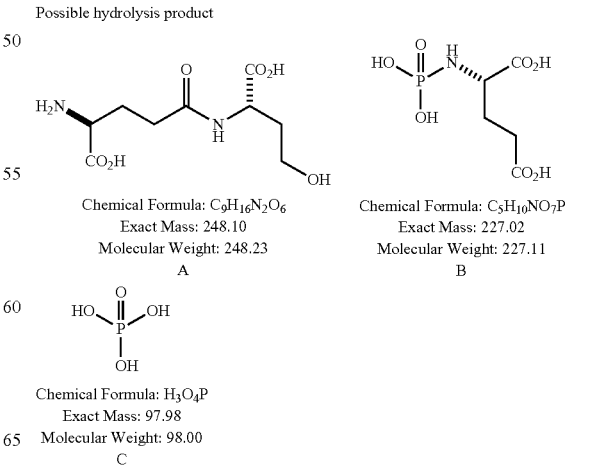

pH Stability Studies

The room temperature stability of hCTT54 was monitored by $^{31}P$ NMR at various pH values using 1 M buffers: 8, 7.5, 7, 6.5, 5.5, 4.5, 4, 3, 2. The following 1M buffers were used: HCl—KCl for pH 2, Citrate for pH 3 & 4, Acetate for pH 4.5

Example 7 Radioimaging Studies

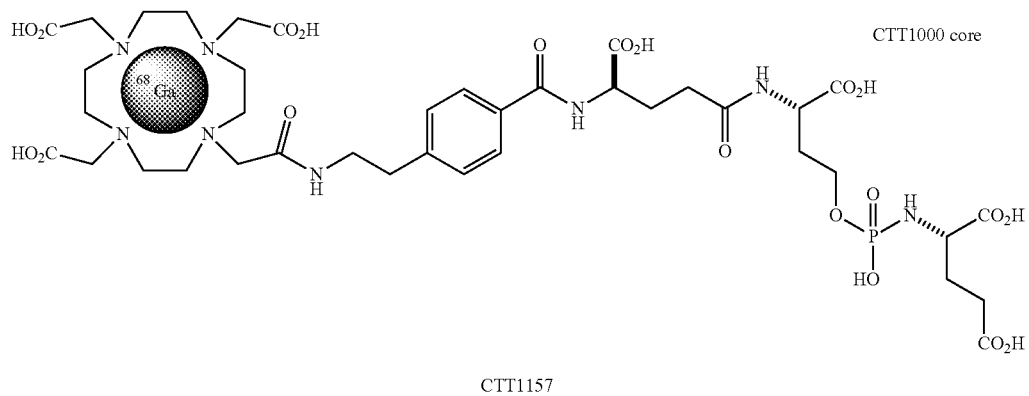

CTT1157

0.68 mci of Ga-68 (0.26 mL) in 0.1M of HCl was mixed with 75 µl of Sodium acetate buffer (pH 6.5) to adjust pH to 4.5-5.0. 30 µg of CTT1156 (10 mg/mL) was added to the mixture and incubate at 90° C. for 10 min. The labeling was analyzed by HPLC (Luna 5µ HILIC 200 A 250×4.6 mm column), Ga-68 labeled CTT1156 was eluted from solvent gradient. Solvent A 10 mM ammonium acetate, solvent B AcCN, initiate from 25% of A and 75% of B, 0-15 min Solvent A 25%-50%, 15-18 min 1:1 solvent A and B, and 18-20 min, solvent A is from 50% to 25%.

After incubation, mixture was cooled down to room temperature. Labeling yield was analyzed by HPLC (0.1 mci of mixture injection (50 µl) into HILIC column). The Ga-68 labeled CTT1156 was eluted out at 10 min and purified by HILIC column. Organic solvent was removed under vacuum with nitrogen flow.

0.080 mci of Ga-68 labeled CTT1156 (0.25 ml) was injected into mice which bear Ln-cap tumor on both side of upper flank.

PET/CT dynamic scan from 0-1 hour.

Figure 6:
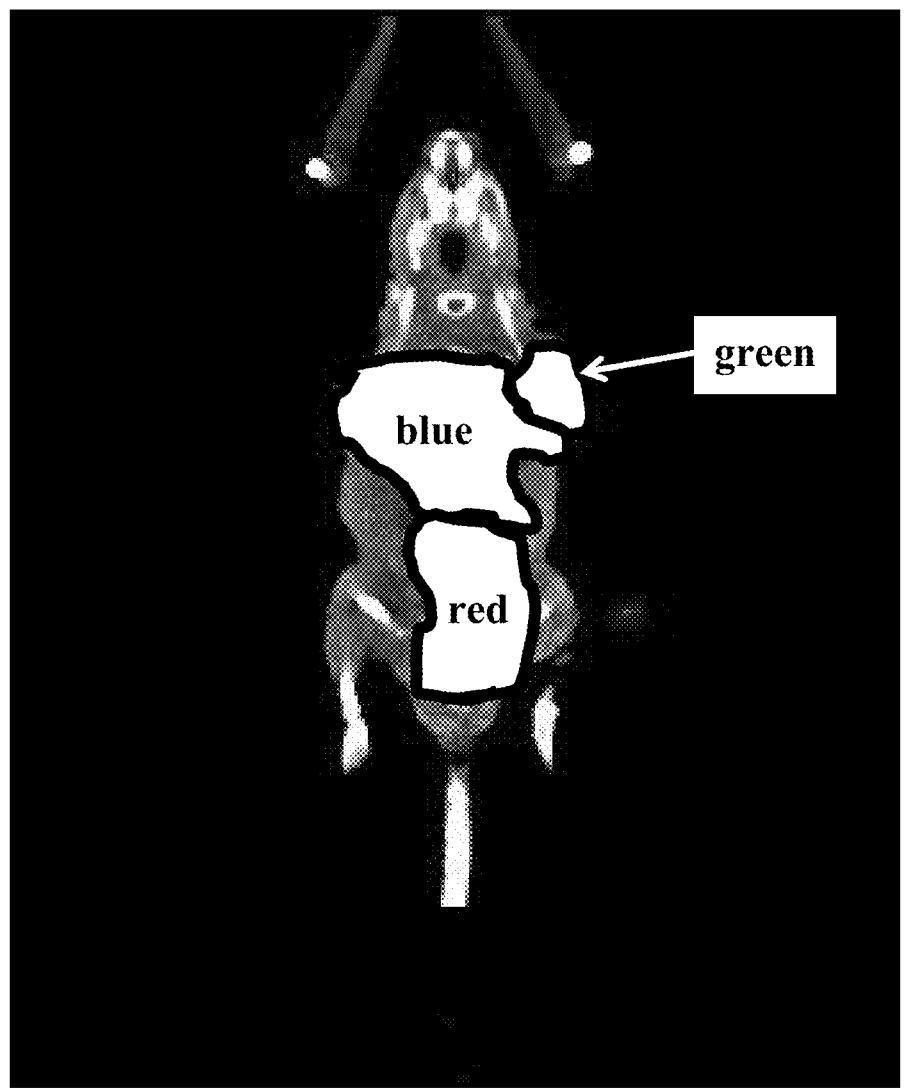
FIG. 6 shows biodistribution of Ga-68 labeled CTT1156 at 1 hour post injection into mice bearing Ln-cap tumor.

16 µci of Ga-68 labeled CTT1156 was injected to mice bearing Ln-cap tumor, and biodistribution performed at 1 hour post injection, as shown in FIG. 6.

Example 8 Synthesis of 4-nitro-benzyl tetraisopropylphosphorodiamidite, [(iPr$_2$N)$_2$P(OpNb)]

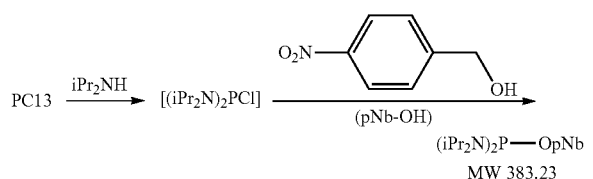

To a solution of diisopropylamine (DIPA, 50.0 g, 544 mmol) in anhydrous hexane (230 mL) was added dropwise a solution of trichlorophosphine (18.7 g, 136 mmol) in anhydrous hexane (30 mL) over 40 min with stirring at 0° C. in an atmosphere of N$_2$. The mixture was stirred for 3h at room temperature, and then heated under reflux for 4 days. To the reaction mixture neutralized with TEA was added a solution of 4-nitrobenzyl alcohol (pNb-OH, 21 g, MW153.14, 136 mmol) and TEA (13.8 g, 136 mmol) in anhydrous EtOAc (100 mL) over 1 h with stirring at 0° C. in an atmosphere of N$_2$. After stirring for 30 min at room temperature, the precipitated salt was filtered off and washed with hexane (50 mL) once. The filtrates were combined and concentrated under reduced pressure. The residue was dissolved in hexane (350 mL), and the solution was washed with acetonitrile (30 mL×3), followed by evaporation under reduced pressure. An oily residue was purified by column chromatography on silica gel (silica gel was sufficiently pre-washed with hexane: TEA 10:1) and pure (iPr$_2$N)$_2$P (OpNb) was obtained by elution with hexane: TEA (100:1) as solid powder. MS: Calc. 383.23, found 384.26. Weight: 24 g, Yield: 46%.

Example 9 Synthesis of N-Fmoc-L-homoserine

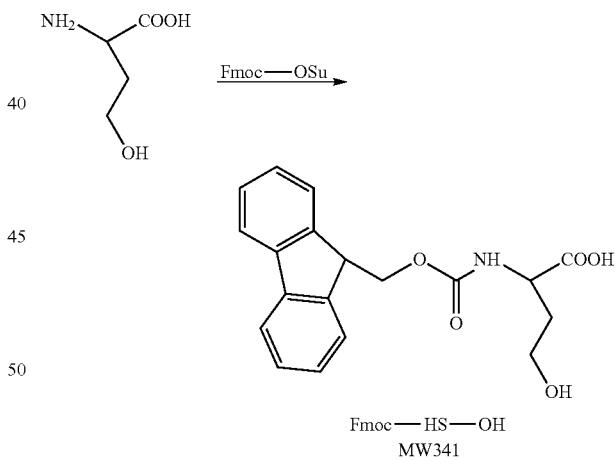

L-homoserine (15 g, MW119.12, 0.126 mol) and NaHCO$_3$ (22 g, MW84, 0.26 mol) were dissolved in water (600 mL). The solution was chilled in an ice bath, followed by addition of Fmoc-OSu (42.5 g, MW337.3, 0.126 mol) in acetone (400 mL). The mixture was stirred overnight. A mixture of ether/water (200 mL/200 mL) was added, and the solid was filtered off. The filtrate was separated and the aqueous phase was washed with ethyl twice (100 mL×2), followed by acidifying with 3N HCl$_{aq}$ (about 100 mL) to pH3-4. The suspension was extracted with ether (200 mL×2). The combined organic phases were washed with brine once (100 mL) and dried over Na$_2$SO$_4$. After evaporation, white solid was obtained (weight: 38 g, yield: 88%).

Example 10 Synthesis of N-Fmoc-L-Homoserine Benzyl Ester

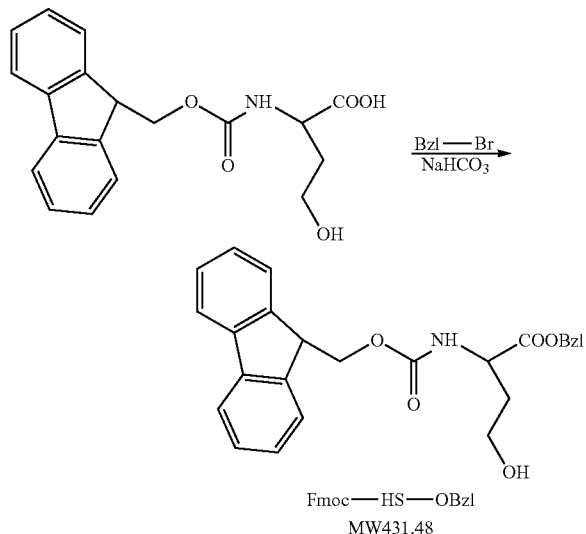

Fmoc-HS-OH (10 g, MW341, 29.3 mmol) was dissolved in dioxane (75 mL). While stirring, aqueous NaHCO₃ (2.7 g, MW84, 32 mmol) solution (40 mL) was dropwise added into the solution, followed by stirring for 30 min. After evaporation under reduced pressure, the residue was dissolved in DMF (100 mL). The solution was chilled in an ice bath, followed by addition of benzyl bromide (5.0 g, MW171, 29.2 mmol). The mixture was allowed to stir for 5h. The solvent was evaporated under reduced pressure and the residue was partitioned with EtOAc/5% aqueous NaHCO₃ (100 mL/100 mL). The organic phase was separated and the aqueous phase was extracted EtOAc twice (50 mL×2). The organic phases were combined and washed with 5% aqueous NaHCO₃ (50 mL), dried over Na₂SO₄. The solvent was evaporated to obtain white power (weight: 7.5 g, yield: 60%).

Example 11 Synthesis of Compound 1

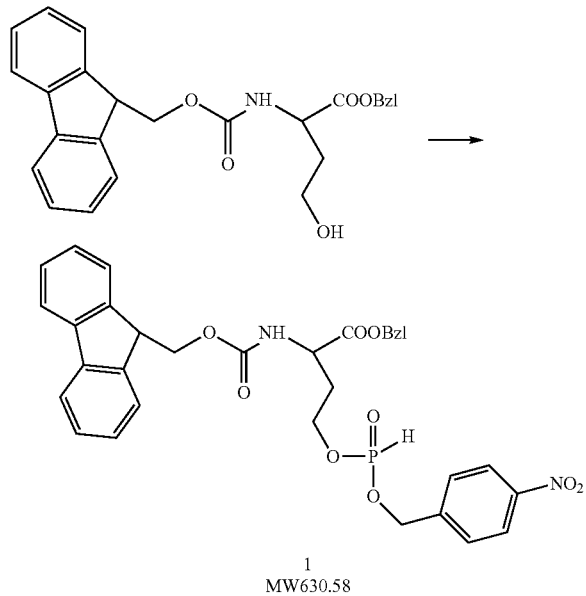

Fmoc-HS-OBzl (5 g, MW431.5, 11.6 mmol) and (iPr₂zN)₂P(OpNB) (5.5 g, MW383, 14.4 mmol) were dissolved in DCM (100 mL). The solution was chilled in an ice bath, followed by addition of diisopropylammonium tetrazolide (DIHT, 2.4 g, MW170.26, 14.1 mmol). The solution was allowed to stir overnight at room temperature. The solvent was evaporated and the residue was dissolved in acetonitrile. The insoluble solid was filtered off and washed with acetonitrile once (10 mL). The filtrates were combined and incubated with 5-SET (4.5 g, MW130.13, 34.6 mmol) in acetonitrile/water (25 mL/15 mL) at 40° C. for 1 h. After evaporation, the residue was partitioned in EtOAc/water (100 mL/50 mL), and washed with 1N HCl (3×30 mL), 10% NaHCO₃ (3×30 mL) and brine (30 mL) once, dried over Na₂SO₄. The residue was purified by column chromatography (Elute: hexane/EtOAc, 1/1). Weight: 4.3 g, yield: 60%.

Example 12 Synthesis of Compound 2

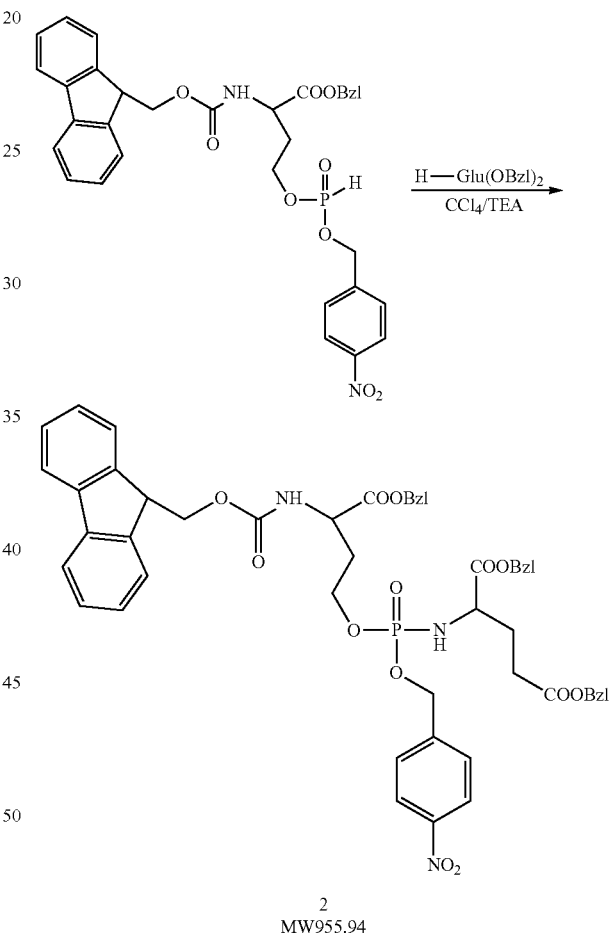

Compound 1 (3 g, MW630.58, 4.75 mmol), H-Glu(OBzl)₂.TsOH (2.4 g, MW499.5, 4.8 mmol) and triethylamine (TEA, 2 mL, MW101, d0.72, 14.4 mmol) were mixed in DCM (50 mL). The clear solution was chilled in an ice bath and CCl₄ (1.4 mL, MW153.82, d1.59, 14.5 mmol) was added, followed by stirring for 1 h at room temperature. The solvent was evaporated and the residue was dissolved in EtOAc (50 mL), washed with 1N HCl (30 mL×2), 5% NaHCO₃ (30 mL×2) and brine (30 mL), dried over Na₂SO₄. After evaporation, the residue was purified by flash chromatography on silica gel (Elute: Hexane/EtOAc, 1/1). Weight: 3 g, Yield: 70%.

Example 13 Synthesis of Compound 3

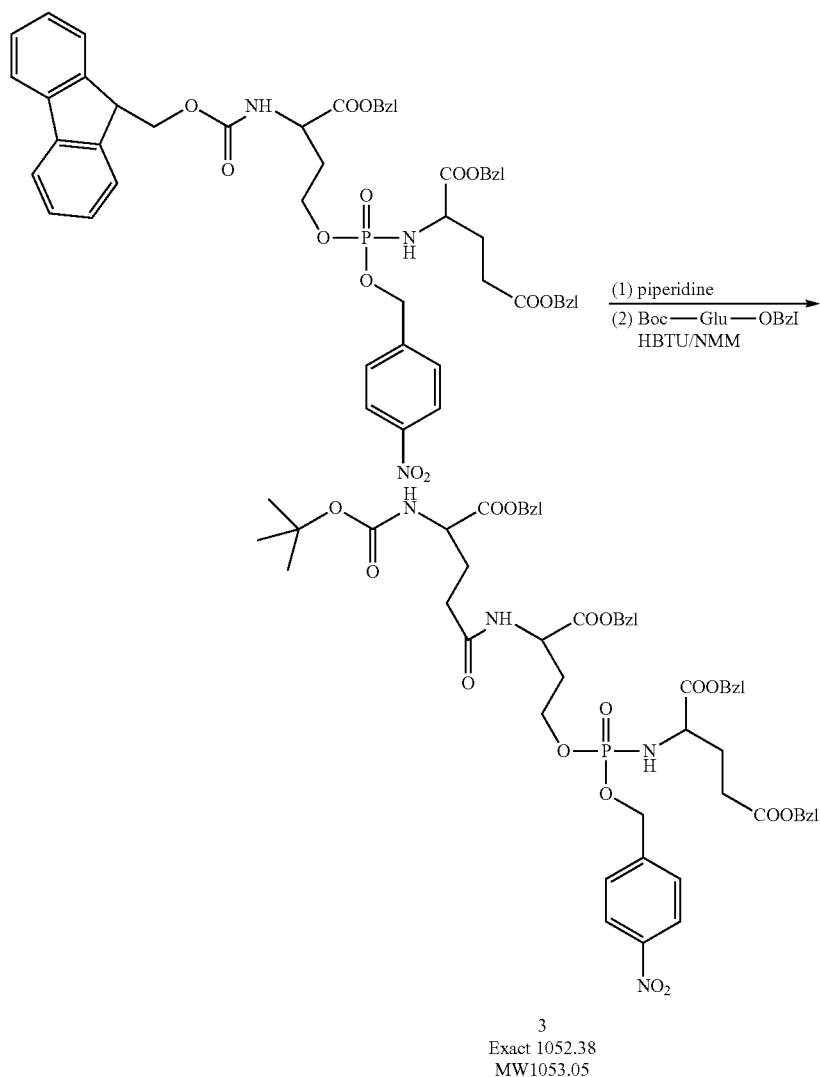

Compound 2 (3 g, MW955.94, 3.1 mmol) was incubated with 20% 4-methylpiperidine in DCM (20 mL) for 10 min. Solvents were evaporated under reduced pressure, and the residue was diluted with hexane, and evaporated. The residue was purified by column chromatography on silica gel (Elute: DCM/MeOH, 5/1) to yield an oil (Weight: 1.5 g). The oil was mixed with Boc-Glu-OBzl (0.7 g, MW337.4, 2 mmol)/HBTU (0.84 g, MW379, 2.2 mmol)/NMM (0.7 mL, MWIOI, d0.92, 6 mmol) in DCM (75 mL) for 3h. After evaporation of the solvent, the residue was dissolved in EtOAc (50 mL) and the solution was washed with 1N HCl three times (30 mL×2), 5% NaHCO₃ three times (30 mL×2) and brine once (30 mL), dried over Na₂SO₄, then purified by flash chromatography on silica gel (Elute: Hexane/EtOAc, 1/1). Weight: 1.7 g. Total yield: 52%.

Example 14 Synthesis of CTT1000 Hydrochloride

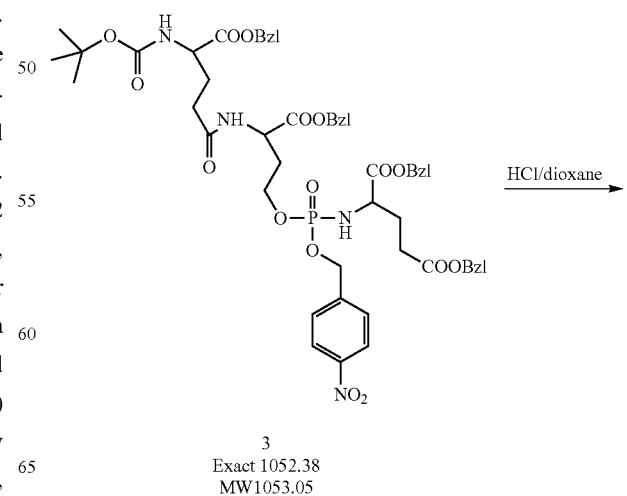

65

-continued

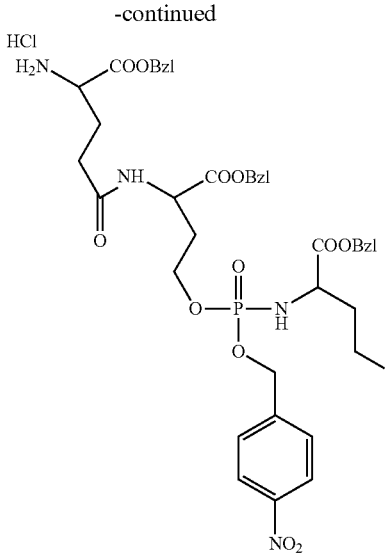

CTT1000
MW989.40

Compound 3 (1.5 g, MW1053, 1.4 mmol) was incubated with 4M HCl solution in dioxane (15 mL) for 1 h. The solvent was evaporated and the residue was diluted with hexane and evaporated to dryness. The residue was dried in vacuo overnight to yield light yellowish solid. Weight: 1.4 g. Yield: 100%.

Synthetic Route to Tribenzyl DOTA Ester
(Bzl₃-DOTA-OH.TFA)

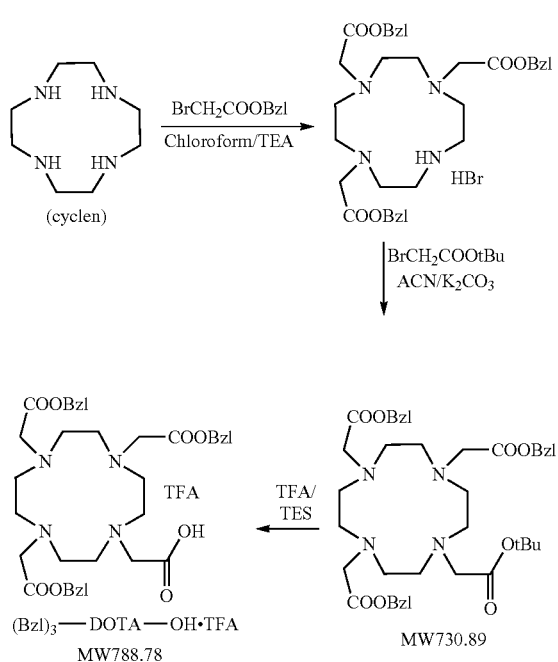

66

Example 15 Synthesis of 1,4,7-tris(benzoxycarbonyl-methyl)-1,4,7,10-tetraazacyclododecane hydrobromide

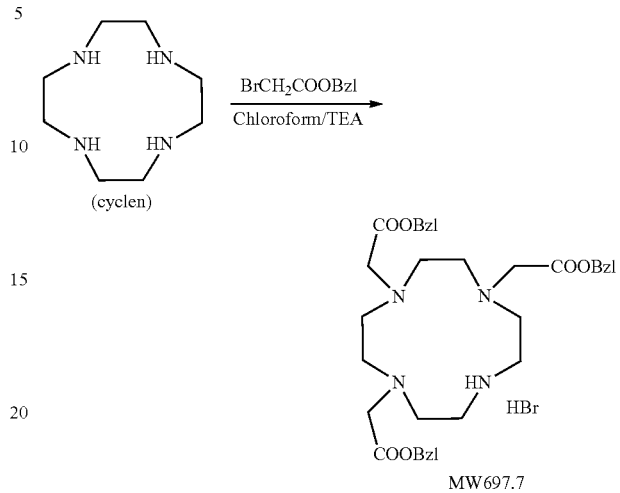

Benzyl bromoacetate (15.2 mL, MW229, d1.446, 96 mmol) dissolved in 25 mL of anhydrous chloroform was added dropwise to a mixture of 1,4,7,10-tetraazacyclododecane (cyclen) (5 g, MW172.28, 29 mmol) and triethylamine (41 mL, MW101, 290 mmol) in 250 mL of anhydrous chloroform under argon atmosphere. The reaction mixture was stirred for 20 h. The resulting solution was washed with water (3×40 mL), and the organic phase was dried by Na₂SO₄. The solvent was removed, and the crude product was purified by flash chromatography on silica gel (Elute: DCM/MeOH, 5/1) to afford the light yellowish oil (Weight: 14 g, yield: 70%).

Example 16 Synthesis of Tert-Butyl Tribenzyl DOTA Ester

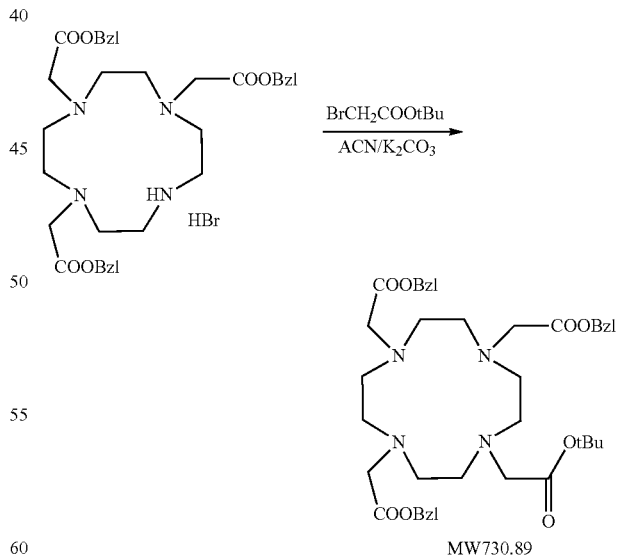

1,4,7-tris(benzoxycarbonyl-methyl)-1,4,7,10-tetraazacyclododecane hydrobromide (13 g, MW697.7, 18.6 mmol) was dissolved in a mixture of 50 mL anhydrous acetonitrile and K₂CO₃ (5.1 g, MW138, 37 mmol). Then tert-butyl bromoacetate (3 mL, MW195, d1.32, 20.3 mmol) in acetonitrile (15 mL) was added. The suspension was allowed to stir for 12 h under N₂ at 70° C. The reaction was monitored by TLC plates. After all the starting material was consumed, the resulting mixture was filtered. The filtrate was concentrated under reduced pressure and the residue was purified by flash chromatography on silica gel (DCM/MeOH, 10/1) to give tert-butyl tribenzyl DOTA ester (12 g, yield: 90%).

Example 17 Synthesis of Tribenzyl DOTA Ester (Bzl₃-DOTA-OH.TFA)

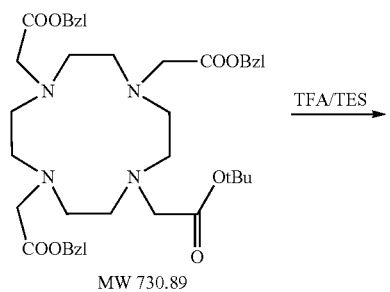

Tert-butyl tribenzyl DOTA ester (12 g, MW730.89, 16.4 mmol) was mixed with 95% TFA/TES (100 mL) in an ice bath. The solution was allowed to incubate overnight at room temperature, followed by evaporation. Hexane (100 mL) was added and the mixture was evaporated to dryness. The residue was triturated with ether twice (50 mL×2) and then purified by flash chromatography on silica gel (DCM/EtOH=5/1) to give the product (Weight: 7 g, yield: 54%).

Synthetic Route to CTT1156 & 1157

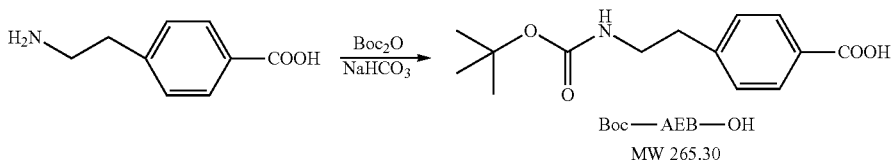

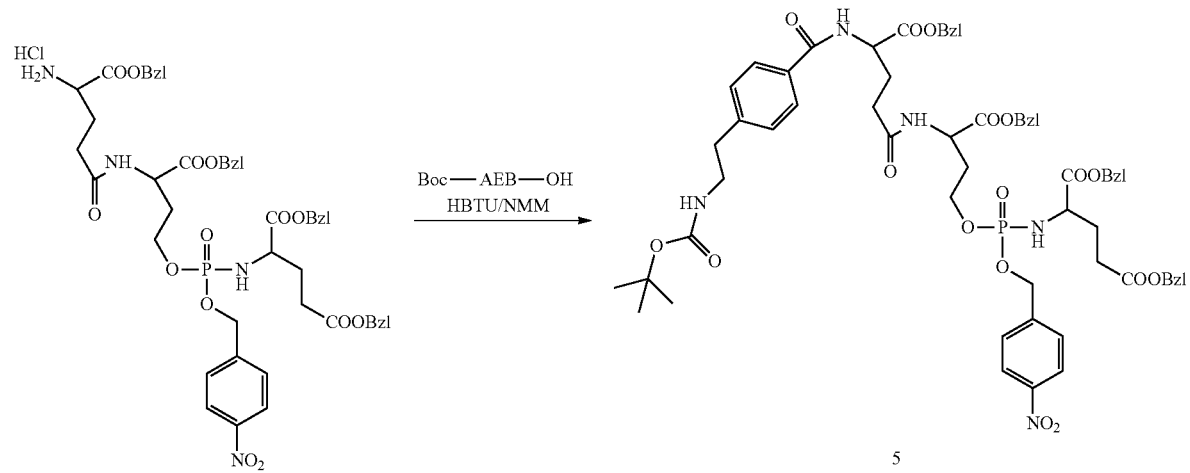

-continued
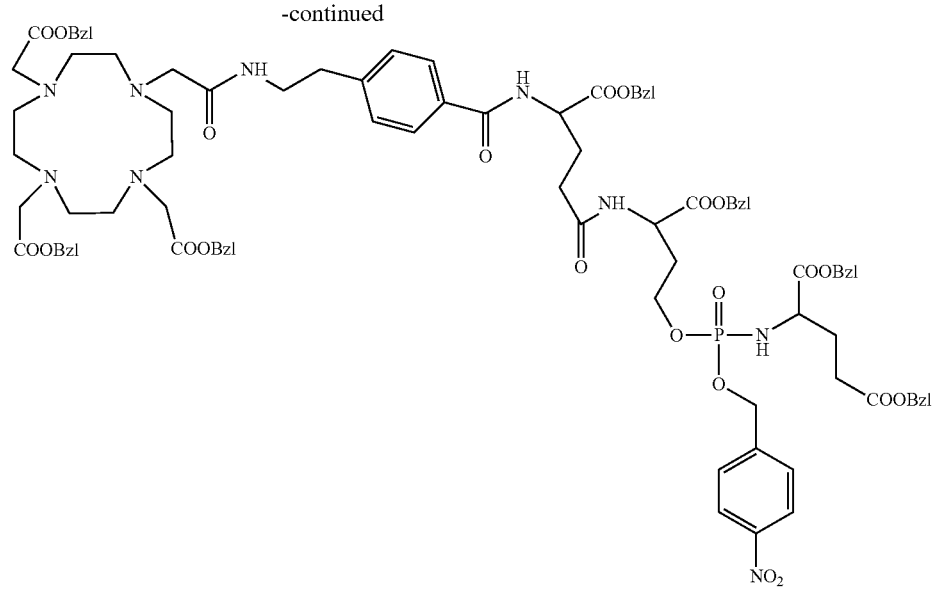
6
MW 1756.88
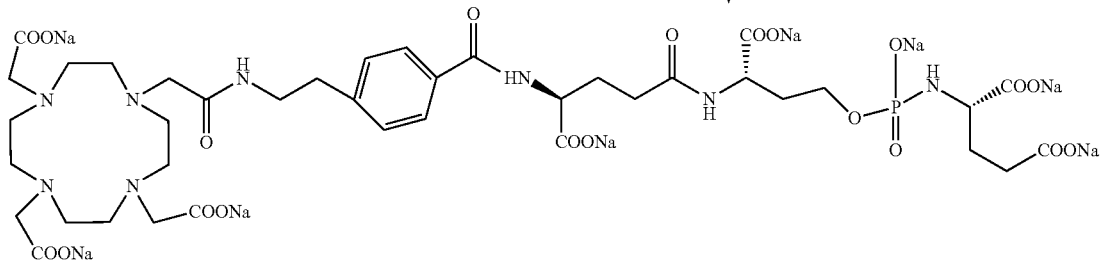
CTT1156
$C_{39}H_{51}N_8Na_8O_{20}P$
MW: 1166.76
GaCl₃/pH 4.9
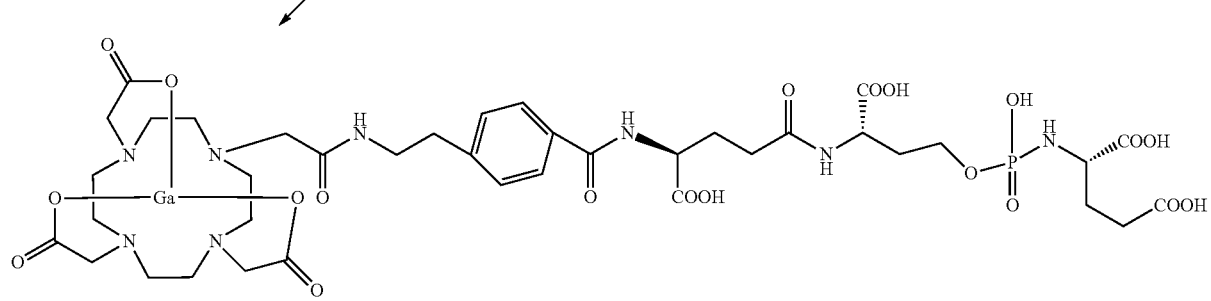
CTT1157
Exact 1056.26
MW: 1057.60
Example 18 Synthesis of N-Boc-4-aminoethylbenzoic acid (Boc-AEB-OH)
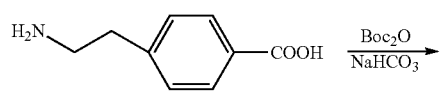
-continued
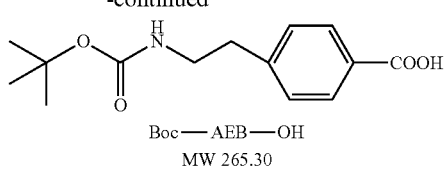
Boc—AEB—OH
MW 265.30 p-aminoethylbenzoic acid hydrochloride (5 g, MW201.5, 24.8 mmol) and NaHCO₃ (5.2 g, MW84, 62 mmol) were dissolved in water (200 mL). The solution was chilled in an ice bath, followed by addition of Boc₂O (5.4 g, MW218, 24.8 mmol) in acetonitrile (50 mL). The mixture was stirred overnight. The resulting solution was concentrated under reduce pressure. The remaining aqueous solution was acidified with 3N HCl$_{aq}$ to pH3.0 and the precipitate was collected by filtration. The filter cake was washed with water once (30 mL) and dried in vacuo to afford white powder (weight: 4.5 g, yield: 59%).

Example 19 Synthesis of Compound 5

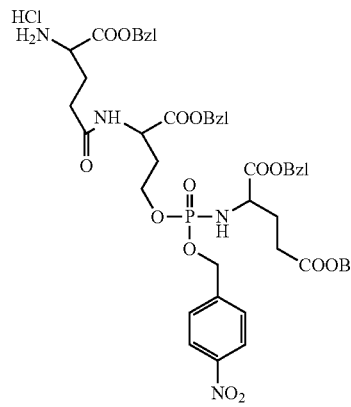

CTT1000-HCl
MW 1053.05

Boc—AEB—OH
HBTU/NMM
→

-continued

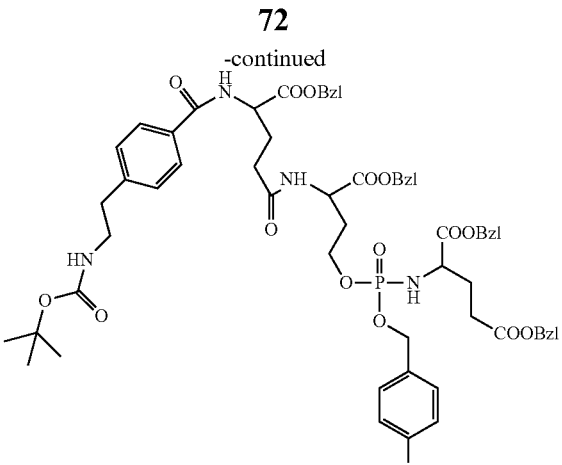

5
MW 1200.23

CTT1000-HCl (0.9 g, MW1053, 0.85 mmol), Boc-AEB-OH (0.23 g, MW265.3, 0.86 mmol), HBTU (0.39 g, MW379, 1.0 mmol) and NMM (0.28 mL, MW101, d0.92, 2.5 mmol) were mixed in DCM (50 mL). The mixture was allowed to stir overnight, followed by concentration. The residue was dissolved in EtOAc (50 mL) and washed with 1M HCl twice (20 mL×2), 5% NaHCO3 twice (20 mL×2), and brine once (20 mL), dried over Na₂SO₄. The residue was directly used without purification after evaporation. Weight: 0.84 g. Yield: 82%.

Example 20 Synthesis of Compound 6 (CTT1156 Precursor)

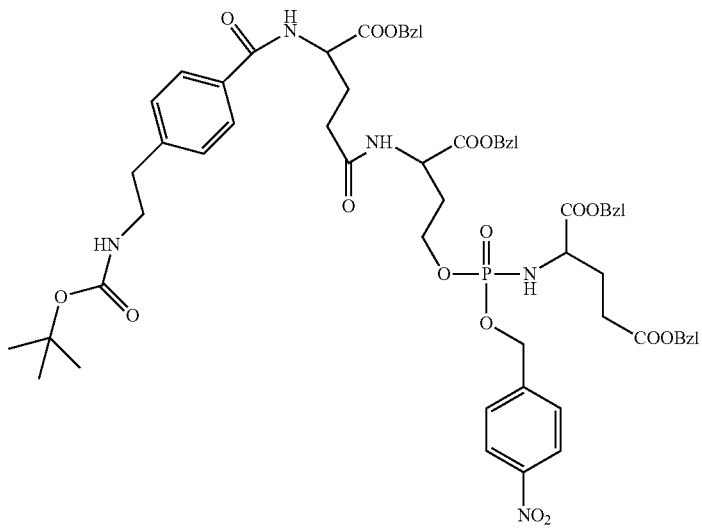

5
MW 1200.23

1) HCl/dioxane
2) Bzl₃—DOTA—OH, HBTU/TEA
↓

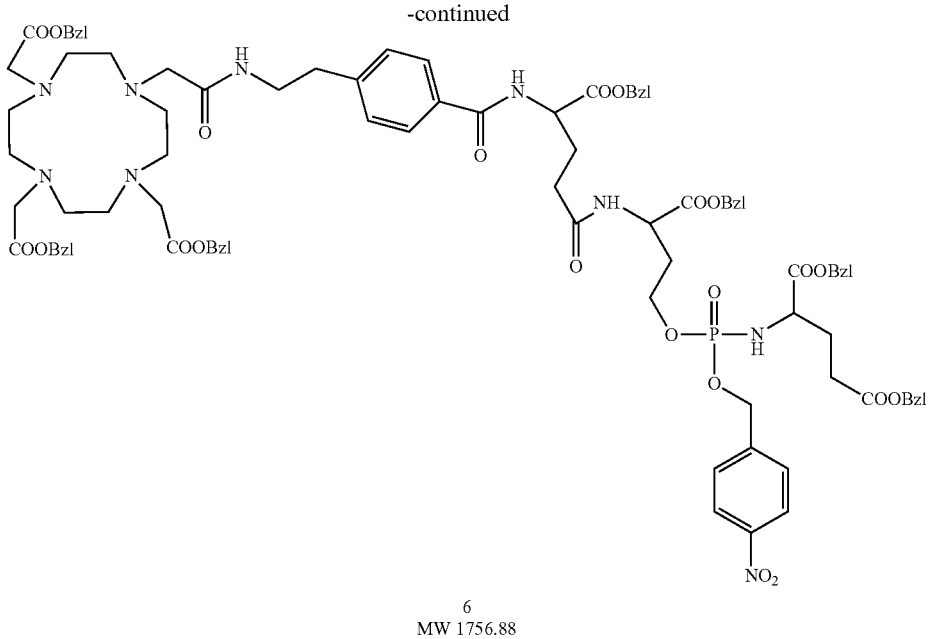

6
MW 1756.88

Compound 5 (0.8 g, MW 1200, 0.67 mmol) and 4M HCl in dioxane (10 mL) were mixed and incubated for 1 h. The solvent was evaporated and the residue was co-evaporated with hexane (50 mL) once. The residue was incubated with Bzl$_3$-DOTA-OH.TFA (0.5 g, MW789, 0.6 mmol), HBTU (0.26 g, MW 379, 0.69 mmol) and NMM (0.33 mL, MW 101, d 0.92, 3 mmol) in DCM (50 mL) overnight. After evaporation, the residue was dissolved in EtOAc (50 mL) and washed with 1M HCl once (20 mL), brine once (20 mL), 5% NaHCO$_3$ once (20 mL), dried over Na$_2$SO$_4$. After evaporation, the residue was purified by flash chromatography on silica gel (Elute: DCM/MeOH, 100/1 to 100/5). Weight: 220 mg, total yield: 21%.

Example 21 Synthesis of CTT1156 Octasodium Salt

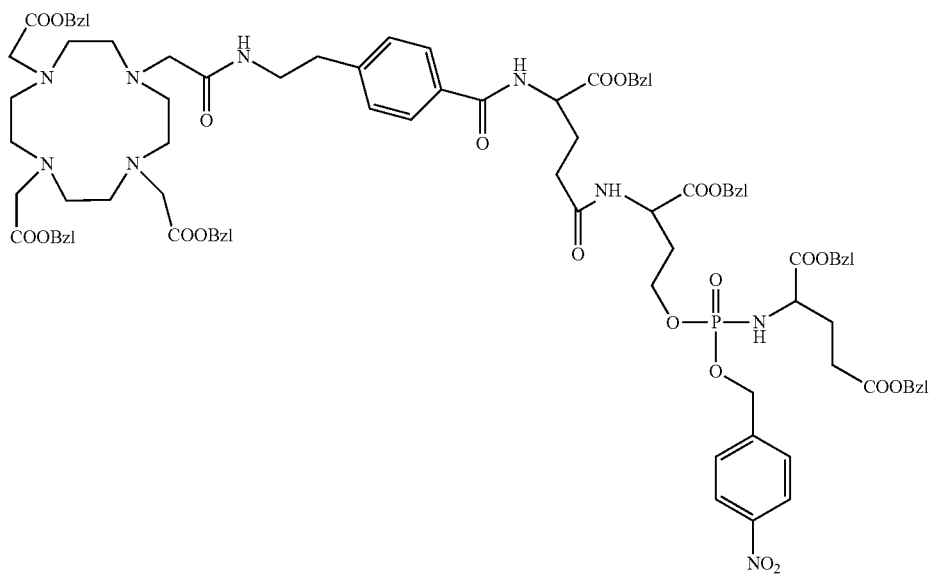

6
MW 1756.88

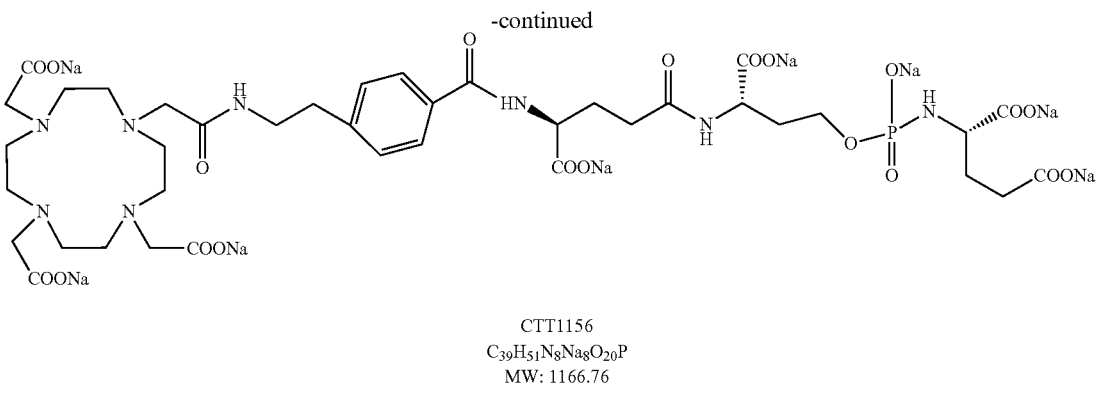

CTT1156
$C_{39}H_{51}N_8Na_8O_{20}P$
MW: 1166.76

Compound 6 (220 mg, MW 1756.88, 0.125 mmol) was dissolved in THF (15 mL), followed by addition of $NaHCO_3$ (84 mg, MW 84, 1.0 mmol) in double distilled water (10 mL) and 10% Pd/C (220 mg). Hydrogenation was performed under 1 atm $H_2$ for 18 h. The catalyst was filtered off and washed with double distilled water twice (5 mL×2). The filtrates were combined and further filtered through a syringe filter. The filtrate was evaporated to dryness and the residue was triturated with acetonitrile twice (25 mL×2), washed with acetone once (15 mL), ethyl acetate three times (20 mL×3) and ether once (20 mL), dried in vacuo for 5 h to yield off-white powder. Weight: 115 mg, yield: 79%.

BIBLIOGRAPHY

1. Liu S. Bifunctional coupling agents for radiolabeling of biomolecules and target-specific delivery of metallic radionuclides. Adv Drug Deliv Rev. 2008; 60(12):1347-70. PMCID: 2539110.
2. Breeman W A, Verbruggen A M. The 68Ge/68Ga generator has high potential, but when can we use 68Ga-labelled tracers in clinical routine? Eur J Nucl Med Mol Imaging. 2007; 34(7):978-81. PMCID: 1914228.
3. Paudyal P, Paudyal B, Hanaoka H, Oriuchi N, Iida Y, Yoshioka H, et al. Imaging and biodistribution of Her2/neu expression in non-small cell lung cancer xenografts with Cu-labeled trastuzumab PET. Cancer Sci. 2010; 101(4):1045-50.
4. Wood K A, Wong W L, Saunders M I. [(64)Cu]diacetyl-bis(N(4)-methyl-thiosemicarbazone)—a radiotracer for tumor hypoxia. Nucl Med Biol. 2008; 35(4):393-400.
5. Lane S R, Nanda P, Rold T L, Sieckman G L, Figueroa S D, Hoffman T J, et al. Optimization, biological evaluation and microPET imaging of copper-64-labeled bombesin agonists, [64Cu-NO2A-(X)-BBN(7-14)NH2], in a prostate tumor xenografted mouse model. Nucl Med Biol. 2010; 37(7):751-61.
6. Vosjan M J, Perk L R, Visser G W, Budde M, Jurek P, Kiefer G E, et al. Conjugation and radiolabeling of monoclonal antibodies with zirconium-89 for PET imaging using the bifunctional chelate p-isothiocyanatobenzyl-desferrioxamine. Nat Protoc. 2010; 5(4):739-43.
7. Dijkers E C, Oude Munnink T H, Kosterink J G, Brouwers A H, Jager P L, de Jong J R, et al. Biodistribution of 89Zr-trastuzumab and PET imaging of HER2-positive lesions in patients with metastatic breast cancer. Clin Pharmacol Ther. 2010; 87(5):586-92.
8. Eckelman W. The application of receptor theory to receptor-binding and enzyme-binding oncologic radiopharmaceuticals. Nucl Med Biol. 1994; 21:759-69.
9. Eckelman W C. Sensitivity of New Radiopharmaceuticals. Nucl Med Biol. 1998; 25(3):169-73.
10. Banerjee S R, Pullambhatla M, Byun Y, Nimmagadda S, Green G, Fox J J, et al. 68Ga-labeled inhibitors of prostate-specific membrane antigen (PSMA) for imaging prostate cancer. J Med Chem. 2010; 53(14):5333-41.

Definitions

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PSMA with a compound includes the administration of a compound described herein to an individual or patient, such as a human, as well as, for example, introducing a compound into a sample containing a cellular or purified preparation containing PSMA.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. In certain embodiments, the pharmaceutically acceptable salt is a sodium salt. Those skilled in the art will recognize a wide variety of non-toxic pharmaceutically acceptable addition salts.

Pharmaceutical compositions suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, and benzo[d][1,3]dioxol-5-yl. In certain embodiments, the bicyclic aryl is naphthyl or a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

The invention claimed is:
1. A compound of the formula

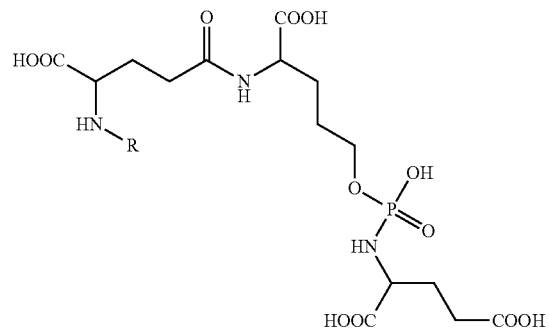

or a pharmaceutically acceptable salt thereof, wherein
R comprises a divalent linking group bonded to a chelating agent, wherein the divalent linking agent comprises

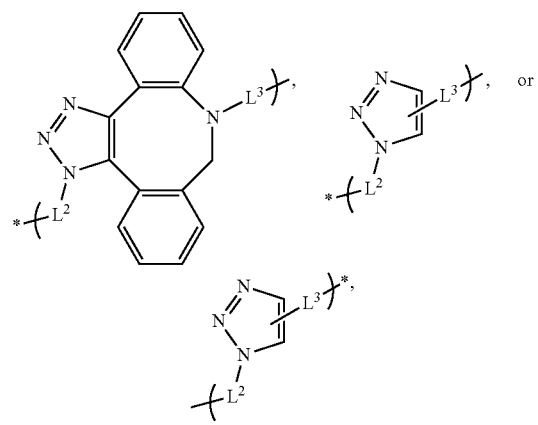

wherein
$L^2$ is —$(CH_2)_tN(H)$—*, wherein
t is 1 to 30; and
the *-end is attached to the chelating agent;
$L^3$ is #—$(CH_2)_u$—C(O)—, #—$(CH_2)_u$—Z—Y—C(O)—, #—C(O)—$(CH_2)_u$—C(O)— or #—C(O)—$(CH_2)_u$—Z—Y—C(O)—, wherein
u is 1 to 30; and
the # end of $L^3$ is attached to the dibenzocyclooctyne or triazolyl group above;

Y is **—CH$_2$CH$_2$—(OCH$_2$CH$_2$)$_n$—, wherein
n is 1-20; and
the **-end is attached to Z; and
Z is —C(O)O—, —C(O)N(R$^{00}$)—, —OC(O)—, —N(R$^{00}$)C(O)—, —S(O)$_2$N(R$^{00}$)—, —N(R$^{00}$)S(O)$_2$—, —OC(O)O—, —OC(O)N(R$^{00}$)—, —N(R$^{00}$)C(O)O—, or —N(R$^{00}$)C(O)N(R$^{00}$)—, wherein each R$^{00}$ is independently hydrogen or C$_1$-C$_6$ alkyl;
and —(C(O)(CH$_2$)$_p$—(C(O))$_{0-1}$—NH)—*, wherein
p is 1-30; and
the *-end is attached to L$^3$;
wherein the chelating agent is optionally associated with a PET-active or therapeutic radioisotope.

2. The compound of claim 1, wherein the divalent linking group is a combination of

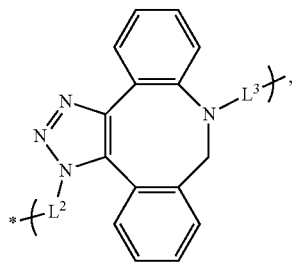

wherein
L$^2$ is —(CH$_2$)$_t$N(H)—*, wherein
t is 1 to 30; and
the *-end is attached to the chelating agent;
L$^3$ is #—(CH$_2$)$_u$—C(O)—, #—(CH$_2$)$_u$—Z—Y—C(O)—, #—C(O)—(CH$_2$)$_u$—C(O)— or #—C(O)—(CH$_2$)$_u$—Z—Y—C(O)—, wherein
u is 1 to 30; and
the # end of L$^3$ is attached to the dibenzocyclooctyne or triazolyl group above;
Y is **—CH$_2$CH$_2$—(OCH$_2$CH$_2$)$_n$—, wherein
n is 1-20; and
the **-end is attached to Z; and
Z is —C(O)O—, —C(O)N(R$^{00}$)—, —OC(O)—, —N(R$^{00}$)C(O)—, —S(O)$_2$N(R$^{00}$)—, —N(R$^{00}$)S(O)$_2$—, —OC(O)O—, —OC(O)N(R$^{00}$)—, —N(R$^{00}$)C(O)O—, or —N(R$^{00}$)C(O)N(R$^{00}$)—, wherein each R$^{00}$ is independently hydrogen or C$_1$-C$_6$ alkyl;
and —(C(O)(CH$_2$)$_p$—(C(O))$_{0-1}$—NH)—*, wherein
p is 1-30; and
the *-end is attached to L$^3$.

3. The compound of claim 1, wherein the divalent linking group is a combination of

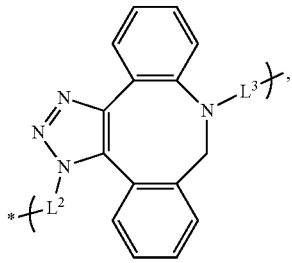

wherein
L$^2$ is —(CH$_2$)$_t$N(H)—*, wherein
t is 1 to 30; and
the *-end is attached to the chelating agent;
L$^3$ is #—C(O)—(CH$_2$)$_u$—Z—Y—C(O)—, wherein
u is 1 to 30; and
the # end of L$^3$ is attached to the dibenzocyclooctyne or triazolyl group above;
Y is **—CH$_2$CH$_2$—(OCH$_2$CH$_2$)—, wherein
n is 1-20; and
the **-end is attached to Z; and
Z is —C(O)O—, —C(O)N(R$^{00}$)—, —OC(O)—, —N(R$^{00}$)C(O)—, —S(O)$_2$N(R$^{00}$)—, —N(R$^{00}$)S(O)$_2$—, —OC(O)O—, —OC(O)N(R$^{00}$)—, —N(R$^{00}$)C(O)O—, or —N(R$^{00}$)C(O)N(R$^{00}$)—, wherein each R$^{00}$ is independently hydrogen or C$_1$-C$_6$ alkyl;
and —(C(O)(CH$_2$)$_p$—(C(O))$_{0-1}$—NH)—*, wherein
p is 1-30; and
the *-end is attached to L$^3$.

4. The compound of claim 3, wherein Z is —N(R$^{00}$)C(O)—.

5. The compound of claim 1, wherein the chelating agent comprises DOTA, NOTA, PCTA, DO3A, or desferrioxamine.

6. The compound of claim 1, wherein the chelating agent comprises DOTA.

7. The compound of claim 1, wherein the chelating agent is associated with $^{89}$Zr, $^{64}$Cu, $^{68}$Ga, $^{186/188}$Re, $^{90}$Y, $^{177}$Lu, $^{153}$Sm, $^{213}$Bi, $^{225}$Ac, or $^{223}$Ra.

8. The compound of claim 1, wherein the therapeutic radioisotope is $^{177}$Lu.

9. A pharmaceutical composition comprising a compound of claim 1 and a pharmaceutically acceptable carrier.

10. A method for imaging one or more cancer cells in a patient, the method comprising administering to the patient a compound of claim 1 associated with a PET-active radioisotope, and imaging the patient with PET imaging.

* * * * *